(12) United States Patent
Kaspar et al.

(10) Patent No.: US 9,415,121 B2
(45) Date of Patent: Aug. 16, 2016

(54) DELIVERY OF MECP2 POLYNUCLEOTIDE USING RECOMBINANT AAV9

(71) Applicants: Brian K. Kaspar, Westerville, OH (US); Kevin Foust, Westerville, OH (US)

(72) Inventors: Brian K. Kaspar, Westerville, OH (US); Kevin Foust, Westerville, OH (US)

(73) Assignee: NATIONWIDE CHILDREN'S HOSPITAL, Columbus, OH (US)

( * ) Notice: Subject to any disclaimer, the term of this patent is extended or adjusted under 35 U.S.C. 154(b) by 0 days.

(21) Appl. No.: 13/830,515

(22) Filed: Mar. 14, 2013

(65) Prior Publication Data

US 2013/0225666 A1      Aug. 29, 2013

Related U.S. Application Data

(63) Continuation-in-part of application No. 13/270,840, filed on Oct. 11, 2011, now abandoned, which is a continuation of application No. 13/035,777, filed on Feb. 25, 2011, now abandoned, which is a continuation-in-part of application No. PCT/US2009/068818, filed on Dec. 18, 2009.

(60) Provisional application No. 61/308,884, filed on Feb. 26, 2010, provisional application No. 61/139,470, filed on Dec. 19, 2008, provisional application No. 61/678,458, filed on Aug. 1, 2012.

(51) Int. Cl.
| | |
|---|---|
| *A61K 48/00* | (2006.01) |
| *C12N 15/86* | (2006.01) |
| *C07K 14/47* | (2006.01) |
| *C12N 7/00* | (2006.01) |

(52) U.S. Cl.
CPC ........... *A61K 48/0075* (2013.01); *A61K 48/005* (2013.01); *C07K 14/47* (2013.01); *C07K 14/4702* (2013.01); *C12N 7/00* (2013.01); *C12N 15/86* (2013.01); *C12N 2750/14121* (2013.01); *C12N 2750/14132* (2013.01); *C12N 2750/14143* (2013.01); *C12N 2830/008* (2013.01)

(58) Field of Classification Search
CPC ... C07K 14/4702; A61K 48/005; C12N 15/86
See application file for complete search history.

(56) References Cited

U.S. PATENT DOCUMENTS

| | | |
|---|---|---|
| 5,173,414 A | 12/1992 | Lebkowski et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,566,118 B1 | 5/2003 | Atkinson et al. |
| 7,198,951 B2 | 4/2007 | Gao et al. |
| 2004/0076613 A1 | 4/2004 | Mazarakis et al. |
| 2005/0053922 A1 | 3/2005 | Schaffer et al. |
| 2007/0280906 A1 | 12/2007 | Petras |
| 2009/0202490 A1 | 8/2009 | Schaffer et al. |
| 2010/0130594 A1 | 5/2010 | Barkats |
| 2010/0240739 A1 | 9/2010 | Barkats |

FOREIGN PATENT DOCUMENTS

| | | |
|---|---|---|
| WO | WO-95/13365 A1 | 5/1995 |
| WO | WO-95/13392 A1 | 5/1995 |
| WO | WO-96/17947 A1 | 6/1996 |
| WO | WO-97/06243 A1 | 2/1997 |
| WO | WO-97/08298 A1 | 3/1997 |
| WO | WO-97/09441 A2 | 3/1997 |
| WO | WO-97/21825 A1 | 6/1997 |
| WO | WO-98/09657 A2 | 3/1998 |
| WO | WO-99/11764 A2 | 3/1999 |
| WO | WO-01/83692 A2 | 11/2001 |
| WO | WO-2009013290 A1 | 1/2009 |
| WO | WO-2009/043936 A1 | 4/2009 |
| WO | WO-2011/112902 A2 | 9/2011 |

OTHER PUBLICATIONS

Kosai et al, Molecular Therapy, 2005, 11, S24—Abstract 58.*
Cearley et al, Molecular Therapy, 2006, 13:528-537.*
Royo et al, Brain Research, 2008, 1190:15-22.*
Nagai et al, Developmental Brain Research, 2005, 157:103-106.*
Eck et al., 1996 (Goodman & Gilman's The Pharmacological Basis of Therapeutics, McGraw-Hill, New York, p. 77-101).*
Turner et al, (Journal of the American Association for Laboratory Animal Science, 50(5): 600-613, 2011).*
Abbott et al., Astrocyte-endothelial interactions at the blood-brain barrier, Nat. Rev. Neurosci., 7(1):41-53 (2006).
Abbott et al., Transporting therapeutics across the blood-brain barrier, Mol. Med. Today, 2(3):106-13 (1996).
Abbott, Astrocyte-endothelial interactions and blood-brain barrier permeability, J. Anat., 200(6):629-38 (2002).
Abbott, pp. 189-208, IN: Dermietzel et al. (eds.), Blood-Brain Interfaces—From Ontology to Artificial Barriers, Wiley-VCH Weinheim Germany (2006).
Al-Sarraf et al., Changes in the kinetics of the acidic amino acid brain and CSF uptake during development in the rat, Brain Res. Dev. Brain Res., 102(1):127-34 (1997).

(Continued)

*Primary Examiner* — Deborah Crouch
*Assistant Examiner* — Magdalene Sgagias
(74) *Attorney, Agent, or Firm* — Marshall, Gerstein & Borun LLP

(57) ABSTRACT

The present invention relates to Adeno-associated virus 9 methods and materials useful for systemically delivering polynucleotides across the blood brain barrier. Accordingly, the present invention also relates to methods and materials useful for systemically delivering polynucleotides to the central and peripheral nervous systems. The present invention also relates to Adeno-associated virus type 9 methods and materials useful for intrathecal delivery of polynucleotides. Use of the methods and materials is indicated, for example, for treatment of lower motor neuron diseases such as spinal muscle atrophy and amyotrophic lateral sclerosis as well as Pompe disease and lysosomal storage disorders. Use of the methods and materials is also indicated, for example, for treatment of Rett syndrome.

3 Claims, 25 Drawing Sheets

(56) References Cited

OTHER PUBLICATIONS

Avila et al., Trichostatin A increases SMN expression and survival in a mouse model of spinal muscular atrophy, J. Clin. Invest., 117(3):659-71 (2007).
Ayuso et al., High AAV vector purity results in serotype- and tissue-independent enhancement of transduction efficiency, Gene Ther., 17(4):503-10 (2010).
Azzouz et al., Lentivector-mediated SMN replacement in a mouse model of spinal muscular atrophy, J. Clin. Invest., 114(12):1726-31 (2004).
Azzouz et al., VEGF delivery with retrogradely transported lentivector prolongs survival in a mouse ALS model, Nature, 429(6990):413-7 (2004).
Ballas et al., Non-cell autonomous influence of MeCP2-deficient glia on neuronal dendritic morphology, Nat. Neurosci., 12(3):311-7 (2009).
Bauer et al., Neural induction of the blood-brain barrier: still an enigma, Cell Mol. Neurobiol., 20(1):13-28 (2000).
Baughan et al., Stimulating full-length SMN2 expression by delivering bifunctional RNAs via a viral vector, Mol. Ther., 14(1):54-62 (2006).
Begley et al., Structural and functional aspects of the blood-brain barrier, Prog. Drug Res., 61:40-78 (2003).
Behnsen, Zeit Zellforsch Mikrosk Anat., 4:515-72 (1905).
Bevan et al., Systemic gene delivery in large species for targeting spinal cord, brain, and peripheral tissues for pediatric disorders, Mol. Ther., 19(11):1971-80 (2011).
Butchbach et al., Abnormal motor phenotype in the SMNDelta7 mouse model of spinal muscular atrophy, Neurobiol. Dis., 27(2):207-19 (2007).
Caley et al., Development of the blood vessels and extracellular spaces during postnatal maturation of rat cerebral cortex, J. Comp. Neurol., 138(1):31-47 (1970).
Carter, Adeno-associated virus vectors, Curr. Opin. Biotechnol 1533-539 (1992).
Cearley et al., Expanded repertoire of AAV vector serotypes mediate unique patterns of transduction in mouse brain, Mol. Ther., 16(10):1710-8 (2008).
Chang et al., Treatment of spinal muscular atrophy by sodium butyrate, Proc. Natl. Acad. Sci. USA, 98(17):9808-13 (2001).
Chen et al., Deficiency of methyl-CpG binding protein-2 in CNS neurons results in a Rett-like phenotype in mice, Nat. Genet., 27(3):327-31 (2001).
Clark et al., A stable cell line carrying adenovirus-inducible rep and cap genes allows for infectivity titration of adeno-associated virus vectors, Gene Ther., 3(12):1124-32 (1996).
Clark et al., Development of enzymes of energy metabolism in the neonatal mammalian brain, Dev. Neurosci., 15(3-5):174-80 (1993).
Clark et al., Highly purified recombinant adeno-associated virus vectors are biologically active and free of detectable helper and wild-type viruses, Hum. Gene Ther., 10(6):1031-9 (1999).
Costa et al., Developmental neuropathology of environmental agents, Annu. Rev. Pharmacol. Toxicol., 44:87-110 (2004).
Cserr et al., Blood-brain interfaces in vertebrates: a comparative approach, Am. J. Physiol., 246:277-87 (1984).
Davson et al., Symposium on membrane transport. Transport in the central nervous system, Proc. R. Soc. Med., 60(4):326-9 (1967).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).
Dehouck et al., An easier, reproducible, and mass-production method to study the blood-brain barrier in vitro, J. Neurochem., 54(5):1798-801 (1990).
Del Gaudio et al., Increased MECP2 gene copy number as the result of genomic duplication in neurodevelopmentally delayed males, Genet. Med., 8(12):784-92 (2006).
Dodge et al., Delivery of AAV-IGF-1 to the CNS extends survival in ALS mice through modification of aberrant glial cell activity, Mol. Ther., 16(6):1056-64 (2008).
Ford, Selected maturational changes observed in the postnatal rat brain, Prog. Brain Res., 40(0):1-12 (1973).
Foust et al., Intravascular AAV9 preferentially targets neonatal neurons and adult astrocytes, Nat. Biotechnol., 27(1):59-65 (2009).
Foust et al., Rescue of the spinal muscular atrophy phenotype in a mouse model by early postnatal delivery of SMN, Nat. Biotechnol., 28(3):271-4 (2010).
Friez et al., Recurrent infections, hypotonia, and mental retardation caused by duplication of MECP2 and adjacent region in Xq28, Pediatrics, 118(6):e1687-95 (2006).
Fu et al., Self-complementary adeno-associated virus serotype 2 vector: global distribution and broad dispersion of AAV-mediated transgene expression in mouse brain, Mol. Ther., 8(6):911-7 (2003).
Gadalla et al., Improved survival and reduced phenotypic severity following AAV9/MECP2 gene transfer to neonatal and juvenile male Mecp2 knockout mice, Mol. Ther., 21(1):18-30 (2013).
Gao et al., Glades of Adeno-associated viruses are widely disseminated in human tissues, J. Virol., 78(12):6381-8 (2004).
Gavrilina et al., Neuronal SMN expression corrects spinal muscular atrophy in severe SMA mice while muscle-specific SMN expression has no phenotypic effect, Hum. Mol. Genet., 17(8):1063-75 (2008).
Grady et al., Cerebellar synaptic defects and abnormal motor behavior in mice lacking alpha- and beta-dystrobrevin, J. Neurosci., 26(11):2841-51 (2006).
Guy et al., A mouse Mecp2-null mutation causes neurological symptoms that mimic Rett syndrome, Nat. Genet., 27(3):322-6 (2001).
Guy et al., Reversal of neurological defects in a mouse model of Rett syndrome, Science, 315(5815):1143-7 (2007).
Haseloff et al., In search of the astrocytic factor(s) modulating blood-brain barrier functions in brain capillary endothelial cells in vitro, Cell Mol. Neurobiol., 25(1):25-39 (2005).
Hawkins et al., The blood-brain barrier/neurovascular unit in health and disease, Pharmacol. Rev., 57(2):173-85 (2005).
Hayashi et al., Induction of various blood-brain barrier properties in non-neural endothelial cells by close apposition to co-cultured astrocytes, Glia, 19(1):13-26 (1997).
Hermonat et al., Use of adeno-associated virus as a mammalian DNA cloning vector: transduction of neomycin resistance into mammalian tissue culture cells, Proc. Natl. Acad. Sci. USA, 81(20):6466-70 (1984).
Hsieh-Li et al., A mouse model for spinal muscular atrophy, Nat. Genet., 24(1):66-70 (2008).
Iadecola, Neurovascular regulation in the normal brain and in Alzheimer's disease. Nat. Rev. Neurosci., 5(5):347-60 (2004).
Inagaki et al., Robust systemic transduction with AAV9 vectors in mice: efficient global cardiac gene transfer superior to that of AAV8, Mol. Ther., 14(1):45-53 (2006).
International Preliminary Report on Patentability for corresponding international application No. PCT/US2009/068818, dated Jun. 21, 2011.
International Search Report and Written Opinion for corresponding international application No. PCT/US09/68818, mailing date Mar. 2, 2010.
Kaplitt et al., Safety and tolerability of gene therapy with an adeno-associated virus (AAV) borne GAD gene for Parkinson's disease: an open label, phase I trial, Lancet, 369(9579):2097-105 (2007).
Kaspar et al., Retrograde viral delivery of IGF-1 prolongs survival in a mouse ALS model, Science, 301(5634):839-42 (2003).
Katz et al., Preclinical research in Rett syndrome: setting the foundation for translational success, Dis. Model Mech., 5(6):733-45 (2012).
Kempermann et al., Genetic influence on neurogenesis in the dentate gyrus of adult mice, Proc. Natl. Acad. Sci. USA, 94(19)1 0409-14 (1997).
Klein et al., AAV8, 9, Rh10, Rh43 vector gene transfer in the rat brain: effects of serotype, promoter and purification method, Mol. Ther., 16(1):89-96 (2008).
Kong et al., Impaired synaptic vesicle release and immaturity of neuromuscular junctions in spinal muscular atrophy mice, J. Neurosci., 29(3):842-51 (2009).
Kota et al., Follistatin gene delivery enhances muscle growth and strength in nonhuman primates, Sci. Trans!. Med., 1:6-15 (2009).

(56) References Cited

OTHER PUBLICATIONS

Laughlin et al., Cloning of infectious adeno-associated virus genomes in bacterial plasmids, Gene, 23(1):65-73 (1983).
Le et al., SMNDelta7, the major product of the centromeric survival motor neuron (SMN2) gene, extends survival in mice with spinal muscular atrophy and associates with full-length SMN, Hum. Mol. Genet., 14(6):845-57 (2005).
Lebkowski et al., Adeno-associated virus: a vector system for efficient introduction and integration of DNA into a variety of mammalian cell types, Mol. Cell Biol., 8:3988-96 (1988).
Lioy et al., A role for glia in the progression of Rett's syndrome, Nature, 475:497-500 (2011).
Marks et al., Safety and tolerability of intraputaminal delivery of CERE-120 (adeno-associated virus serotype 2-neurturin) to patients with idiopathic Parkinson's disease: an open-label, phase I trial, Lancet Neurol., 7(5):400-8 (2008).
McAllister et al., Mechanisms of glucose transport at the blood-brain barrier: an in vitro study, Brain Res., 904(1):20-30 (2001).
McCarty et al., Adeno-associated virus terminal repeat (TR) mutant generates self-complementary vectors to overcome the rate-limiting step to transduction in vivo, Gene Ther., 10(26):2112-8 (2003).
McIlwain, "Chemical and enzymic make-up of the brain during development" IN: McIlwain, Biochemistry and the Central Nervous System, London: Churchill Livingstone (1966).
McLaughlin et al., Adeno-associated virus general transduction vectors: analysis of proviral structures, J. Virol., 62(6):1963-73 (1988).
Monani et al., A transgene carrying an A2G missense mutation in the SMN gene modulates phenotypic severity in mice with severe (type I) spinal muscular atrophy, J. Cell Biol., 160(1):41-52 (2003).
Monani et al., The human centromeric survival motor neuron gene (SMN2) rescues embryonic lethality in Smn(−/−) mice and results in a mouse with spinal muscular atrophy, Hum. Mol. Genet., 9(3):333-9 (2000).
Mori et al., Two novel adeno-associated viruses from cynomolgus monkey: pseudotyping characterization of capsid protein, Virology, 330(2):375-83 (2004).
Muzyczka, Use of adeno-associated virus as a general transduction vector for mammalian cells, Curr. Top Microbiol. Immunol., 158:97-129 (1992).
Narver et al., Sustained improvement of spinal muscular atrophy mice treated with trichostatin A plus nutrition, Ann. Neurol., 64(4):465-70 (2008).
Oertle et al., Nogo-A inhibits neurite outgrowth and cell spreading with three discrete regions, J. Neurosci., 23(13):5393-406 (2003).
Oprea et al., Plastin 3 is a protective modifier of autosomal recessive spinal muscular atrophy, Science, 320(5875):524-7 (2008).
Pacak et al., Recombinant adeno-associated virus serotype 9 leads to preferential cardiac transduction in vivo, Circ. Res., 99(4):e3-9 (2006).
Palli et al., Improved ecdysone receptor-based inducible gene regulation system, Eur. J. Biochem., 270(6):1308-15 (2003).
Pardridge, Drug and gene targeting to the brain with molecular Trojan horses, Nat. Rev. Drug Discov., 1(2):131-9 (2002).
Paul et al., Increased viral titer through concentration of viral harvests from retroviral packaging lines, Hum. Gene Ther., 4(5):609-15 (1993).
Penta, Sulla colorazione vitale del sistema nervoso central negli animali neonati, Riv. Neurol., 5:62-80 (1932).
Perrin et al., An experimental rabies vaccine produced with a new BHK-21 suspension cell culture process: use of serum-free medium and perfusion-reactor system, Vaccine, 13(13)1244-50 (1995).
Ralph et al., Silencing mutant SOD1 using RNAi protects against neurodegeneration and extends survival in an ALS model, Nat. Med., 11(4):429-33 (2005).
Rastegar et al., MECP2 isoform-specific vectors with regulated expression for Rett syndrome gene therapy, PLoS One, 4(8):e6810 (2009).
Reichenbach et al., pp. 19-35 IN: Kettemann et al., Neuroglia, 2nd ed., New York: Oxford University Press (2004).
Risau et al., Development of the blood-brain barrier, Trends Neurosci., 13(5):174-8 (1990).
Risau et al., Differentiation-dependent expression of proteins in brain endothelium during development of the blood-brain barrier, Dev. Biol., 117(2):537-45 (1986).
Robinson et al., Morphological and functional reversal of phenotypes in a mouse model of Rett syndrome, Brain, 135(Pt. 9):2699-710 (2012).
Rubin et al., A cell culture model of the blood-brain barrier, J. Cell Biol., 115(6):1725-35 (1991).
Ruffing et al., Mutations in the carboxy terminus of adeno-associated virus 2 capsid proteins affect viral infectivity: lack of an RGD integrin-binding motif, J. Gen. Virol., 75(Pt. 12):3385-92 (1994).
Samulski et al., Cloning of adeno-associated virus into pBR322: rescue of intact virus from the recombinant plasmid in human cells, Proc. Natl. Acad. Sci. USA, 79(6):2077-81 (1982).
Samulski et al., Helper-free stocks of recombinant adeno-associated viruses: normal integration does not require viral gene expression, J. Virol., 63(9):3822-8 (1989).
Saunders et al., On the progestational activity of 17alpha-ethynyl-17-hydroxy-5(10)-estren-3-one (norethynodrel), Endocrinology, 60(6):804-5 (1957).
Schlageter et al., Microvessel organization and structure in experimental brain tumors: microvessel populations with distinctive structural and functional properties, Microvasc. Res., 58(3):312-28 (1999).
Schnepp et al., Highly purified recombinant adeno-associated virus vectors. Preparation and quantitation, Methods Mol. Med., 69:427-43 (2002).
Senapathy et al., Molecular cloning of adeno-associated virus variant genomes and generation of infectious virus by recombination in mammalian cells, J. Biol. Chem., 259(7):4661-6 (1984).
Siegel at al., Francis Crick's legacy for neuroscience: between the alpha and the Omega, PLoS Biol., 2(12):e419 (2004).
Skene et al., Neuronal MeCP2 is expressed at near histone-octamer levels and globally alters the chromatin state, Mol. Cell, 37(4):457-68 (2010).
Sobue et al., Induction of blood-brain barrier properties in immortalized bovine brain endothelial cells by astrocytic factors, Neurosci. Res., 35(2):155-64 (1999).
Srivastava et al., Nucleotide sequence and organization of the adeno-associated virus 2 genome, J. Virol., 45(2):555-64 (1983).
Stern et al., Platelet lipoxygenase in spontaneously hypertensive rats, Hypertension, 27(5):1149-52 (1996).
Stewart et al., Interendothelial junctional changes underlie the developmental 'tightening' of the blood-brain barrier, Brain Res., 429(2):271-81 (1987).
Traschin et al., A human parvovirus, adeno-associated virus, as a eucaryotic vector: transient expression and encapsidation of the procaryotic gene for chloramphenicol acetyltransferase, Mol. Cell Biol., 4:2072-81 (1984).
Tratschin et al., Adeno-associated virus vector for high-frequency integration, expression, and rescue of genes in mammalian cells, Mol. Cell Biol., 5(11):3251-60 (1985).
Urlinger et al., Exploring the sequence space for tetracycline-dependent transcriptional activators: novel mutations yield expanded range and sensitivity, Proc. Natl. Acad. Sci. USA, 97(14):7963-8 (2000).
Verkman, Aquaporin water channels and endothelial cell function, J. Anat., 200(6):617-27 (2002).
Virgintino et al., Immunolocalization of tight junction proteins in the adult and developing human brain, Histochem. Cell Biol., 122(1):51-9 (2004).
Vorbrodt et al., Localization of alkaline phosphatase activity in endothelia of developing and mature mouse blood-brain barrier, Dev. Neurosci., 8:1-13 (1986).
Wang et al., Adeno-associated virus serotype 8 efficiently delivers genes to muscle and heart, Nat. Biotechnol., 23(3):321-8 (2005).
Wang et al., Decreased synaptic activity shifts the calcium dependence of release at the mammalian neuromuscular junction in vivo, J. Neurosci., 24(47):10687-92 (2004).

(56) References Cited

OTHER PUBLICATIONS

Watson et al., Postnatal growth and morphological development of the brain: a species comparison, Birth Defects Res. B Dev. Reprod. Toxicol., 77(5):471-84 (2006).

Wolburg et al., Tight junctions of the blood-brain barrier: development, composition and regulation, Vascul. Pharmacol., 38(6):323-37 (2002).

Wolburg, pp. 77-107 IN: Dermietzel at al., (eds.), Blood-Brain Interfaces—from Ontogeny to Artificial Barriers, Wiley-VCH (2006).

Worgall et al., Treatment of late infantile neuronal ceroid lipofuscinosis by CNS administration of a serotype 2 adeno-associated virus expressing CLN2 cDNA, Hum. Gene Ther. 19(5):463-74 (2008).

Yamanaka et al., Astrocytes as determinants of disease progression in inherited amyotrophic lateral sclerosis, 11(3):251-3 (2008).

Inagaki, et al., "Robust Systemic Transduction with AAV9 Vectors in Mice: Efficient Global Cardiac Gene Transfer Superior to That of AAV8," Molecular Therapy, vol. 14, No. 1, pp. 45-53 (Jul. 2006).

\* cited by examiner

Figure 22 scAAV MECP2

```
   1 gcccaatacg caaaccgcct ctccccgcgc gttggccgat tcattaatgc agctgattct
  61 aacgaggaaa gcacgttata cgtgctcgtc aaagcaacca tagtacgcgc cctgtagcgg
 121 cgcattaagc gcggcgggtg tggtggttac gcgcagcgtg accgctacac ttgccagcgc
 181 cctagcgccc gctcctttcg ctttcttccc ttcctttctc gccacgttcg ccggctttcc
 241 ccgtcaagct ctaaatcggg ggctcccttt agggttccga tttagtgctt tacggcacct
 301 cgaccccaaa aaacttgatt agggtgatgg ttcacgtagt gggccatcgc cctgatagac
 361 ggttttcgc cctttgacgt tggagtccac gttctttaat agtggactct tgttccaaac
 421 tggaacaaca ctcaaccata tctcggtcta ttcttttgat ttataaggga ttttgccgat
 481 ttcggcctat tggttaaaaa atgagctgat ttaacaaaaa tttaacgcga attttaacaa
 541 aatattaacg cttacaattt aaatatttgc ttatacaatc ttcctgtttt tggggctttt
 601 ctgattatca accgggtac atatgattga catgctagtt ttacgattac cgttcatcgc
 661 cctgcgcgct cgctcgctca ctgaggccgc ccgggcaaag cccgggcgtc gggcgacctt
 721 tggtcgcccg gcctcagtga gcgagcgagc gcgcagagag ggagtggaat tcacgcgtgg
 781 atctgaattc aattcacgcg tggtaccgag ctcggatcca ctagtaacgg ccgccagtgt
 841 gctggaattc gcccttaatt ttccggacgg gttttaccac agccctctct ccgagaggag
 901 ggagcgcgcg cgcaaccgat gccgggaccc cgcacgcag acgtcgcgcc ccgccctccc
 961 gaccagcctg tgtgctgctg cacctgcccg cccgcgcccc accccttgct ctttgtcgag
1021 attacccttc attggttgtg gagcccaggc tgggcggag cctagcggg gacgccctca
1081 attggcagga gttcctgtct gtttaggcag ggaaaagagg cggaccccat tcagctgcgg
1141 attggtggag ttctactgtc acttggaaaa aagaggcggc tagggcacag aggggctggt
1201 tttgtgggca gcatttgaat gttgaggatt aactgggccc ttgtgactc tggcgcttaa
1261 ggaagtctag gctcttggcg cctattagag cctccctgct gagtagttca ccattgtgat
1321 aagcatttga cttcaccagc atttcttat tatcattttc tgtagaagta gcaaagttgc
1381 ctgttgagga gcctggcgtt gttccaagcc aagggacttg ttttaaaggg tctactgatt
1441 gtattattac actaaattag cagatgtcgc actcttaagg ctgacagtaa aatcaacata
1501 tcaaaccttg gtctttgcag acgtttataa tgggcagatg gtgtgtgcca agcccataag
1561 agatcggtct gtcattgttg aatcagatgg tttgataact ggtaagttta gtcttttgt
1621 cttttatttc aggtcccgga tccggtggtg gtgcaaatca aagaactgct cctcagtgga
1681 tgttgccttt acttctaggc ctgtacgaa gtgttacttc tgctctaaaa gctgcggaat
1741 tgtacccgcg gccgatccac cggttttaag ggccgaggcg gccagatctt tcgaagatat
1801 ggccgcgct gccgccaccg ccgccgcgcc cgccgcgccg agcggaggag gaggaggagg
1861 cgaggaggag agactggagg aaaagtcaga agaccaggat ctccaggcc tcagagacaa
1921 gccactgaag tttaagaagg cgaagaaaga caagaaggag gacaaagaag gcaagcatga
1981 gccactacaa ccttcagccc accattctgc agagccagca gaggcaggca aagcagaaac
2041 atcagaaagc tcaggctctg cccagcagt gccagaagcc tcggcttccc ccaaacagcg
2101 gcgctccatt atccgtgacc ggggacctat gtatgatgac cccaccttgc ctgaaggttg
2161 gacacgaaag cttaaacaaa ggaagtctgg ccgatctgct ggaaagtatg atgtatattt
2221 gatcaatccc caggaaaag cttttcgctc taagtagaa ttgattgcat actttgaaaa
2281 ggtgggagac acctccttgg accctaatga ttttgacttc acggtaactg ggagagggag
2341 cccctccagg agagagcaga aaccacctaa gaagcccaaa tctcccaaag ctccaggaac
2401 tggcaggggt cggggacgcc ccaaagggag cggcactggg agaccaaagg cagcagcatc
2461 agaaggtgtt caggtgaaaa gggtcctgga aagagccct gggaaacttg ttgtcaagat
2521 gccttccaa gcatcgcctg ggggtaaggg tgagggaggt ggggctacca catctgccca
2581 ggtcatggtg atcaaacgca ctggcagaaa gcgaaaagct gaagctgacc cccaggccat
2641 tcctaagaaa cgggtgaa agctgggag tgtggtggca gctgctgcag ctgaggccaa
2701 aaagaaagcc gtgaaggagt cttccatacg gtctgtgcat gagactgtgc tccccatcaa
2761 gaagcgcaag acccgggaga cggtcagcat cgaggtcaag gaagtggtga agcccctgct
2821 ggtgtccacc cttggtgaga aaagcgggaa gggactgaag acctgcaaga gcctgggcg
2881 taaaagcaag gagagcagcc caagggcg cagcagcagt gcctcctccc cacctaagaa
2941 ggagcaccat catcaccacc atcactcaga gtccacaaag gcccccatgc cactgctccc
3001 atccccaccc ccacctgagc ctgagagctc tgaggacccc atcagccccc ctgagcctca
3061 ggacttgagc agcagcatct gcaaagaaga gagatgccc cgaggaggct cactggaaag
3121 cgatggctgc cccaaggagc cagctaagac tcagcctatg gtcgccacca ctaccacagt
```

Figure 22 (continued)

```
3181 tgcagaaaag tacaaacacc gaggggaggg agagcgcaaa gacattgttt catcttccat
3241 gccaaggcca aacagagagg agcctgtgga cagccggacg cccgtgaccg agagagttag
3301 ctgaatcggc gccgctagcg cggccgcgtt taaaccctgc aggtctagaa agcttatcga
3361 taccgtcgac tagagctcgc tgatcagcct cgactgtgcc ttctagttgc cagccatctg
3421 ttgtttgccc ctcccccgtg ccttccttga ccctggaagg tgccactccc actgtccttt
3481 cctaataaaa tgaggaaatt gcatcgcatt gtctgagtag gtgtcattct attctggggg
3541 gtggggtggg gcaggacagc aaggggagg attgggaaga caatagcagg catgctgggg
3601 agagatcgat ctgaggaacc cctagtgatg gagttggcca ctccctctct gcgcgctcgc
3661 tcgctcactg aggccgggcg accaaaggtc gcccgacgcc cgggctttgc ccgggcggcc
3721 tcagtgagcg agcgagcgcg cagagaggga gtggcccccc ccccccccc cccggcgatt
3781 ctcttgtttg ctccagactc tcaggcaatg acctgatagc ctttgtagag acctctcaaa
3841 aatagctacc ctctccggca tgaatttatc agctagaacg gttgaatatc atattgatgg
3901 tgatttgact gtctccggcc tttctcaccc gtttgaatct ttacctacac attactcagg
3961 cattgcattt aaaatatatg agggttctaa aaattttttat ccttgcgttg aaataaaggc
4021 ttctcccgca aaagtattac agggtcataa tgttttttggt acaaccgatt tagctttatg
4081 ctctgaggct ttattgctta attttgctaa ttcttttgcct tgcctgtatg atttattgga
4141 tgttggaatc gcctgatgcg gtattttctc cttacgcatc tgtgcggtat ttcacaccgc
4201 atatggtgca ctctcagtac aatctgctct gatgccgcat agttaagcca gccccgacac
4261 ccgccaacac ccgctgacgc gccctgacgg gcttgtctgc tcccggcatc cgcttacaga
4321 caagctgtga ccgtctccgg gagctgcatg tgtcagaggt tttcaccgtc atcaccgaaa
4381 cgcgcgagac gaaagggcct cgtgatacgc ctatttttat aggttaatgt catgataata
4441 atggtttctt agacgtcagg tggcactttt cggggaaatg tgcgcggaac ccctatttgt
4501 ttattttttct aaatacattc aaatatgtat ccgctcatga caataaacc ctgataaatg
4561 cttcaataat attgaaaaag gaagagtatg agtattcaac atttccgtgt cgcccttatt
4621 ccctttttttg cggcattttg ccttcctgtt tttgctcacc cagaaacgct ggtgaaagta
4681 aaagatgctg aagatcagtt gggtgcacga gtgggttaca tcgaactgga tctcaacagc
4741 ggtaagatcc ttgagagttt tcgccccgaa gaacgttttc caatgatgag cacttttaaa
4801 gttctgctat gtggcgcggt attatcccgt attgacgccg ggcaagagca actcggtcgc
4861 cgcatacact attctcagaa tgacttggtt gagtactcac cagtcacaga aaagcatctt
4921 acggatggca tgacagtaag agaattatgc agtgctgcca taaccatgag tgataacact
4981 gcggccaact tacttctgac aacgatcgga ggaccgaagg agctaaccgc ttttttgcac
5041 aacatggggg atcatgtaac tcgccttgat cgttgggaac cggagctgaa tgaagccata
5101 ccaaacgacg agcgtgacac cacgatgcct gtagcaatgg caacaacgtt gcgcaaacta
5161 ttaactggcg aactacttac tctagcttcc cggcaacaat taatagactg gatggaggcg
5221 gataaagttg caggaccact tctgcgctcg gcccttccgg ctggctggtt tattgctgat
5281 aaatctggag ccggtgagcg tgggtctcgc ggtatcattg cagcactggg gccagatggt
5341 aagccctccc gtatcgtagt tatctacacg acggggagtc aggcaactat ggatgaacga
5401 aatagacaga tcgctgagat aggtgcctca ctgattaagc attggtaact gtcagaccaa
5461 gtttactcat atatacttta gattgattta aacttcatt tttaatttaa aaggatctag
5521 gtgaagatcc ttttttgataa tctcatgacc aaaatccctt aacgtgagtt ttcgttccac
5581 tgagcgtcag accccgtaga aagatcaaa ggatcttctt gagatccttt ttttctgcgc
5641 gtaatctgct gcttgcaaac aaaaaaacca ccgctaccag cggtggtttg tttgccggat
5701 caagagctac caactctttt tccgaaggta actggcttca gcagagcgca gataccaaat
5761 actgtccttc tagtgtagcc gtagttaggc caccacttca agaactctgt agcaccgcct
5821 acatacctcg ctctgctaat cctgttacca gtggctgctg ccagtggcga taagtcgtgt
5881 cttaccgggt tggactcaag acgatagtta ccggataagg cgcagcggtc gggctgaacg
5941 gggggttcgt gcacacagcc cagcttggag cgaacgacct acaccgaact gagataccta
6001 cagcgtgagc tatgagaaag cgccacgctt cccgaaggga aaaggcgga caggtatccg
6061 gtaagcggca gggtcggaac aggagagcgc acgagggagc ttccaggggg aaacgcctgg
6121 tatctttata gtcctgtcgg gtttcgccac ctctgacttg agcgtcgatt tttgtgatgc
6181 tcgtcagggg gcggagcct atggaaaaac gccagcaacg cggcctttt acggttcctg
6241 gccttttgct ggccttttgc tcacatgttc tttcctgcgt tatcccctga ttctgtggat
6301 aaccgtatta ccgcctttga gtgagctgat accgctcgcc gcagccgaac gaccgagcgc
6361 agcgagtcag tgagcgagga agcggaagag c
```

Figure 23 scAAV MP-hMECP2

```
   1 gcccaatacg caaaccgcct ctccccgcgc gttggccgat tcattaatgc agctgattct
  61 aacgaggaaa gcacgttata cgtgctcgtc aaagcaacca tagtacgcgc cctgtagcgg
 121 cgcattaagc gcggcgggtg tggtggttac gcgcagcgtg accgctacac ttgccagcgc
 181 cctagcgccc gctcctttcg ctttcttccc ttcctttctc gccacgttcg ccggctttcc
 241 ccgtcaagct ctaaatcggg ggctcccttt agggttccga tttagtgctt tacggcacct
 301 cgaccccaaa aaacttgatt agggtgatgg ttcacgtagt gggccatcgc cctgatagac
 361 ggttttttcgc cctttgacgt tggagtccac gttctttaat agtggactct tgttccaaac
 421 tggaacaaca ctcaaccta tctcggtcta ttctttgat ttataaggga ttttgccgat
 481 ttcggcctat tggttaaaaa atgagctgat ttaacaaaaa tttaacgcga attttaacaa
 541 aatattaacg cttacaattt aaatatttgc ttatacaatc ttcctgtttt tggggctttt
 601 ctgattatca accggggtac atatgattga catgctagtt ttacgattac cgttcatcgc
 661 cctgcgcgct cgctcgctca ctgaggccgc ccgggcaaag cccgggcgtc gggcgacctt
 721 tggtcgcccg gcctcagtga gcgagcgagc gcgcagagag ggagtggaat tcacgcgtgg
 781 atctgaattc aattcacgcg tggtaccgag ctcggatcca ctagtaacgg ccgccagtgt
 841 gctggaattc gcccttaatt ttccggacgg gttttaccac agccctctct ccgagaggag
 901 ggagcgcgcg cgcaaccgat gccgggaccc cgcacggcag acgtcgcgcc ccgccctccc
 961 gaccagcctg tgtgctgctg cacctgcgcg cccgcgcccc accccttgct ctttgtcgag
1021 attacccttc attggttgtg gagcccaggc tggggcggag ccttagcggt gacgccctca
1081 attggcagga gttcctgtct gtttaggcag ggaaaagagg cggacccat tcagctgcgg
1141 attggtggag ttctactgtc acttggaaaa aagaggcggc tagggcacag agggggctggt
1201 tttgtgggca gcatttgaat gttgaggatt aactgggccc ttgtggactc tggcgcttaa
1261 ggaagtctag gctcttggcg cctattagag cctccctgct gagtagttca ccattgtgat
1321 aagcatttga cttccaccac atttcttttat tatcattttc tgtagaagta gcaaagttgc
1381 ctgttgagga gcctggcgtt gttccaagcc aagggacttg ttttaaaggg tctactgatt
1441 gtattattac actaaattag cagatgtcgc actcttaagg ctgacagtaa aatcaacata
1501 tcaaaccttg gtctttgcag acgtttataa tgggcagatg gtgtgtgcca agcccataag
1561 agatcggtct gtcattgttg aatcagatgg tttgataact ggtaagttta gtcttttttgt
1621 cttttatttc aggtcccgga tccggtggtg gtgcaaatca aagaactgct cctcagtgga
1681 tgttgccttt acttctaggc ctgtacggaa gtgttacttc tgctctaaaa gctgcggaat
1741 tgtacccgcg gccgatccac cggtatggcc gccgccgcc ccgccgcgcc gagcggagga
1801 ggaggaggag gcgaggagga gagactggaa gaaaagtcag aagaccagga cctccagggc
1861 ctcaaggaca aaccctcaa gtttaaaaag gtgaagaaag ataagaaaga agagaaagag
1921 ggcaagcatg agcccgtgca gccatcagcc caccactctg ctgagcccgc agaggcaggc
1981 aaagcagaga catcagaagg gtcaggctcc gccccggctg tgccggaagc ttctgcctcc
2041 cccaaacagc ggcgctccat catccgtgac cggggaccca tgtatgatga ccccaccctg
2101 cctgaaggct ggacacggaa gcttaagcaa aggaaatctg gccgctctgc tgggaagtat
2161 gatgtgtatt tgatcaatcc caggaaaa gcctttcgct ctaaagtgga gttgattgcg
2221 tacttcgaaa aggtaggcga cacatccctg gaccctaatg attttgactt cacggtaact
2281 gggagaggga gcccctcccg gcgagagcag aaaccaccta agaagcccaa atctcccaaa
2341 gctccaggaa ctggcagagg ccggggacgc cccaaggga gcggcaccac gagacccaag
2401 gcggccacgt cagagggtgt gcaggtgaaa agggtcctgg agaaaagtcc tgggaagctc
2461 cttgtcaaga tgccttttca aacttcgcca ggggcaagg ctgagggggg tggggccacc
2521 acatccaccc aggtcatggt gatcaaacgc cccggcagga gcgaaaagc tgaggccgac
2581 cctcaggcca ttcccaagaa acggggccga aagccgggga gtgtggtggc agccgctgcc
2641 gccgaggcca aaagaaagc cgtgaaggag tcttctatcc gatctgtgca ggagaccgta
2701 ctccccatca agaagcgcaa gacccgggag acggtcagca tcgaggtcaa ggaagtggtg
2761 aagcccctgc tggtgtccac cctcggtgag aagagcggga aggactgaa gacctgtaag
2821 agccctgggc ggaaaagcaa ggagagcagc ccaaggggc gcagcagcag cgcctcctca
2881 cccccaaga aggagcacca ccaccatcca ccactactga agtccccaaa ggccccgtg
2941 ccactgctcc caccctgcc cccacctgca cctgagcagc agagtctgca agaggagaa gatgcccaga
3001 agccccctg agcccagga cttgagcaga agcgtctgca agaggagaa gatgcccaga
3061 ggaggctcac tggagagcga cggctgcccc aaggagccag ctaagactca gcccgcggtt
3121 gccaccgccg ccacggccgc agaaaagtac aaacaccgag gggagggaga gcgcaaagac
```

Figure 23 (continued)

```
3181 attgtttcat cctccatgcc aaggccaaac agagaggagc ctgtggacag ccggacgccc
3241 gtgaccgaga gagttagctg acctgcaggt ctagaaagct tatcgatacc gtcgactaga
3301 gctcgctgat cagcctcgac tgtgccttct agttgccagc catctgttgt ttgcccctcc
3361 cccgtgcctt ccttgaccct ggaaggtgcc actcccactg tcctttccta ataaaatgag
3421 gaaattgcat cgcattgtct gagtaggtgt cattctattc tggggggtgg ggtggggcag
3481 gacagcaagg gggaggattg ggaagacaat agcaggcatg ctggggagag atcgatctga
3541 ggaaccccta gtgatggagt tggccactcc ctctctgcgc gctcgctcgc tcactgaggc
3601 cgggcgacca aaggtcgccc gacgcccggg ctttgcccgg gcggcctcag tgagcgagcg
3661 agcgcgcaga gagggagtgg cccccccccc cccccccccg gcgattctct tgtttgctcc
3721 agactctcag gcaatgacct gatagccttt gtagagacct ctcaaaaata gctaccctct
3781 ccggcatgaa tttatcagct agaacggttg aatatcatat tgatggtgat ttgactgtct
3841 ccggcctttc tcacccgttt gaatctttac ctacacatta ctcaggcatt gcatttaaaa
3901 tatatgaggg ttctaaaaat ttttatcctt gcgttgaaat aaaggcttct cccgcaaaag
3961 tattacaggg tcataatgtt tttggtacaa ccgatttagc tttatgctct gaggctttat
4021 tgcttaatttt tgctaattct ttgccttgcc tgtatgattt attggatgtt ggaatcgcct
4081 gatgcggtat tttctcctta cgcatctgtg cggtatttca caccgcatat ggtgcactct
4141 cagtacaatc tgctctgatg ccgcatagtt aagccagccc cgacacccgc caacacccgc
4201 tgacgcgccc tgacgggctt gtctgctccc ggcatccgct tacagacaag ctgtgaccgt
4261 ctccgggagc tgcatgtgtc agaggttttc accgtcatca ccgaaacgcg cgagacgaaa
4321 gggcctcgtg atacgcctat ttttataggt taatgtcatg ataataatgg tttcttagac
4381 gtcaggtggc acttttcggg gaaatgtgcg cggaacccct atttgtttat ttttctaaat
4441 acattcaaat atgtatccgc tcatgagaca ataaccctga taaatgcttc aataatattg
4501 aaaaaggaag agtatgagta ttcaacattt ccgtgtcgcc cttattccct ttttgcggc
4561 attttgcctt cctgtttttg ctcacccaga aacgctggtg aaagtaaaag atgctgaaga
4621 tcagttgggt gcacgagtgg gttacatcga actggatctc aacagcggta agatccttga
4681 gagttttcgc cccgaagaac gttttccaat gatgagcact tttaaagttc tgctatgtgg
4741 cgcggtatta tcccgtattg acgccgggca agagcaactc ggtcgccgca tacactattc
4801 tcagaatgac ttggttgagt actcaccagt cacagaaaag catcttacgg atggcatgac
4861 agtaagagaa ttatgcagtg ctgccataac catgagtgat aacactgcgg ccaacttact
4921 tctgacaacg atcggaggac cgaaggagct aaccgctttt ttgcacaaca tgggggatca
4981 tgtaactcgc cttgatcgtt gggaaccgga gctgaatgaa gccataccaa acgacgagcg
5041 tgacaccacg atgcctgtag caatggcaac aacgttgcgc aaactattaa ctggcgaact
5101 acttactcta gcttcccggc aacaattaat agactggatg gaggcggata aagttgcagg
5161 accacttctg cgctcggccc ttccggctgg ctggtttatt gctgataaat ctggagccgg
5221 tgagcgtggg tctcgcggta tcattgcagc actggggcca gatggtaagc cctcccgtat
5281 cgtagttatc tacacgacgg ggagtcaggc aactatggat gaacgaaata gacagatcgc
5341 tgagataggt gcctcactga ttaagcattg gtaactgtca gaccaagttt actcatatat
5401 actttagatt gatttaaaac ttcatttta atttaaaagg atctaggtga agatccttt
5461 tgataatctc atgaccaaaa tcccttaacg tgagttttcg ttccactgag cgtcagaccc
5521 cgtagaaaag atcaaaggat cttcttgaga tcctttttt ctgcgcgtaa tctgctgctt
5581 gcaaacaaaa aaaccaccgc taccagcggt ggtttgtttg ccggatcaag agctaccaac
5641 tcttttccg aaggtaactg gcttcagcag agcgcagata ccaaatactg tccttctagt
5701 gtagccgtag ttaggccacc acttcaagaa ctctgtagca ccgcctacat acctcgctct
5761 gctaatcctg ttaccagtgg ctgctgccag tggcgataag tcgtgtctta ccgggttgga
5821 ctcaagacga tagttaccgg ataaggcgca gcggtcgggc tgaacggggg gttcgtgcac
5881 acagcccagc ttggagcgaa cgacctacac cgaactgaga tacctacagc gtgagctatg
5941 agaaagcgcc acgcttcccg aagggagaaa ggcggacagg tatccggtaa gcggcagggt
6001 cggaacagga gagcgcacga gggagcttcc agggggaaac gcctggtatc tttatagtcc
6061 tgtcgggttt cgccacctct gacttgagcg tcgatttttg tgatgctcgt caggggggcg
6121 gagcctatgg aaaaacgcca gcaacgcggc ctttttacgg ttcctggcct tttgctggcc
6181 ttttgctcac atgttctttc ctgcgttatc ccctgattct gtggataacc gtattaccgc
6241 ctttgagtga gctgataccg ctcgccgcag ccgaacgacc gagcgcagcg agtcagtgag
6301 cgaggaagcg gaagagc
```

DELIVERY OF MECP2 POLYNUCLEOTIDE USING RECOMBINANT AAV9

The present application is a continuation-in-part of U.S. patent application Ser. No. 13/270,840 filed Oct. 11, 2011. U.S. patent application Ser. No. 13/270,840 is a continuation of U.S. patent application Ser. No. 13/035,777 filed Feb. 25, 2011. U.S. patent application Ser. No. 13/035,777 claims the benefit of priority of U.S. Provisional Application No. 61/308,884, filed Feb. 26, 2010, and is also a continuation-in-part of International Patent Application No. PCT/US09/68818, filed Dec. 18, 2009. International Patent Application No. PCT/US09/68818 claims the benefit of priority of U.S. Provisional Application 61/139,470, filed Dec. 19, 2008. The present application also claims the benefit of priority of U.S. Provisional Patent Application No. 61/678,458 filed Aug. 1, 2012.

STATEMENT OF GOVERNMENT INTEREST

This invention was made with Government support under R21EY018491 awarded by the National Institutes of Health (NIH)/National Eye Institute (NEI), under R21NS064328, awarded by the NIH/National Institute of Neurological Disorders and Stroke (NINDS) and under RC2 NS69476-01 awarded by the National Institutes of Health (NIH). The Government has certain rights in the invention.

INCORPORATION BY REFERENCE OF THE SEQUENCE LISTING

This application contains, as a separate part of disclosure, a Sequence Listing in computer-readable form (filename: 44125CIP_SubSeqListing.txt; 21,551 bytes; created Jun. 4, 2014—ASCII text file) which is incorporated by reference herein in its entirety.

FIELD OF THE INVENTION

The present invention relates to Adeno-associated virus 9 methods and materials useful for systemically delivering polynucleotides across the blood brain barrier. Accordingly, the present invention also relates to methods and materials useful for systemically delivering polynucleotides to the central and peripheral nervous systems. The present invention also relates to Adeno-associated virus type 9 methods and materials useful for intrathecal delivery (i.e., delivery into the space under the arachnoid membrane of the brain or spinal cord) of polynucleotides. Use of the methods and materials is indicated, for example, for treatment of lower motor neuron diseases such as spinal muscle atrophy and amyotrophic lateral sclerosis as well as Pompe disease and lysosomal storage disorders. Use of the methods and materials is also indicated, for example, for treatment of Rett syndrome.

BACKGROUND

Large-molecule drugs do not cross the blood-brain-barrier (BBB) and 98% of small-molecules cannot penetrate this barrier, thereby limiting drug development efforts for many CNS disorders [Pardridge, W. M. *Nat Rev Drug Discov* 1: 131-139 (2002)]. Gene delivery has recently been proposed as a method to bypass the BBB [Kaspar, et al., *Science* 301: 839-842 (2003)]; however, widespread delivery to the brain and spinal cord has been challenging. The development of successful gene therapies for motor neuron disease will likely require widespread transduction within the spinal cord and motor cortex. Two of the most common motor neuron diseases are spinal muscular atrophy (SMA) and amyotrophic lateral sclerosis (ALS), both debilitating disorders of children and adults, respectively, with no effective therapies to date. Recent work in rodent models of SMA and ALS involves gene delivery using viruses that are retrogradely transported following intramuscular injection [Kaspar et al., *Science* 301: 839-842 (2003); Azzouz et al., *J Clin Invest* 114: 1726-1731 (2004); Azzouz et al., *Nature* 429: 413-417 (2004); Ralph et al., *Nat Med* 11: 429-433 (2005)]. However, clinical development may be difficult given the numerous injections required to target the widespread region of neurodegeneration throughout the spinal cord, brainstem and motor cortex to effectively treat these diseases. Adeno-associated virus (AAV) vectors have also been used in a number of recent clinical trials for neurological disorders, demonstrating sustained transgene expression, a relatively safe profile, and promising functional responses, yet have required surgical intraparenchymal injections [Kaplitt et al., *Lancet* 369: 2097-2105 (2007); Marks et al., *Lancet Neurol* 7: 400-408 (2008); Worgall et al., *Hum Gene Ther* (2008)].

SMA is an early pediatric neurodegenerative disorder characterized by flaccid paralysis within the first six months of life. In the most severe cases of the disease, paralysis leads to respiratory failure and death usually by two years of age. SMA is the second most common pediatric autosomal recessive disorder behind cystic fibrosis with an incidence of 1 in 6000 live births. SMA is a genetic disorder characterized by the loss of lower motor neurons (LMNs) residing along the length of the entire spinal cord. SMA is caused by a reduction in the expression of the survival motor neuron (SMN) protein that results in denervation of skeletal muscle and significant muscle atrophy. SMN is a ubiquitously expressed protein that functions in U snRNP biogenesis.

In humans there are two very similar copies of the SMN gene termed SMN1 and SMN2. The amino acid sequence encoded by the two genes is identical. However, there is a single, silent nucleotide change in SMN2 in exon 7 that results in exon 7 being excluded in 80-90% of transcripts from SMN2. The resulting truncated protein, called SMNΔ7, is less stable and rapidly degraded. The remaining 10-20% of transcript from SMN2 encodes the full length SMN protein. Disease results when all copies of SMN1 are lost, leaving only SMN2 to generate full length SMN protein. Accordingly, SMN2 acts as a phenotypic modifier in SMA in that patients with a higher SMN2 copy number generally exhibit later onset and less severe disease.

To date, there are no effective therapies for SMA. Therapeutic approaches have mainly focused on developing drugs for increasing SMN levels or enhancing residual SMN function. Despite years of screening, no drugs have been fully effective for increasing SMN levels as a restorative therapy. A number of mouse models have been developed for SMA. See, Hsieh-Li et al., *Nature Genetics*, 24 (1): 66-70 (2000); Le et al., *Hum. Mol. Genet.*, 14 (6): 845-857 (2005); Monani et al., *J. Cell. Biol.*, 160 (1): 41-52 (2003) and Monani et al., *Hum. Mol. Genet.*, 9 (3): 333-339 (2000). A recent study express a full length SMN cDNA in a mouse model and the authors concluded that expression of SMN in neurons can have a significant impact on symptoms of SMA. See Gavrilina et al., *Hum. Mol. Genet.*, 17(8):1063-1075 (2008).

ALS is another disease that results in loss of muscle and/or muscle function. First characterized by Charcot in 1869, it is a prevalent, adult-onset neurodegenerative disease affecting nearly 5 out of 100,000 individuals. ALS occurs when specific nerve cells in the brain and spinal cord that control voluntary movement gradually degenerate. Within two to five years after clinical onset, the loss of these motor neurons leads to progressive atrophy of skeletal muscles, which results in loss of muscular function resulting in paralysis, speech deficits, and death due to respiratory failure.

The genetic defects that cause or predispose ALS onset are unknown, although missense mutations in the SOD-1 gene occurs in approximately 10% of familial ALS cases, of which up to 20% have mutations in the gene encoding Cu/Zn superoxide dismutase (SOD1), located on chromosome 21. SOD-1 normally functions in the regulation of oxidative stress by conversion of free radical superoxide anions to hydrogen peroxide and molecular oxygen. To date, over 90 mutations have been identified spanning all exons of the SOD-1 gene. Some of these mutations have been used to generate lines of transgenic mice expressing mutant human SOD-1 to model the progressive motor neuron disease and pathogenesis of ALS.

De novo mutations in the X-linked gene encoding the transcription factor, Methyl-CpG binding protein 2 (MECP2), are the most frequent cause of the neurological disorder Rett syndrome (RTT). Hemizygous males usually die of neonatal encephalopathy. Heterozygous females survive into adulthood but exhibit severe symptoms including microcephaly, loss of purposeful hand motions and speech, and motor abnormalities which appear following a period of apparently normal development. Both male and female mouse models exhibit RTT-like behaviors [Guy et al., *Nature Genetics*, 27: 322-326 (2001); Chen et al., *Nature Genetics* 27: 327-331 (2001); and Katz et al., 5: 733-745 (2012)], but most studies have focused on males because of the shorter latency to and severity in symptoms. Despite encouraging studies on male mice, no therapeutic treatment has been shown yet to be effective in females, the more gender appropriate model.

AAV is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11. AAV9 is described in U.S. Pat. No. 7,198,951 and in Gao et al., *J. Virol.*, 78: 6381-6388 (2004). Advances in the delivery of AAV6 and AAV8 have made possible the transduction by these serotypes of skeletal and cardiac muscle following simple systemic intravenous or intraperitoneal injections. See Pacak et al., *Circ. Res.*, 99(4): 3-9 (1006) and Wang et al., *Nature Biotech.*, 23(3): 321-8 (2005). The use of AAV to target cell types within the central nervous system, though, has required surgical intraparenchymal injection. See, Kaplitt et al., supra; Marks et al., supra and Worgall et al., supra.

There thus remains a need in the art for methods and vectors for delivering genes across the BBB.

SUMMARY

The present invention provides methods and materials useful for systemically delivering polynucleotides across the BBB. The present invention also provides methods and materials useful for intrathecal delivery of polynucleotides to the central nervous system.

In one aspect, the invention provides methods of delivering a polynucleotide across the BBB comprising systemically administering a recombinant AAV9 (rAAV9) with a genome including the polynucleotide to a patient. In some embodiments, the rAAV9 genome is a self complementary genome. In other embodiments, the rAAV9 genome is a single-stranded genome.

In some embodiments, the methods systemically deliver polynucleotides across the BBB to the central and/or peripheral nervous system. Accordingly, a method is provided of delivering a polynucleotide to the central nervous system comprising systemically administering a rAAV9 with a self-complementary genome including the genome to a patient. In some embodiments, the polynucleotide is delivered to brain. In some embodiments, the polynucleotide is delivered to the spinal cord. Also provided is a method of delivering a polynucleotide to the peripheral nervous system comprising systemically administering a rAAV9 with a self-complementary genome including the polynucleotide to a patient is provided. In some embodiments, the polynucleotide is delivered to a lower motor neuron.

In another aspect, the invention provides methods of delivering a polynucleotide to the central nervous system of a patient in need thereof comprising intrathecal delivery of rAAV9 with a genome including the polynucleotide. In some embodiments, rAAV9 genome is a self-complementary genome. In some embodiments, a non-ionic, low-osmolar contrast agent is also delivered to the patient, for example, iobitridol, iohexol, iomeprol, iopamidol, iopentol, iopromide, ioversol or ioxilan.

Embodiments of the invention employ rAAV9 to deliver polynucleotides to nerve and glial cells. In some aspects, the glial cell is a microglial cell, an oligodendrocyte or an astrocyte. In other aspects the rAAV9 is used to deliver a polynucleotide to a Schwann cell.

Use of the systemic or intrathecal delivery methods is indicated, for example, for lower motor neuron diseases such as SMA and ALS as well as Pompe disease, lysosomal storage disorders, Glioblastoma multiforme and Parkinson's disease. Lysosomal storage disorders include, but are not limited to, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (Type I, Type II, Type III), GM1 gangliosidosis (Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (Infantile Onset, Late Onset), Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (Type A, Type B, Type C), Neuronal Ceroid Lipofuscinoses (CLN6 disease (Atypical Late Infantile, Late Onset variant, Early Juvenile), Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis, Pompe disease/Glycogen storage disease type II, Pycnodysostosis, Sandhoff Disease/Adult Onset/GM2 Gangliosidosis, Sandhoff Disease/GM2 gangliosidosis—Infantile, Sandhoff Disease/GM2 gangliosidosis—Juvenile, Schindler disease, Salla disease/Sialic Acid Storage Disease, Tay-Sachs/GM2 gangliosidosis, Wolman disease.

In further embodiments, use of the systemic or intrathecal delivery methods is indicated for treatment of nervous system disease such as Rett Syndrome, Alzheimer's Disease, Parkinson's Disease, Huntington's Disease along with nervous system injury including spinal cord and brain trauma/injury, stroke, and brain cancers. In some embodiments, methods of treatment of Rett syndrome are contemplated where the methods deliver a polynucleotide to the central nervous system of a patient in need thereof by systemic delivery of rAAV9 with a genome including the polynucleotide. In some embodiments, methods of treatment of Rett syndrome are contemplated where the methods deliver a polynucleotide to the central nervous system of a patient in need thereof by intrathecal delivery of rAAV9 with a genome including the polynucleotide.

In yet another aspect, the invention provides rAAV genomes. The rAAV genomes comprise one or more AAV ITRs flanking a polynucleotide encoding a polypeptide (including, but not limited to, an SMN polypeptide) or encoding short hairpin RNAs directed at mutated proteins or control sequences of their genes. The polynucleotide is operatively linked to transcriptional control DNAs, specifically promoter DNA and polyadenylation signal sequence DNA that are functional in target cells to form a gene cassette. The gene cassette may also include intron sequences to facilitate processing of an RNA transcript when expressed in mammalian cells.

In some aspects, the rAAV9 genome encodes a trophic or protective factor. In various embodiments, use of a trophic or protective factor is indicated for neurodegenerative disorders contemplated herein, including but not limited to Alzheimer's Disease, Parkinson's Disease, Huntington's Disease along with nervous system injury including spinal cord and brain trauma/injury, stroke, and brain cancers. Non-limiting examples of known nervous system growth factors include nerve growth factor (NGF), brain-derived neurotrophic factor (BDNF), neurotrophin-3 (NT-3), neurotrophin-4/5 (NT-4/5), neurotrophin-6 (NT-6), ciliary neurotrophic factor (CNTF), glial cell line-derived neurotrophic factor (GDNF), the fibroblast growth factor family (e.g., FGF's 1-15), leukemia inhibitory factor (LIF), certain members of the insulin-like growth factor family (e.g., IGF-1), the neurturins, persephin, the bone morphogenic proteins (BMPs), the immunophilins, the transforming growth factor (TGF) family of growth factors, the neuregulins, epidermal growth factor (EGF), platelet-derived growth factor (PDGF), vascular endothelial growth factor family (e.g. VEGF 165), follistatin, Hif1, and others. Also generally contemplated are zinc finger transcription factors that regulate each of the trophic or protective factors contemplated herein. In further embodiments, methods to modulate neuro-immune function are contemplated, including but not limited to, inhibition of microglial and astroglial activation through, for example, NFkB inhibition, or NFkB for neuroprotection (dual action of NFkB and associated pathways in different cell types) by siRNA, shRNA, antisense, or miRNA. In still further embodiments, the rAAV9 genome encodes an apoptotic inhibitor (e.g., bcl2, bclxL). Use of a rAAV9 encoding a trophic factor or spinal cord injury modulating protein or a suppressor of an inhibitor of axonal growth (e.g., a suppressor of Nogo [Oertle et al., The Journal of Neuroscience, 23(13):5393-5406 (2003)] is also contemplated for treating spinal cord injury.

In some embodiments, use of materials and methods of the invention is indicated for neurodegenerative disorders such as Parkinson's disease. In various embodiments, the rAAV9 genome may encode, for example, Aromatic acid dopa decarboxylase (AADC), Tyrosine hydroxylase, GTP-cyclohydrolase 1 (gtpch1), apoptotic inhibitors (e.g., bcl2, bclxL), glial cell line-derived neurotrophic factor (GDNF), the inhibitory neurotransmitter-amino butyric acid (GABA), and enzymes involved in dopamine biosynthesis. In further embodiments, the rAAV9 genome may encode, for example, modifiers of Parkin and/or synuclein.

In some embodiments, use of materials and methods of the invention is indicated for neurodegenerative disorders such as Alzheimer's disease. In further embodiments, methods to increase acetylcholine production are contemplated. In still further embodiments, methods of increasing the level of a choline acetyltransferase (ChAT) or inhibiting the activity of an acetylcholine esterase (AchE) are contemplated.

In some embodiments, the rAAV9 genome may encode, for example, methods to decrease mutant Huntington protein (htt) expression through siRNA, shRNA, antisense, and/or miRNA for treating a neurodegenerative disorder such as Huntington's disease.

In some embodiments, use of materials and methods of the invention is indicated for neurodegenerative disorders such as ALS. In some aspects, treatment with the embodiments contemplated by the invention results in a decrease in the expression of molecular markers of disease, such as TNFα, nitric oxide, peroxynitrite, and/or nitric oxide synthase (NOS).

In other aspects, the vectors could encode short hairpin RNAs directed at mutated proteins such as superoxide dismutase for ALS, or neurotrophic factors such as GDNF or IGF1 for ALS or Parkinson's disease.

In some embodiments, use of materials and methods of the invention is indicated for preventing or treating neurodevelopmental disorders such as Rett Syndrome. For embodiments relating to Rett Syndrome, the rAAV9 genome may encode, for example, methyl cytosine binding protein 2 (MECP2).

The rAAV genomes of the invention lack AAV rep and cap DNA. AAV DNA in the rAAV genomes (e.g., ITRs) may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC_001401 and Srivastava et al., *J. Virol.*, 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., *J. Virol.*, 78: 6381-6388 (2004); the AAV-10 genome is provided in *Mol. Ther.*, 13(1): 67-76 (2006); and the AAV-11 genome is provided in *Virology*, 330(2): 375-383 (2004).

In another aspect, the invention provides DNA plasmids comprising rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety. In various embodiments, AAV capsid proteins may be modified to enhance delivery of the recombinant vector. Modifications to capsid proteins are generally known in the art. See, for example, US 20050053922 and US 20090202490, the disclosures of which are incorporated by reference herein in their entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259: 4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. No. 5,786,211; U.S. Pat. No. 5,871,982; and U.S. Pat. No. 6,258,595. Single-stranded rAAV are specifically contemplated. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

In still another aspect, the invention provides rAAV (i.e., infectious encapsidated rAAV particles) comprising a rAAV genome of the invention. In some embodiments, the rAAV genome is a self-complementary genome.

In some embodiments, the invention includes, but is not limited to, the exemplified rAAV named "rAAV SMN." The rAAV SMN genome has in sequence an AAV2 ITR, the chicken β-actin promoter with a cytomegalovirus enhancer, an SV40 intron, the SMN coding DNA set out in SEQ ID NO: 1 (GenBank Accession Number NM_000344.2), a polyadenylation signal sequence from bovine growth hormone and another AAV2 ITR. Conservative nucleotide substitutions of SMN DNA are also contemplated (e.g., a guanine to adenine change at position 625 of GenBank Accession Number NM_000344.2). The genome lacks AAV rep and cap DNA, that is, there is no AAV rep or cap DNA between the ITRs of the genome. SMN polypeptides contemplated include, but are not limited to, the human SMN1 polypeptide set out in NCBI protein database number NP_000335.1. Also contemplated is the SMN1-modifier polypeptide plastin-3 (PLS3) [Oprea et al., *Science* 320(5875): 524-527 (2008)]. Sequences encoding other polypeptides may be substituted for the SMN DNA.

Other rAAV9 are provided such as a rAAV9 named "scAAV9 MECP2." Its genome has in sequence an AAV2 ITR missing the terminal resolution site, an approximately 730 bp murine MECP2 promoter fragment, SV40 intron sequences, murine MECP2 coding sequences, a bovine growth hormone polyadenylation signal sequence and an AAV2 ITR. The scAAV9 MECP2 genome lacks AAV rep and cap DNA, that is, there is no AAV rep or cap DNA between the ITRs of the genome. Yet another rAAV9 provided is a rAAV9 named "scAAV9 hMECP2." Its genome has in sequence an AAV2 ITR missing the terminal resolution site, an approximately 730 bp murine MECP2 promoter fragment, SV40 intron sequences, human MECP2α coding sequences, a bovine growth hormone polyadenylation signal sequence and an AAV2 ITR. The scAAV9 hMECP2 genome lacks AAV rep and cap DNA, that is, there is no AAV rep or cap DNA between the ITRs of the genome. Substitution of human MECP2 promoter sequences for the corresponding murine MECP2 promoter sequences is specifically contemplated.

The rAAV of the invention may be purified by methods standard in the art such as by column chromatography or cesium chloride gradients. Methods for purifying rAAV vectors from helper virus are known in the art and include methods disclosed in, for example, Clark et al., *Hum. Gene Ther.*, 10(6): 1031-1039 (1999); Schenpp and Clark, *Methods Mol. Med.*, 69 427-443 (2002); U.S. Pat. No. 6,566,118 and WO 98/09657.

In another aspect, the invention contemplates compositions comprising rAAV of the present invention. In one embodiment, compositions of the invention comprise a rAAV encoding a SMN polypeptide. In another embodiment, compositions of the invention comprise a rAAV encoding a MECP2 polypeptide. In other embodiments, compositions of the present invention may include two or more rAAV encoding different polypeptides of interest.

Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). Dosages may also vary based on the timing of the administration to a human. These dosages of rAAV may range from about $1\times10^{11}$ vg/kg, about $1\times10^{12}$, about $1\times10^{13}$, about $1\times10^{14}$, about $1\times10^{15}$, about $1\times10^{16}$ or more viral genomes per kilogram body weight in an adult. For a neonate, the dosages of rAAV may range from about $1\times10^{11}$, about $1\times10^{12}$, about $3\times10^{12}$, about $1\times10^{13}$, about $3\times10^{13}$, about $1\times10^{14}$, about $3\times10^{14}$, about $1\times10^{15}$, about $3\times10^{15}$, about $1\times10^{16}$, about $3\times10^{16}$ or more viral genomes per kilogram body weight.

Methods of transducing nerve or glial target cells with rAAV are contemplated by the invention. The methods comprise the step of administering an intravenous or intrathecal effective dose, or effective multiple doses, of a composition comprising a rAAV of the invention to an animal (including a human being) in need thereof. If the dose is administered prior to development of a disorder/disease, the administration is prophylactic. If the dose is administered after the development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. Examples of disease states contemplated for treatment by methods of the invention are listed herein above.

Combination therapies are also contemplated by the invention. Combination as used herein includes both simultaneous treatment or sequential treatments. Combinations of methods of the invention with standard medical treatments (e.g., riluzole in ALS) are specifically contemplated, as are combinations with novel therapies.

Route(s) of administration and serotype(s) of AAV components of rAAV (in particular, the AAV ITRs and capsid protein) of the invention may be chosen and/or matched by those skilled in the art taking into account the infection and/or disease state being treated and the target cells/tissue(s).

In some embodiments, administration of the rAAV9 to the patient is contemplated to occur at postnatal day 1 (P1). In some embodiments, administration is contemplated to occur at P2, P3, P4, P5, P6, P7, P8, P9, P10, P11, P12, P13, P14, P15, P16, P17, P18, P19, P20, P21, P22, P23, P24, P25, P26, P27, P28, P29, P30, P31, P32, P33, P34, P35, P36, P37, P38, P39, P40, P41, P42, P43, P44, P45, P46, P47, P48, P49, P50, P51, P52, P53, P54, P55, P56, P57, P58, P59, P60, P61, P62, P63, P64, P65, P66, P67, P68, P69, P70, P71, P72, P73, P74, P75, P76, P77, P78, P79, P80, P81, P82, P83, P84, P85, P86, P87, P88, P89, P90, P91, P92, P93, P94, P95, P96, P97, P98, P99, P100, P110, P120, P130, P140, P150, P160, P170, P180, P190, P200, P250, P300, P350, 1 year, 1.5 years, 2 years, 2.5 years, 3 years or older. While delivery to an individual in need thereof after birth is contemplated, intrauteral delivery and delivery to the mother are also contemplated.

Compositions suitable for systemic or intrathecal use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin, and Tween family of products (e.g., Tween 20).

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction with rAAV may also be carried out in vitro. In one embodiment, desired target cells are removed from the subject, transduced with rAAV and reintroduced into the subject. Alternatively, syngeneic or xenogeneic cells can be used where those cells will not generate an inappropriate immune response in the subject.

Suitable methods for the transduction and reintroduction of transduced cells into a subject are known in the art. In one embodiment, cells can be transduced in vitro by combining rAAV with the cells, e.g., in appropriate media, and screening for those cells harboring the DNA of interest using conventional techniques such as Southern blots and/or PCR, or by using selectable markers. Transduced cells can then be formulated into pharmaceutical compositions, and the composition introduced into the subject by various techniques, such as by injection into the spinal cord.

Transduction of cells with rAAV of the invention results in sustained expression of polypeptide. The present invention thus provides methods of administering/delivering rAAV (e.g., encoding SMN protein or MECP2 protein) of the invention to an animal or a human patient. These methods include transducing nerve and/or glial cells with one or more rAAV of the present invention.

Transduction may also be carried out with gene cassettes comprising tissue specific control elements. For example, promoters that allow expression specifically within neurons or specifically within astrocytes. Examples include neuron specific enolase and glial fibrillary acidic protein promoters. Inducible promoters under the control of an ingested drug may also be developed (e.g., rapamycin). By way of non-limiting example, it is understood that systems such as the tetracycline (TET on/off) system [see, for example, Urlinger et al., *Proc. Natl. Acad. Sci. USA* 97(14):7963-7968 (2000) for recent improvements to the TET system] and Ecdysone receptor regulatable system [Palli et al., *Eur J. Biochem* 270: 1308-1315 (2003] may be utilized to provide inducible polynucleotide expression. It will also be understood by the skilled artisan that combinations of any of the methods and materials contemplated herein may be used for treating a neurodegenerative disease.

The term "transduction" is used to refer to the administration/delivery of a polynucleotide (e.g., SMN DNA or MECP2 DNA) to a recipient cell either in vivo or in vitro, via a replication-deficient rAAV of the invention resulting in expression of a functional polypeptide (e.g., SMN or MECP2) by the recipient cell.

Thus, the invention provides methods of administering an effective dose (or doses, administered essentially simultaneously or doses given at intervals) of rAAV of the invention to a patient in need thereof.

In still another aspect, methods of the invention may be used to deliver polynucleotides to a vascular endothelial cell rather than across the BBB.

MeCP2 (n=8), scAAV9/Control (n=5). Mecp2$^{+/+}$ (n=8). *P<0.05, P<0.01, *P<0.001 and ns=not significant by one way ANOVA (Newman-Keuls multiple comparison test for panel c and one way ANOVA (Dunn's multiple comparison test for panels d-f. Data are means±s.e.m.

Figure 21:
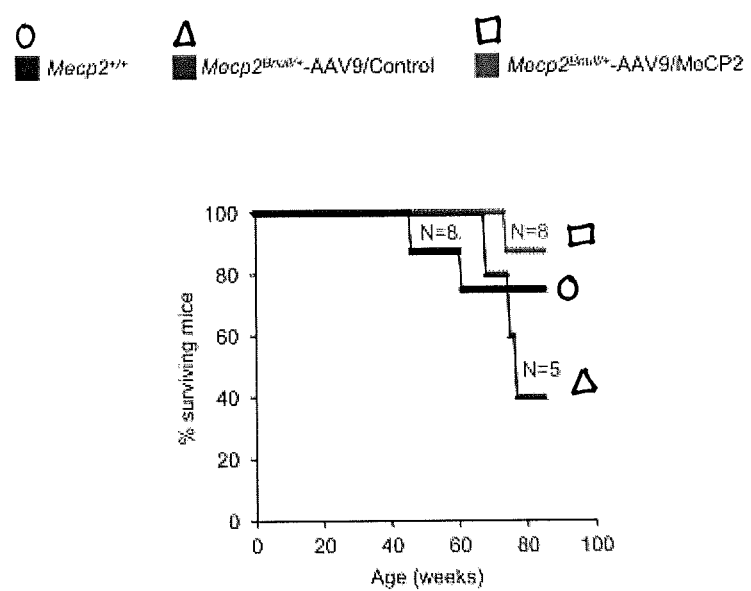

FIG. 21 is a Kaplan-Meier survival curve showing that Mecp2$^{Bnull/+}$ mice injected with scAAV9/MECP2 do not die prematurely compared to non-injected Mecp2$^{+/+}$ mice. P>0.05 by Gehan-Breslow-Wilcoxon test.

FIG. 22 shows the sequence of the genome of the exemplary rAAV9 named "scAAV9 MECP2" (SEQ ID NO: 13). Its genome has in sequence an AAV2 ITR missing the terminal resolution site (nucleotides 662-767), an approximately 730 bp murine MECP2 promoter fragment (nucleotides 859-1597), SV40 late 19s and late 16s intron sequences (1602-1661), murine MECP2 coding sequences (nucleotides 1799-3304), a bovine growth hormone polyadenylation signal sequence (nucleotides 3388-3534) and an AAV2 ITR (nucleotides 3614-3754). The scAAV9 MECP2 genome lacks AAV rep and cap DNA, that is, there is no AAV rep or cap DNA between the ITRs of the genome.

FIG. 23 shows the sequence of the genome of the exemplary rAAV9 named "scAAV9 hMECP2" (SEQ ID NO: 14) Its genome has in sequence an AAV2 ITR missing the terminal resolution site (nucleotides 662-767), an approximately 730 bp murine MECP2 promoter fragment (nucleotides 859-1597), SV40 late 19s and late 16s intron sequences (nucleotides 1602-1661), human MECP2α coding sequences (nucleotides 1765-3261), a bovine growth hormone polyadenylation signal sequence (nucleotides 3314-3460) and an AAV2 ITR (nucleotides 3540-3680). The scAAV9 hMECP2 genome lacks AAV rep and cap DNA, that is, there is no AAV rep or cap DNA between the ITRs of the genome.

DETAILED DESCRIPTION

The present invention is illustrated by the following examples relating to a novel rAAV9 and its ability to efficiently deliver genes to the spinal cord via intravenous delivery in both neonatal animals and in adult mice. Example 1 describes experiments showing that rAAV9 can transduce and express protein in mouse skeletal muscle. Example 2 describes experiments in which the expression of the rAAV9 transgene was examined. Example 3 describes the ability of rAAV9 to transduce and express protein in lumbar motor neurons (LMNs). Example 4 describes the evaluation of vectors that do not require second-strand synthesis. Example 5 describes experiments focused on examining whether rAAV9 vectors were enhanced for retrograde transport to target dorsal root ganglion (DRG) and LMNs or could easily pass the blood-brain-barrier (BBB) in neonates. Example 6 describes the evaluation of optimal delivery of rAAV9 expressing SMN for postnatal gene replacement in a mouse model of Type 2 SMA for function and survival. Example 7 describes the examination of the brains of mice following postnatal day-one intravenous injection of scAAV9-CBGFP. Example 8 describes the investigation of whether astrocyte transduction is related to vector purity or delivery route. Example 9 describes administration of scAAV9-GFP in a nonhuman primate. Example 10 describes experiments demonstrating that self complementary rAAV9 bearing MECP2 cDNA under control of a fragment of its own promoter (scAAV9/MECP2), was capable of significantly stabilizing or reversing disease phenotypes when administered systemically into female RTT mouse models.

Example 1

The ability of AAV9 to target and express protein in skeletal muscle was evaluated in an in vivo model system.

Figure 1:
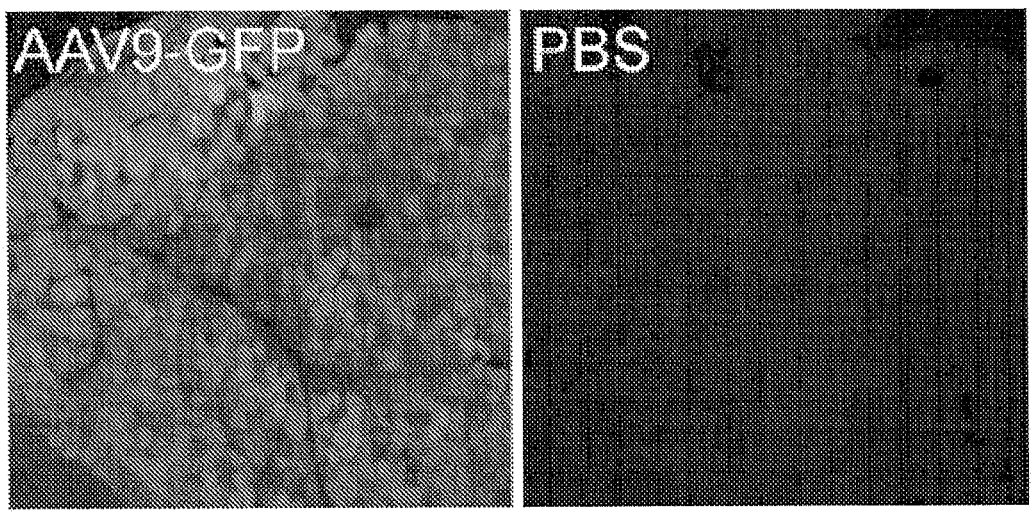
FIG. 1 depicts GFP expression in the gastrocnemius muscle of AAV9-GFP or PBS treated mice.

Intravenous administration of $1\times10^{11}$ particles of scAAV9-GFP was performed in a total volume of 50 µl to postnatal day 1 mice and the extent of muscle transduction was evaluated. The rAAV GFP genome included in sequence an AAV2 ITR, the chicken β-actin promoter with a cytomegalovirus enhancer, an SV40 intron, the GFP DNA, a polyadenylation signal sequence from bovine growth hormone and another AAV2 ITR. The ability of the AAV9 vectors to transduce skeletal muscle was evaluated using a GFP expressing vector. AAV9-GFP expressed at high levels in the skeletal muscles that were analyzed. Ten days following injections, animals were euthanized and gastrocnemius muscles were rapidly isolated, frozen using liquid nitrogen chilled isopentane, and sectioned on a cryostat at 15 µm. Analysis of muscle sections using a Zeiss Axiovert microscope equipped with GFP fluorescence demonstrated that AAV9-GFP expressed at very high levels, with over 90% of the analyzed gastrocnemius muscle transduced (FIG. 1). No GFP expression was detected in PBS control treated animals (FIG. 1). These results showed that AAV9 was effective at targeting and expressing in skeletal muscles.

Example 2

Transgene expression following intravenous injection in neonatal animals prior to the closure of the BBB and in adult animals was examined.

Mice used were C57Bl/6 littermates. The mother (singly housed) of each litter to be injected was removed from the cage. The postnatal day 1 (P1) pups were rested on a bed of ice for anesthetization. For neonate injections, a light microscope was used to visualize the temporal vein (located just anterior to the ear). Vector solution was drawn into a 3/10 cc 30 gauge insulin syringe. The needle was inserted into the vein and the plunger was manually depressed. Injections were in a total volume of 100 µl of a phosphate buffered saline (PBS) and virus solution. A total of $1\times10^{11}$ DNase resistant particles of scAAV9 CB GFP (Virapur LLC, San Diego) were injected. One-day-old wild-type mice received temporal vein injections of $1\times10^{11}$ particles of a self-complementary (sc) AAV9 vector [McCarty et al., Gene therapy, 10: 2112-2118 (2003)] that expressed green fluorescent protein (GFP) under control of the chicken-β-actin hybrid promoter (CB). A correct injection was verified by noting blanching of the vein. After the injection pups were returned to their cage. When the entire litter was injected, the pups were rubbed with bedding to prevent rejection by the mother. The mother was then reintroduced to the cage. Neonate animals were sacrificed ten days post injection, spinal cords and brains were extracted, rinsed in PBS, then immersion fixed in a 4% paraformaldehyde solution.

Adult tail vein injections were performed on ~70 day old C57Bl/6 mice. Mice were placed in restraint that positioned the mouse tail in a lighted, heated groove. The tail was swabbed with alcohol then injected intravenously with a 100 µl viral solution containing a mixture of PBS and $5\times10^{11}$ DNase resistant particles of scAAV9 CB GFP. After the injection, animals were returned to their cages. Two weeks post injection, animals were anesthetized then transcardially perfused first with 0.9% saline then 4% paraformaldehyde. Brains and spinal cords were harvested and immersion fixed in 4% paraformaldehyde for an additional 24-48 hours.

Neonate and adult brains were transferred from paraformaldehyde to a 30% sucrose solution for cryoprotection. The brains were mounted onto a sliding microtome with Tissue-Tek O.C.T. compound (Sakura Finetek USA, Torrance, Calif.) and frozen with dry ice. Forty micron thick sections were divided into 5 series for histological analysis. Tissues for immediate processing were placed in 0.01 M PBS in vials. Those for storage were placed in antifreeze solution and transferred to −20° C. Spinal cords were cut into blocks of tissue 5-6 mm in length, then cut into 40 micron thick transverse sections on a vibratome. Serial sections were kept in a 96 well plate that contained 4% paraformaldehyde and were stored at 4° C.

Brains and spinal cords were both stained as floating sections. Brains were stained in a 12-well dish, and spinal cords sections were stained in a 96-well plate to maintain their rostral-caudal sequence. Tissues were washed three times for 5 minutes each in PBS, then blocked in a solution containing 10% donkey serum and 1% Triton X-100 for two hours at room temperature. After blocking, antibodies were diluted in the blocking solution at 1:500. The primary antibodies used were as follows: goat anti-ChAT and mouse anti-NeuN (Chemicon), rabbit anti-GFP (Invitrogen) and guinea pig anti-GFAP (Advanced Immunochemical). Tissues were incubated in primary antibody at 4° C. for 48-72 hours then washed three times with PBS. After washing, tissues were incubated for 2 hours at room temperature in the appropriate secondary antibodies (1:125 Jackson Immunoresearch) with DAPI. Tissues were then washed three times with PBS, mounted onto slides then coverslipped. All images were captured on a Zeiss laser-scanning confocal microscope.

Figure 2:
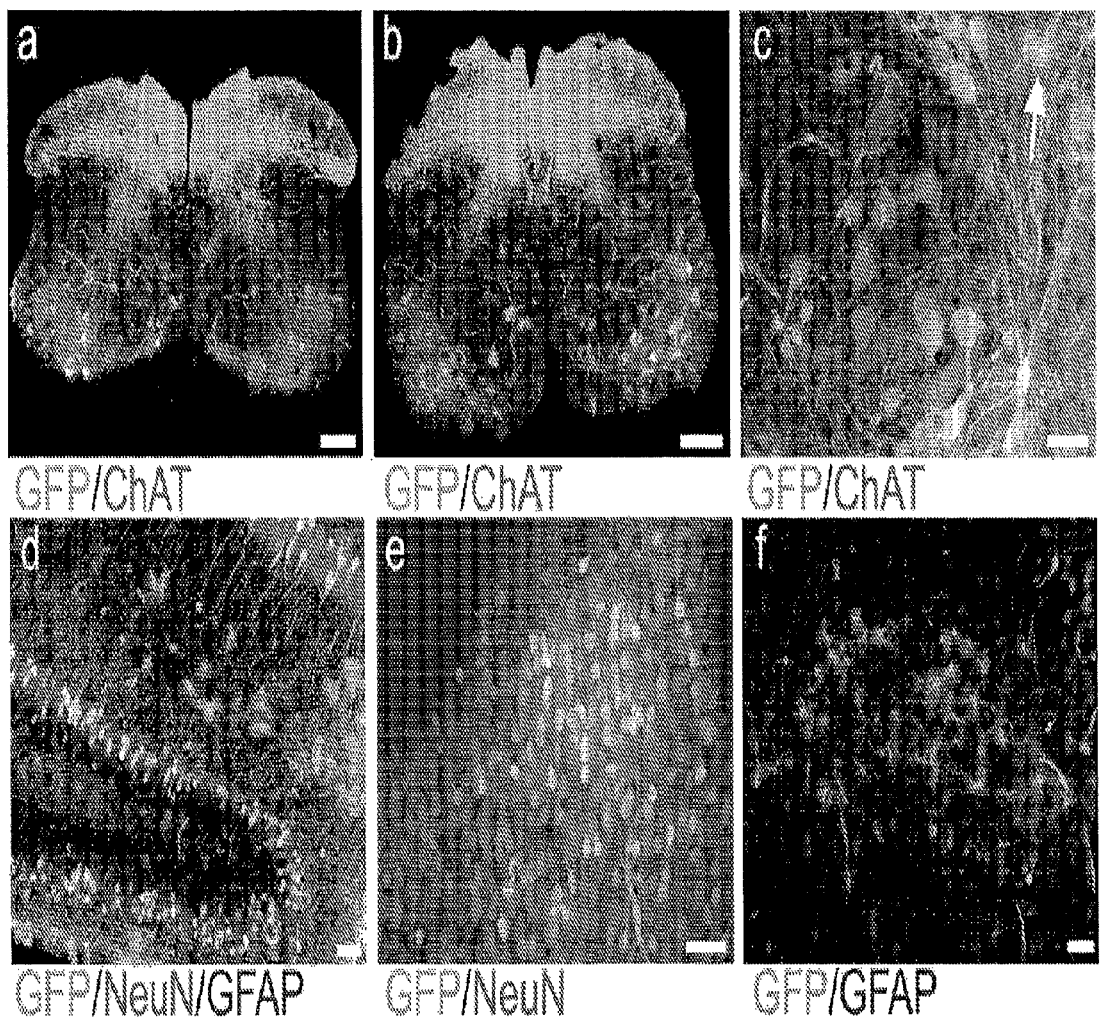
FIG. 2 depicts widespread neuron and astrocyte AAV9-GFP transduction in CNS and PNS 10-days-post-intravenous injection of P1 mice. (A-B) GFP and ChAT immunohistochemistry of cervical (A) and lumbar (B) spinal cord. (C) High-power magnification shows extensive co-localization of GFP and ChAT positive cells. (arrow indicates a GFP-positive astrocyte). (D) Neurons and astrocytes transduced in the hippocampus. (E) Pyramidal cells in the cortex were GFP positive. (F) Clusters of GFP positive astrocytes were observed throughout the brain. Scale bars (A-B) 200 µm, (C) 50 µm, (D-F) 50 µm.

Spinal cords had remarkable GFP expression throughout all levels with robust GFP expression in fibers that ascended in the dorsal columns and fibers that innervated the spinal gray matter, indicating dorsal root ganglia (DRG) transduction. GFP positive cells were also found in the ventral region of the spinal cord where lower motor neurons reside (FIG. 2A-B). Labeling of choline acetyl transferase (ChAT) positive cells with GFP demonstrated a large number of ChAT positive cells expressing GFP throughout all cervical and lumbar sections examined, indicating widespread LMN transduction (FIG. 2C). Approximately 56% of ChAT positive cells strongly expressed GFP in sections analyzed of the lumbar spinal cord (598 GFP+/1058 ChAT+, n=4) (Table 1, below). This is the highest proportion of LMNs transduced by a single injection of AAV reported. Stereology for total number of neurons in a given area and total number of GFP+ cells was performed on a Nikon E800 fluorescent microscope with computer-assisted microscopy and image analysis using StereoInvestigator software (MicroBrightField, Inc., Williston, Vt.) with the optical dissector principle to avoid oversampling errors and the Cavalieri estimation for volumetric measurements. Coronal 40 µm sections, 240 µm apart covering the regions of interest in its rostro-caudal extension was evaluated. The entire dentate gyrus, caudal retrosplenial/cingulate cortex; containing the most caudal extent of the dentate gyrus; extending medially to the subiculum and laterally to the occipital cortex, and the purkinje cell layer was sampled using ~15-25 optical dissectors in each case. Fluorescent microscopy using a 60× objective for NeuN and GFP were utilized and cells within the optical dissector were counted on a computer screen. Neuronal density and positive GFP density were calculated by multiplying the total volume to estimate the percent of neuronal transduction in each given area as previously described [Kempermann et al., *Proceedings of the National Academy of Sciences of the United States of America* 94: 10409-10414 (1997)].

For motor neuron quantification, serial 40 µm thick lumbar spinal cord sections, each separated by 480 µm, were labeled as described for GFP and ChAT expression. Stained sections were serially mounted on slides from rostral to caudal, then coverslipped. Sections were evaluated using confocal microscopy (Zeiss) with a 40× objective and simultaneous FITC and Cy3 filters. FITC was visualized through a 505-530 nm band pass filter to avoid contaminating the Cy3 channel. The total number of ChAT positive cells found in the ventral horns with defined soma was tallied by careful examination through the entire z-extent of the section. GFP labeled cells were quantified in the same manner, while checking for co-localization with ChAT. The total number of cells counted per animal ranged from approximately 150-366 cells per animal. For astrocyte quantification, as with motor neurons, serial sections were stained for GFP, GFAP and EAAT2, then mounted. Using confocal microscopy with a 63× objective and simultaneous FITC and Cy5 filters, random fields in the ventral horns of lumbar spinal cord sections from tail vein injected animals were selected. The total numbers of GFP and GFAP positive cells were counted from a minimum of at least 24-fields per animal while focusing through the entire z extent of the section.

In addition to widespread DRG and motor neuron transduction, GFP-positive glial cells were observed throughout the spinal gray matter (FIG. 2C; arrow). The brains were next examined following P1 intravenous injection of AAV9-CB-GFP and revealed extensive GFP expression in all regions analyzed, including the hippocampus (FIG. 2D), cortex (FIG. 2E), striatum, thalamus, hypothalamus and choroid plexus, with predominant neuronal transduction. However, transduced astrocytes were also found in all regions of the brain examined (FIG. 2F).

The remarkable pattern of GFP expression observed following P1 administration suggests two independent modes of viral entry into the central nervous system (CNS). Due to the ubiquitous GFP expression throughout the brain, the virus likely crossed the developing BBB. However the GFP expression pattern in the neonate spinal cord is defined with respect to the specific DRG and LMN transduction. The DRG and the LMN have projections into the periphery which suggests retrograde transport may be the mechanism of transduction. In support of retrograde transport as the method of spinal cord neuronal transduction, there were no GFP positive interneurons observed in any section examined. Alternatively, the virus may have a LMN tropism after crossing the BBB, but this appears unlikely as ChAT positive cells still migrating from the central canal to the ventral horn were largely untransduced (FIG. 2A-B).

TABLE 1

| | | Neonate | | |
|---|---|---|---|---|
| | | GFP (mean +/− s.e.m.) | NeuN (mean +/− s.e.m.) | % (mean +/− s.e.m.) |
| Brain | Retrosplenial/Cingulate | 142,658.30 +/− 11124.71 | 762,104.30 +/− 38397.81 | 18.84 +/− 1.93 |
| | Dentate Gyrus | 42,304.33 +/− 15613.33 | 278,043.70 +/− 11383.56 | 14.82 +/− 4.89 |
| | Purkinje cells | 52,720.33 +/− 1951.33 | 73,814.66 +/− 5220.80 | 71.88 +/− 3.65 |

TABLE 1-continued

|  |  | GFP (mean +/− s.e.m.) | ChAT (mean +/− s.e.m.) | % (mean +/− s.e.m.) |
|---|---|---|---|---|
| Lumbar spinal cord | 10 days post injection | 149.5 +/− 31.65 | 264.5 +/− 53.72 | 56.18 +/− 1.95 |
|  | 21 days post injection | 83.33 +/− 16.33 | 140.0 +/− 31.76 | 60.79 +/− 2.96 |

Adult

|  |  | GFP (mean +/− s.e.m.) | GFAP (mean +/− s.e.m.) | % (mean +/− s.e.m.) |
|---|---|---|---|---|
| Lumbar spinal cord (grey matter) | % GFP colabeled w/GFAP | 48.00 +/− 10.12 | 43.00 +/− 7.00 | 91.44 +/− 4.82 |
|  | % GFAP+ transduced | 41.33 +/− 5.55 | 64.33 +/− 8.67 | 64.23 +/− 0.96 |

Additional experiments were done on one-day-old wild-type mice where they were administered temporal vein injections of $4\times10^{11}$ particles of a self-complementary (sc) AAV9 vector [McCarty et al., Gene therapy 10: 2112-2118 (2003)] that expressed green fluorescent protein (GFP) under control of the chicken-β-actin hybrid promoter (CB).

Histological processing was performed as above. Brains and spinal cords were both stained as floating sections. Brains were stained in a 12-well dish, and spinal cords sections were stained in a 96-well plate to maintain their rostral-caudal sequence. Tissues were washed three-times for 5-minutes each in PBS, then blocked in a solution containing 10% donkey serum and 1% Triton X-100 for two hours at room temperature. After blocking, antibodies were diluted in the blocking solution at 1:500. The primary antibodies used were as follows: goat anti-ChAT and mouse anti-NeuN (Millipore, Billerica, Mass.), rabbit anti-GFP (Invitrogen, Carlsbad, Calif.), guinea pig anti-GFAP (Advanced Immunochemical, Long Beach, Calif.) and goat anti-GAD67 (Millipore, Billerica, Mass.). Tissues were incubated in primary antibody at 4° C. for 48-72 hours then washed three times with PBS. After washing, tissues were incubated for 2 hours at room temperature in the appropriate secondary antibodies (1:125 Jackson Immunoresearch, Westgrove, Pa.) with DAPI. Tissues were then washed three times with PBS, mounted onto slides then coverslipped. All images were captured on a Zeiss-laser-scanning confocal microscope.

Figure 3:
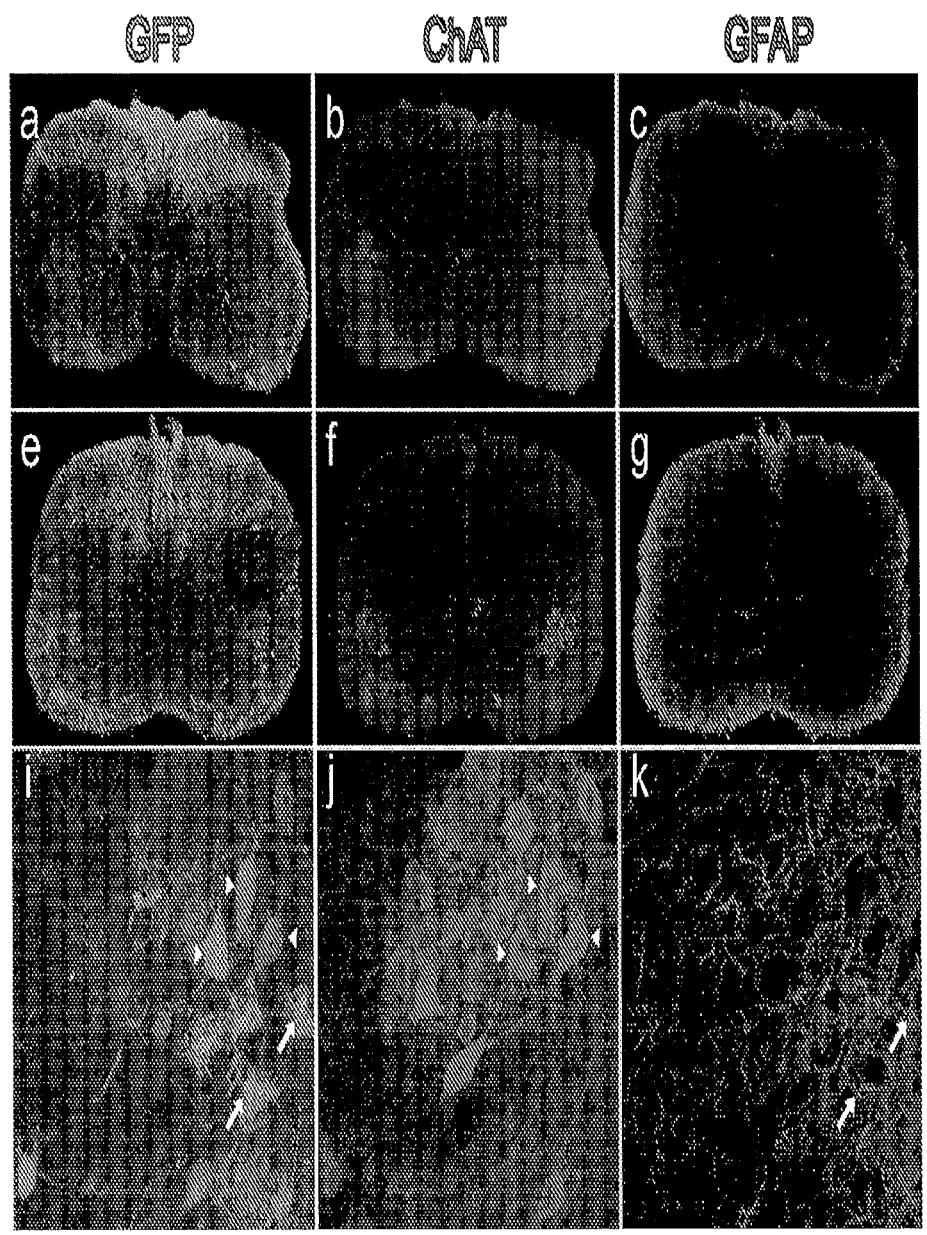
FIG. 3 shows that intravenous injection of AAV9 leads to widespread neonatal spinal cord transduction. Cervical (a-c) and lumbar (e-k) spinal cord sections ten-days following facial-vein injection of $4\times10^{11}$ particles of scAAV9-CB-GFP into postnatal day-1 mice. GFP-expression (a,e,i) was predominantly restricted to lower motor neurons (a,e,i) and fibers that originated from dorsal root ganglia (a,e). GFP-positive astrocytes (i) were also observed scattered throughout the tissue sections. Lower motor neuron and astrocyte expression were confirmed by co-localization using choline acetyl transferase (ChAT) (b,f,j) and glial fibrillary acidic protein (GFAP) (c,g,k), respectively. A z-stack image (i-k) of the area within the box in h, shows the extent of motor neuron and astrocyte transduction within the lumbar spinal cord. Scale bars, 200 µm (d,h), 20 µm (l).
Figure 4:
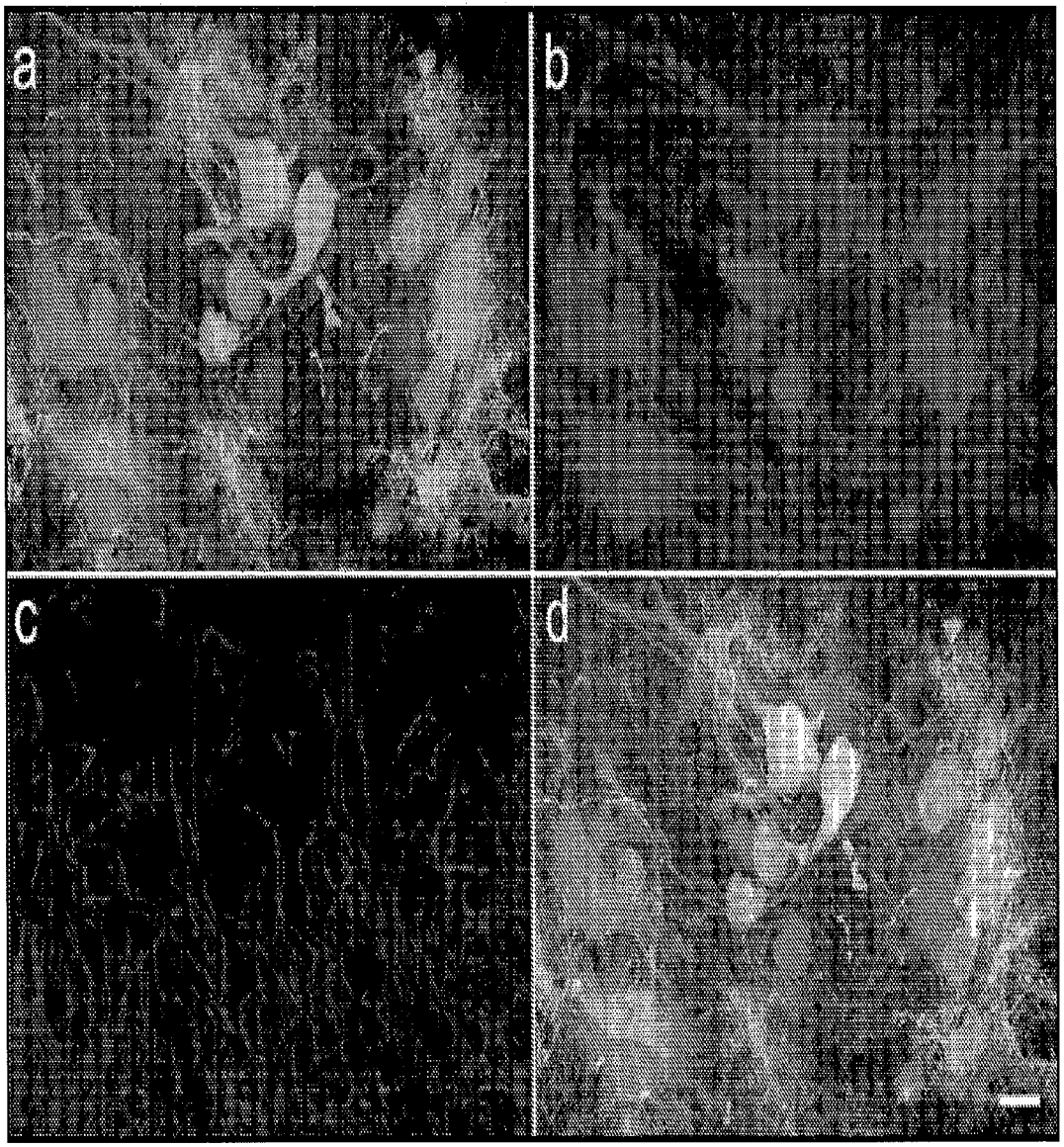
FIG. 4 shows that intravenous injection of AAV9 leads to widespread and long term neonatal spinal cord transduction in lumbar motor neurons. Z-series confocal microscopy showing GFP-expression in 21-day-old mice that received $4\times10^{11}$ particles of scAAV9-CB-GFP intravenous injections on postnatal day-1. Z-stack images of GFP (a), ChAT (b), GFAP (c) and merged (d) demonstrating persistent GFP-expression in motor neurons and astrocytes (d) for at least three-weeks following scAAV9-CB-GFP injection. Scale bar, 20 µm (d).

Animals were sacrificed 10- or 21-days post-injection, and brains and spinal cords were evaluated for transgene expression. Robust GFP-expression was found in heart and skeletal muscles as expected. Strikingly, spinal cords had remarkable GFP-expression throughout all levels, with robust GFP-expression in fibers that ascended in the dorsal columns and fibers that innervated the spinal grey matter, indicating dorsal root ganglia (DRG) transduction. GFP-positive cells were also found in the ventral region of the spinal cord where lower motor neurons reside (FIGS. 3a and e). Co-labeling for choline acetyl transferase (ChAT) and GFP-expression within the spinal cord demonstrated a large number of ChAT positive cells expressing GFP throughout all cervical and lumbar sections examined, indicating widespread LMN transduction (FIG. 4). Approximately 56% of ChAT positive cells strongly expressed GFP in sections analyzed of the lumbar spinal cord of 10 day-old animals and ~61% of 21 day-old animals, demonstrating early and persistent transgene expression in lower motor neurons (Table 1). Similar numbers of LMN expression were seen in cervical and thoracic regions of the spinal cord. This is the highest proportion of LMNs transduced by a single injection of AAV reported. In addition to widespread DRG and motor neuron transduction, we observed GFP-positive glial cells throughout the spinal grey matter, indicating that AAV9 could express in astrocytes with the CB promoter. The remarkable pattern of GFP-expression observed following postnatal day-one administration suggests two independent modes of viral entry into the CNS. Due to the ubiquitous GFP-expression throughout the brain, the virus likely crossed the developing BBB. However the GFP-expression pattern in the neonate spinal cord is defined with respect to the specific DRG and LMN transduction. The DRG and the LMN have projections into the periphery which suggests retrograde transport may be the mechanism of transduction. In support of retrograde transport as the method of spinal cord neuronal transduction, there were no GFP-positive interneurons observed in any section examined. Alternatively, the virus may have a LMN tropism after crossing the BBB, but this appears unlikely as ChAT positive cells still migrating from the central canal to the ventral horn were largely untransduced.

Figure 5:
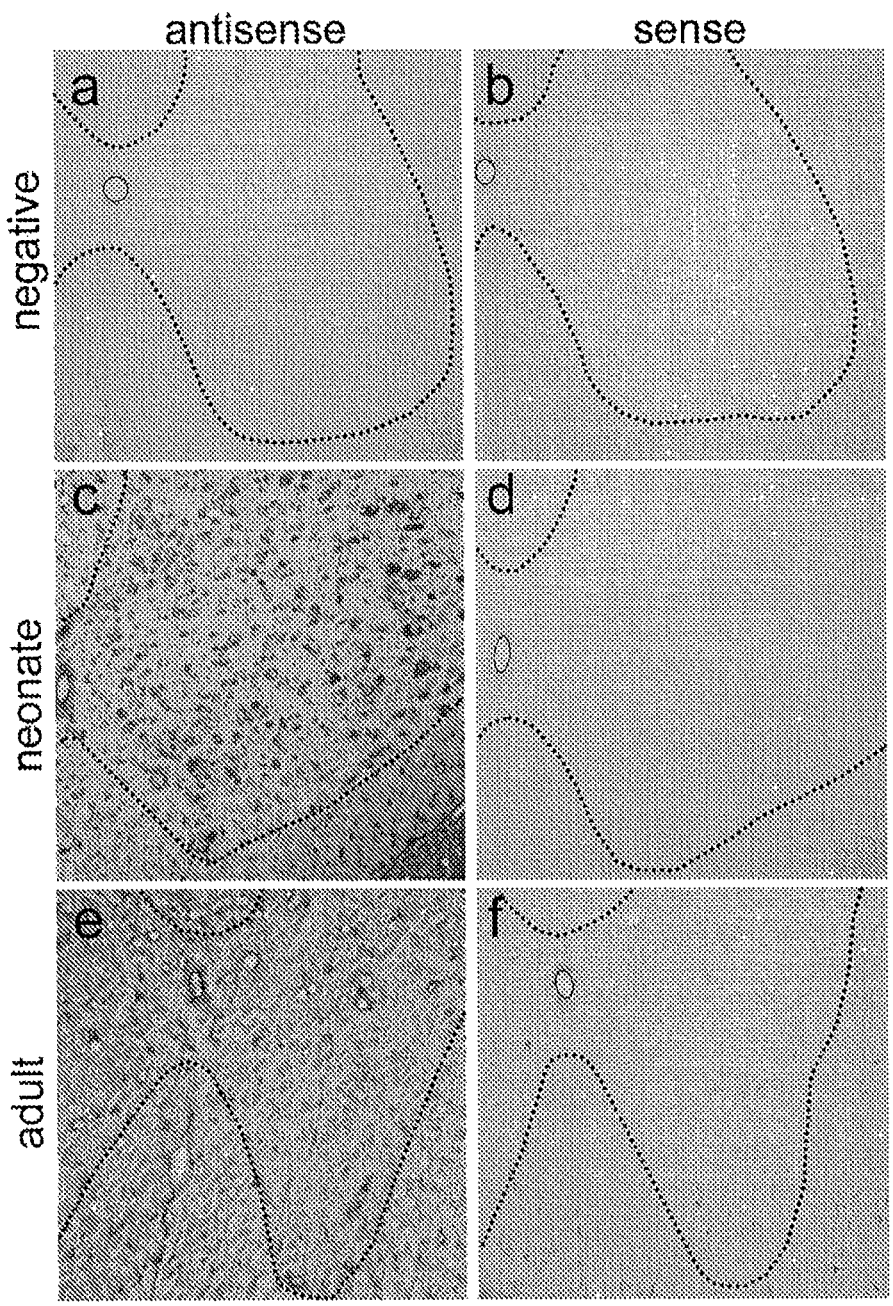
FIG. 5 depicts in situ hybridization of spinal cord sections from neonate and adult injected animals demonstrates that cells expressing GFP are transduced with scAAV9-CB-GFP. Negative control animals injected with PBS (a-b) showed no positive signal. However, antisense probes for GFP demonstrated strong positive signals for both neonate (c) and adult (e) sections analyzed. No positive signals were found for the sense control probe in neonate (d) or adult (f) spinal cord sections. Tissues were counterstained with Nuclear Fast Red for contrast while probe hybridization is in black.

In situ hybridization confirmed that viral transcription, and not protein uptake, was responsible for the previously unseen transduction pattern (FIG. 5).

Example 3

The ability of AAV9 to transduce and express protein in LMN was evaluated.

LMN transduction in the lumbar ventral horn was evaluated following intravenous administration of $1\times10^{11}$ particles of ss or scAAV9 GFP to postnatal day 1 mice in an effort to effectively deliver a transgene to spinal cord motor neurons. Both single-stranded and self-complementary AAV9-GFP vectors were produced via transient transfection production methods and were purified two times on CsCl gradients. The AAV9 GFP genomes are identical with the exception that scAAV genomes have a mutation in one ITR to direct packaging of specifically self-complementary virus. The single stranded AAV constructs do not contain the ITR mutation and therefore package predominantly single stranded virus. Viral preps were titered simultaneously using TAQMAN Quantitative PCR. P1 mice (n=5/group) were placed on an ice-cold plates to anesthetize and virus was delivered using 0.3 cc insulin syringes with 31 gauge needles that were inserted into the superficial facial vein. Virus was delivered in a volume of 50 µl. Animals recovered quickly after gene delivery with no adverse events noted. Animals were injected with a xylazine/ketamine mixture and were decapitated 10-days following injection and spinal cords were harvested then post-fixed in 4% paraformaldehyde, sectioned using a Vibratome and immunohistochemistry was performed using co-labeling for ChAT and GFP. Analysis of GFP expression was performed using a Zeiss Confocal Microscope.

Figure 6:
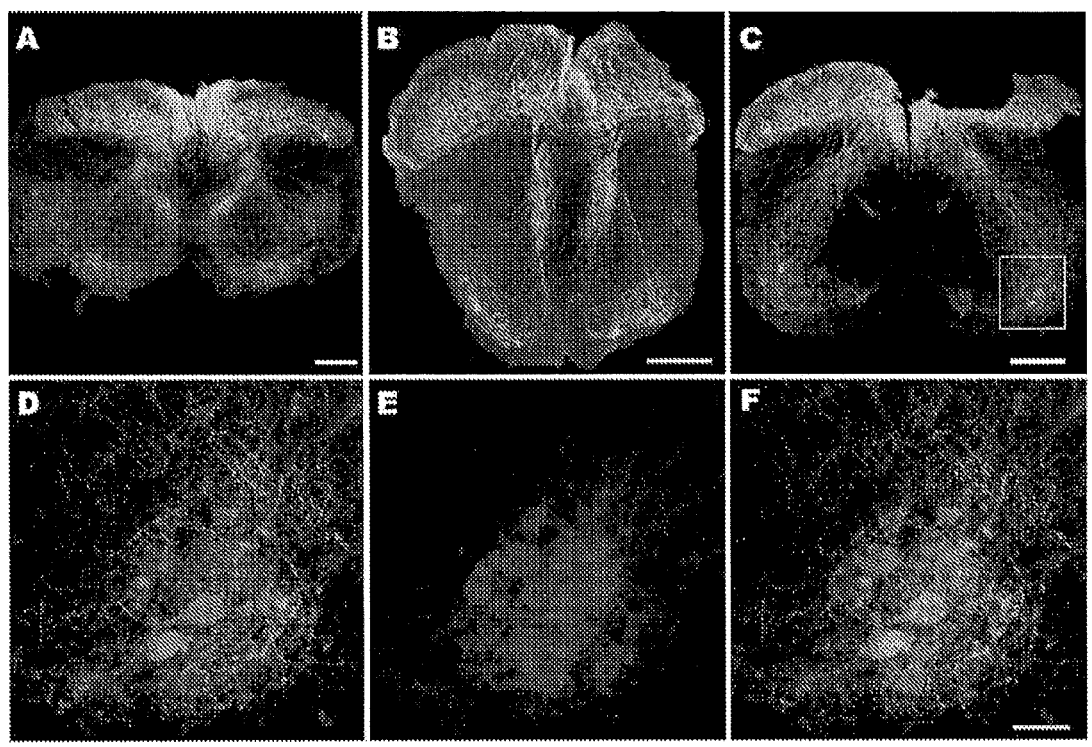
FIG. 6 depicts cervical (A), thoracic (B) and lumbar (C) transverse sections from mouse spinal cord labeled for GFP and ChAT. The box in (C) denotes the location of (D-F). GFP (D), ChAT (E) and merged (F) images of transduced motor neurons in the lumbar spinal cord. In addition to motor neuron transductions, GFP positive fibers are seen in close proximity and overlapping motor neurons (D and F). Scale bars=(A-C) 200 μm and (F) 50 μm.

Intravenous injection of single stranded AAV9-GFP resulted in widespread DRG transduction as evidenced by GFP positive fibers innervating the spinal grey matter and ascending in the dorsal columns (FIG. 6A-C). Numerous sections showed strong GFP staining in motor neurons as assessed by co-labeling GFP with Choline acetyltransferase (ChAT) (FIG. 3E-F). Counting the total number of motor neurons in treated animals demonstrated approximately 8% of total motor neurons residing in the lumbar region of the spinal cord were transduced. This finding was remarkable given that motor neuron transduction has typically been very low (less than 1% of total motor neurons), particularly by remote delivery approaches such as retrograde transport.

Example 4

Self-complementary scAAV9 vectors that do not require second-strand synthesis (a rate limiting step of AAV vectors) which would allow for greater efficiencies of expression in motor neurons, were evaluated.

Figure 7:
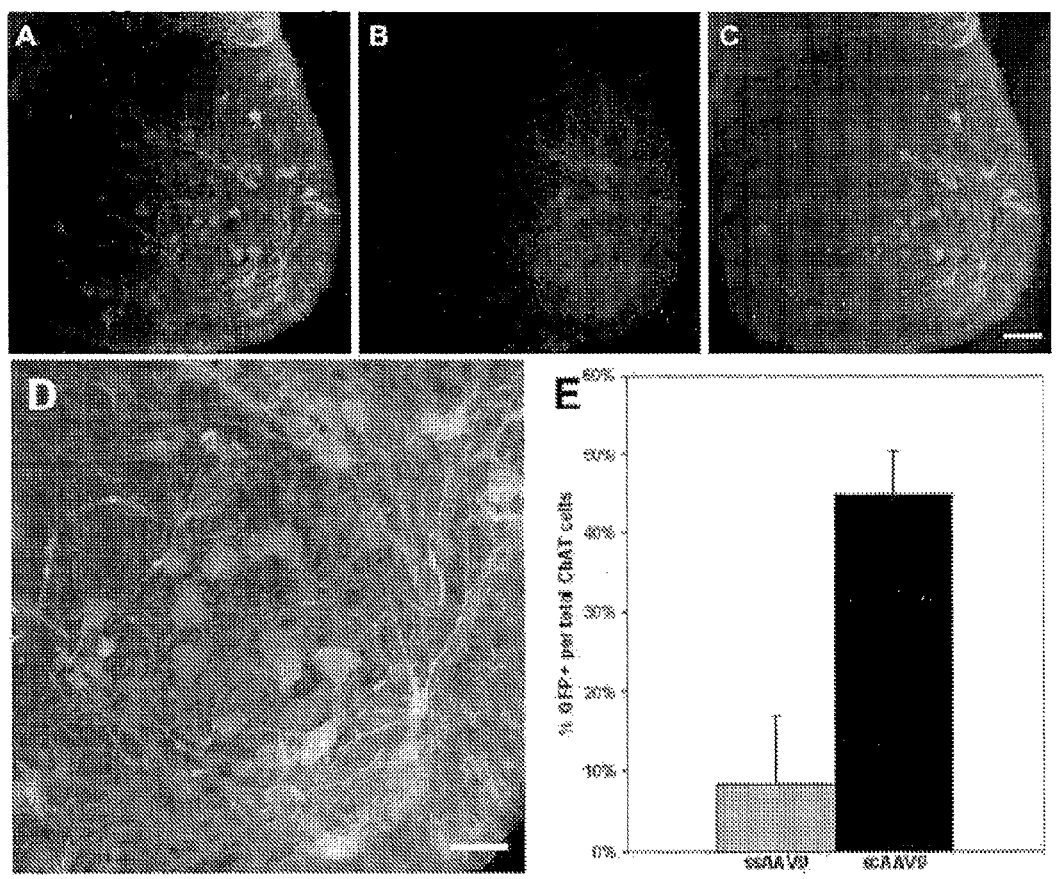
FIG. 7 depicts GFP (A), ChAT (B) and merged (C) images of a transverse section through lumbar spinal cord of a P10 mouse that had previously been injected at one day old with scAAV9 GFP. (D) represents a z-stack merged image of the ventral horn from (C). (E) shows that the scAAV9 vector resulted in more transduced motor neurons when compared to ssAAV9 vector in the lumbar spinal cord. Scale bars=(C) 100 μm and (D) 50 μm.

Viral particles were prepared as in Example 3. Intravenous injections into the facial vein of P1 pups were performed as described above and the animals as described above 10 days post-injection. As with ssAAV9 injections significant transduction of DRG was observed throughout the spinal cord. Remarkably, significant motor neuron transduction in treated animals was found in the two areas of the spinal cord that were evaluated including the cervical and lumbar spinal cord. Quantification of GFP+/ChAT+ double labeled cells expressed as a percentage of total ChAT+ cells within the lumbar spinal cord showed that ~45% of LMN were transduced by dsAAV9 compared with ~8% of ssAAV9 (FIG. 7E). Indeed, some regions of the spinal cord showed >90% motor neuron transduction (FIG. 7D) and other regions may have greater amounts of GFP positive motor neurons, given that dim GFP positive cells were not counted due to a conservative GFP positive scoring used in the counting. This amount of LMN transduction following a single injection of AAV has not previously been reported.

Example 5

Further investigation focused on whether AAV9 vectors were enhanced for retrograde transport to target DRG and LMNs or could easily pass the BBB in neonates.

Figure 8:
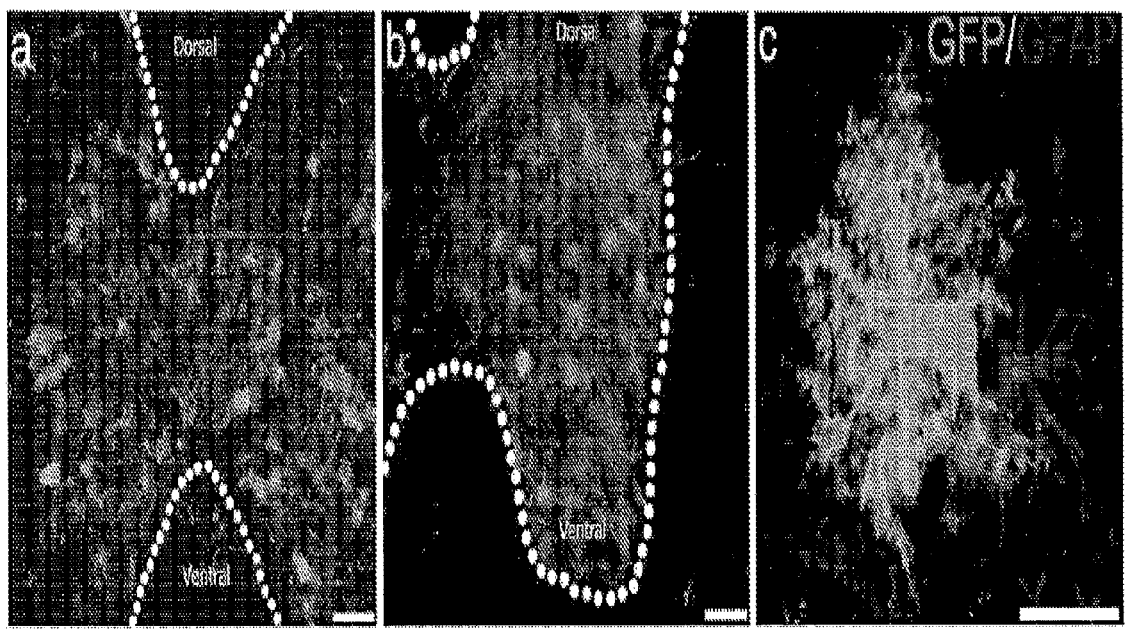
FIG. 8 depicts AAV9-GFP targeting of astrocytes in the spinal cord of adult-mice. (A-B) GFP immunohistochemistry in cervical (A) and lumbar (B) spinal cord demonstrating astrocyte transduction following tail-vein injection. (hatched-line indicates grey-white matter interface). (C) GFP and GFAP immunohistochemistry from lumbar spinal cord indicating astrocyte transduction. Scale bars (A-B) 100 μm, (C) 20 μm.
Figure 9:
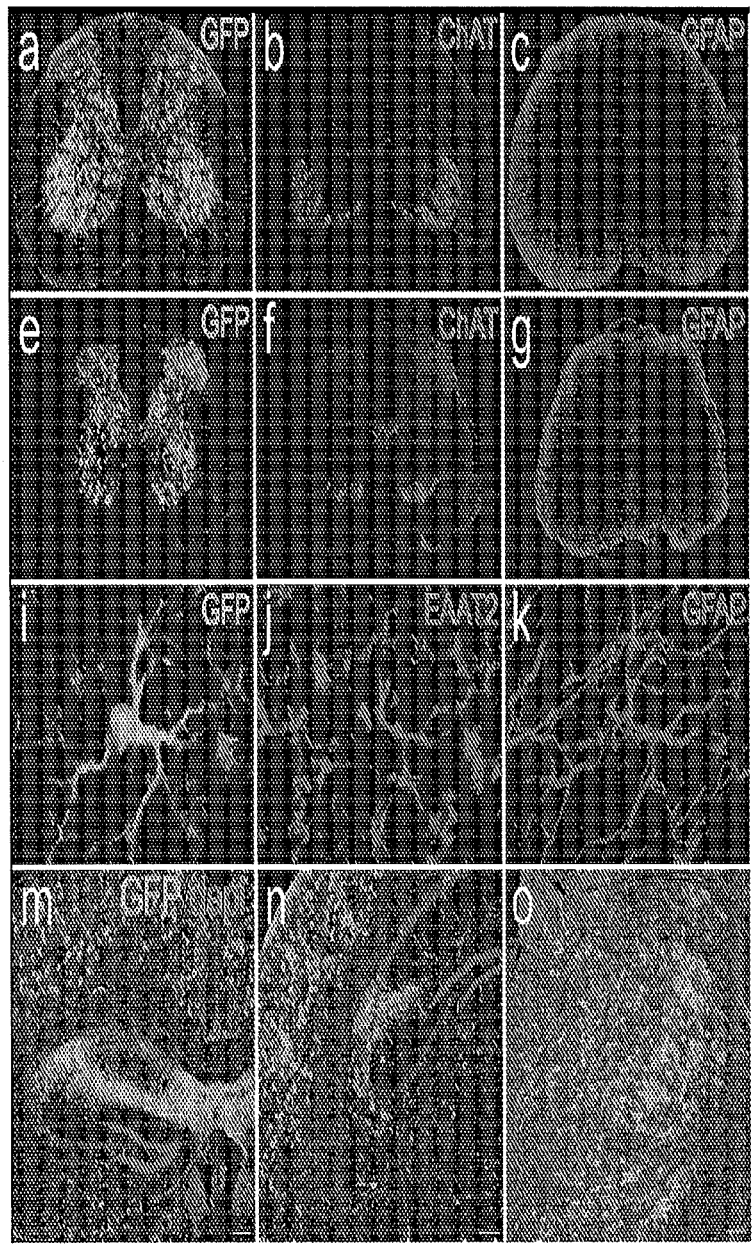
FIG. 9 shows that intravenous injection of AAV9 leads to widespread predominant astrocyte transduction in the spinal cord and brain of adult mice. GFP-expression in the cervical (a-c) and lumbar (e-g) spinal cord as well as the brain (m-o) of adult mice 7-weeks after tail vein injection of $4 \times 10^{12}$ particles of scAAV9-CB-GFP. In contrast to postnatal day-1 intravenous injections, adult tail vein injection resulted in almost exclusively astrocyte transduction. GFP (a,e), ChAT (b,f) and GFAP (c,g) demonstrate the abundance of GFP expression throughout the spinal grey matter, with lack of co-localization with lower motor neurons and white matter astrocytes. Co-localization of GFP (i), excitatory amino acid transporter 2 (EAAT2) (j), and GFAP (k) confirm that transduced cells are astrocytes. Tail vein injection also resulted in primarily astrocyte transduction throughout the brain as seen in the cortex (m-n), thalamus (o) and midbrain. Neuronal GFP-expression in the brain was restricted to the hippocampus and dentate gyrus (m-n, FIG. 11e-f).
Figure 10:
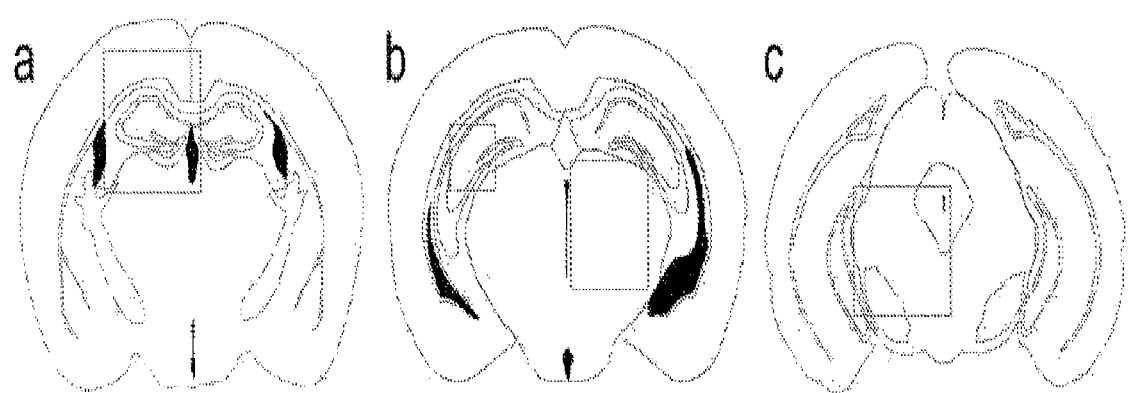
FIG. 10 depicts diagrams of coronal sections throughout the mouse brain corresponding to the approximate locations shown in (FIG. 9m-o). The box in (a) corresponds to the location shown in (FIG. 9m). The smaller box in (b) corresponds to (FIG. 9n) and the larger box to (FIG. 9o).

The pattern of transduction was examined to determine if it was consistent between neonates and adult animals. Adult mice were injected via tail vein delivery using $4 \times 10^{11}$ to $5 \times 10^{11}$ particles of scAAV9-CB-GFP. A strikingly different transduction pattern was seen in adult treated animals compared to the treated neonates. Most noticeably, there was an absence of GFP positive DRG fibers and a marked decrease in LMN transduction in all cervical and lumbar spinal cord sections examined. GFP-positive astrocytes were easily observed throughout the entire dorsal-ventral extent of the grey matter in all regions of the spinal cord (FIG. 8a-b and FIGS. 9a-c and e-g) with the greatest GFP-expression levels found in the higher dosed animals. Co-labeling of GFP-positive cells with astroglial markers excitatory amino acid transporter 2 (EAAT2) and glial fibrillary acidic protein (GFAP) (FIG. 8C) demonstrated that approximately 90% of the GFP-positive cells were astrocytes. Counts of total astrocytes in the lumbar region of the spinal cord by z-series collected confocal microscopy showed over 64% of total astrocytes were positive for GFP (FIG. 9i-k and Table 1). FIG. 10 depicts diagrams of coronal sections throughout the mouse brain corresponding to the approximate locations shown in (FIG. 9m-o). The box in (a) corresponds to the location shown in (FIG. 9m). The smaller box in (b) corresponds to (FIG. 9n) and the larger box to (FIG. 9o).

Viral transcription was again confirmed in adult tissues with in situ hybridization (FIG. 5). Furthermore, whereas neonate intravenous injection resulted in indiscriminate astrocyte and neuronal transduction throughout the brain, adult tail-vein injections produced isolated and localized neuronal expression only in the hippocampus and dentate gyrus (FIG. 9m-n and FIG. 11e-f) in both low and high dose animals. Low-dose animals had isolated patches of transduced astrocytes scattered throughout the entire brain. Of significance, high-dose animals had extensive astrocyte and vascular transduction throughout the entire brain (FIG. 9m-o and FIG. 11e-f) that persisted for at least seven-weeks post-injection (n=5), suggesting a dose-response of transduction, without regional specificity.

To date, efficient glial transduction has not been reported for any AAV serotype indicating that AAV9 has a unique transduction property in the CNS following intravenous delivery. An occasional neuron transduced in the spinal cord, although these events were scarce in adult animals. Furthermore, whereas neonate intravenous injection resulted in indiscriminate transduction throughout the brain, adult tail vein injections produced isolated and localized neuronal expression in the hippocampus with isolated patches of glial transduction scattered throughout the entire brain. The scarcity of LMN and DRG transduction seen in the adult paradigm suggests there is a developmental period in which access by circulating virus to these cell populations becomes restricted. Assuming a dependence on retrograde transport for DRG and LMN transduction following intravenous injection, Schwann cell or synapse maturation may be an important determinant of successful rAAV9 LMN and DRG transduction.

The results demonstrate the striking capacity of AAV9 to efficiently target neurons, and in particular motor neurons in the neonate and astrocytes in the adult following intravenous delivery. A simple intravenous injection of AAV9 as described here is clinically relevant for both SMA and ALS. In the context of SMA, data suggests that increased expression of survival motor neuron (SMN) gene in LMNs may hold therapeutic benefit [Azzouz et al., *The Journal of Clinical Investigation*, 114: 1726-1731 (2004) and Baughan et al., *Mol. Ther.* 14: 54-62 (2006)]. The importance of the results presented here is that with a single injection SMN expression levels are effectively restored in LMN. Additionally, given the robust neuronal populations transduced throughout the CNS in neonatal animals, this approach also allows for overexpressing or inhibiting genes using siRNA [see, for example, Siegel et al., *PLoS Biology*, 2: e419 (2004)]. The results also demonstrated efficient targeting of astrocytes in adult-treated animals and this finding is relevant for treating ALS where the non-cell autonomous nature of disease progression has recently been discovered and astrocytes have been specifically linked to disease progression [Yamanaka et al., *Nature Neuroscience*, 11: 251-253 (2008)]. Targeting these cells with trophic factors or to circumvent aberrant glial activity is useful in treating ALS [Dodge et al., *Mol. Ther.*, 16(6):1056-64 (2008)].

Example 6

Optimal delivery of AAV9 expressing SMN is described for postnatal gene replacement in a mouse model of Type 2 SMA.

Studies of the SMA patient population and the various SMA animal models have established a positive correlation between amounts of full-length SMN protein produced and lessened disease severity. Histone deacetylase (HDAC) inhibitors and small molecules are currently being investigated for their ability to increase transcript production or alter exon 7 inclusion from the remaining SMN2 gene [Avila et al., *J. Clin. Invest.*, 117(3):659-71 (2007) and Chang et al., *Proc. Natl. Acad. Sci. USA*, 98(17):9808-9813 (2001)]. Data presented herein demonstrates that a large percentage of LMNs can be targeted with a scAAV9 vector, and SMN gene replacement to treat SMA animals is therefore contemplated.

Mendelian inheritance predicts 25% of the pups in the litters of SMA breeders to be affected. Affected SMA mice are produced by interbreeding $SMN2^{+/+}$, $SMN\Delta7^{+/+}$, $Smn^{+/-}$ mice. Breeders are maintained as homozygotes for both transgenes and heterzygotes for the knockout allele. Mice were genotyped by PCR following extraction of total genomic DNA from a tail snip (see below). One primer set was used to confirm the presence of the knockout allele while the second primer set detected an intact mouse Smn allele. Animals were treated with either scAAV9 SMN or scAAV9 GFP as controls.

SMA parent mice ($Smn^{+/-}$, $SMN2^{+/+}$, $SMN\Delta7^{+/+}$) were time mated [Monani et al., Human Molecular Genetics 9: 333-339 (2000)]. Cages were monitored 18-21 days after visualization of a vaginal plug for the presence of litters. Once litters were delivered, the mother was separated out, pups were given tattoos for identification and tail samples were collected. Tail samples were incubated in lysis solution (25 mM NaOH, 0.2 mM EDTA) at 90° C. for one hour. After incubation, tubes were placed on ice for ten minutes and then received an equal volume of neutralization solution (40 mM Tris pH5). After the neutralization buffer, the extracted genomic DNA was added to two different PCR reactions for the mouse Smn allele (Forward 1: 5'-TCCAGCTCCGG-GATATTGGGATTG (SEQ ID NO: 2), Reverse 1: 5'-AG-GTCCCACCACCTAAGAAAGCC (SEQ ID NO: 3), Forward 2: 5'-GTGTCTGGGCTGTAGGCATTGC (SEQ ID NO: 4), Reverse 2: 5'-GCTGTGCCTTTTGGCTTATCTG (SEQ ID NO: 5)) and one reaction for the mouse Smn knockout allele (Forward: 5'-GCCTGCGATGTCGGTTTCTGT-GAGG (SEQ ID NO: 6), Reverse: 5'-CCAGCGCGGATCG-GTCAGACG (SEQ ID NO: 7)). After analysis of the genotyping PCR, litters were culled to three animals. Affected animals ($Smn^{-/-}$, $SMN2^{+/+}$, $SMN\Delta7^{+/+}$) were injected as previously described with $5\times10^{11}$ particles of self complementary AAV9 SMN or GFP [Foust et al., Nat Biotechnol 27: 59-65 (2009)].

AAV9 was produced by transient transfection procedures using a double stranded AAV2-ITR based CB-GFP vector, with a plasmid encoding Rep2Cap9 sequence as previously described [Gao et al., Journal of Virology 78: 6381-6388 (2004)] along with an adenoviral helper plasmid; pHelper (Stratagene, La Jolla, Calif.) in 293 cells. The serotype 9 sequence was verified by sequencing and was identical to that previously described [Gao et al., Journal of Virology 78: 6381-6388 (2004)]. Virus was purified by two cesium chloride density gradient purification steps, dialyzed against phosphate-buffered-saline (PBS) and formulated with 0.001% Pluronic-F68 to prevent virus aggregation and stored at 4° C. All vector preparations were titered by quantitative-PCR using Taq-Man technology. Purity of vectors was assessed by 4-12% SDS-Acrylamide gel electrophoresis and silver staining (Invitrogen, Carlsbad, Calif.).

To determine transduction levels in SMA mice ($SMN2^{+/+}$; $SMN\Delta7^{+/+}$; $Smn^{-/-}$), $5\times10^{11}$ genomes of scAAV9-GFP or -SMN (n=4 per group) under control of the chicken-β-actin hybrid promoter were injected into the facial vein at P1. Forty-two ±2% of lumbar spinal motoneurons were found to express GFP 10 days post injection. The levels of SMN in the brain, spinal cord and muscle in scAAV9-SMN-treated animals are shown in. SMN levels were increased in brain, spinal cord and muscle in treated animals, but were still below controls ($SMN2^{+/+}$; $SMN\Delta7^{+/+}$; $Smn^{+/-}$) in neural tissue. Spinal cord immunohistochemistry demonstrated expression of SMN within choline acetyl transferase (ChAT) positive cells after scAAV9-SMN injection.

Pups were weighed daily and tested for righting reflex every other day from P5-P13. Righting reflex is analyzed by placing animals on a flat surface on their sides and timing 30 seconds to evaluate if the animals return to a upright position [Butchbach et al., Neurobiology of Disease 27: 207-219 (2007)]. Every five days between P15 and P30, animals were tested in an open field analysis (San Diego Instruments, San Diego, Calif.). Animals were given several minutes within the testing chamber prior to the beginning of testing then activity was monitored for five minutes. Beam breaks were recorded in the X, Y and Z planes, averaged across groups at each time point and then graphed.

Whether scAAV9-SMN treatment of SMA animals improved motor function was then evaluated. SMA animals treated with scAAV9-SMN or -GFP were evaluated for the ability of the animals to right themselves compared to control and untreated animals (n=10 per group). Control animals were found to right themselves quickly, whereas the SMN- and GFP-treated SMA animals showed difficulty at P5. By P13, however, 90% of SMN treated animals could right themselves compared to 20% of GFP-treated controls and 0% of untreated SMA animals, demonstrating that SMN-treated animals improved. Evaluating animals at P18 showed SMN-treated animals were larger than GFP-treated but smaller than controls. Locomotive ability of the SMN-treated animals were nearly identical to controls as assayed by x, y and z plane beam breaks (open field testing) and wheel running. Age-matched untreated SMA animals were not available as controls for open field or running wheel analysis due to their short lifespan.

Survival in SMN-treated SMA animals (n=11) compared to GFP-treated SMA animals (n=11) was then evaluated using Kaplan Meier survival analysis. No GFP-treated control animals survived past P22, with a median lifespan of 15.5 days. The body weight in treated SMN- or GFP-treated animals compared to wild-type littermates was analyzed. The GFP-treated animal's weight peaked at P10 and then precipitously declined until death. In contrast, SMN-treated animals showed a steady weight gain to approximately P40, where the weight stabilized at 17 grams, half of the weight of controls. No deaths occurred in the SMN-treated group until P97. Furthermore, this death appeared to be unrelated to SMA. The mouse died after trimming of long extensor teeth. Four animals (P90-99) were euthanized for electrophysiology of neuromuscular junctions (NMJ). The remaining six animals remain alive, surpassing 250 days of age.

For electrophysiology analysis, a recording chamber was continuously perfused with Ringer's solution containing the following (in mmol/l): 118 NaCl, 3.5 KCl, 2 $CaCl_2$, 0.7 $MgSO_4$, 26.2 $NaHCO_3$, 1.7 $NaH_2PO_4$, and 5.5 glucose, pH 7.3-7.4 (20-22° C., equilibrated with 95% $O_2$ and 5% $CO_2$). Endplate recordings were performed as follows. After dissection, the tibialis anterior muscle was partially bisected and folded apart to flatten the muscle. After pinning, muscle strips were stained with 10 μM 4-Di-2ASP [4-(4-diethylaminostyryl)-Nmethylpyridinium iodide] (Molecular Probes) and imaged with an upright epifluorescence microscope. At this concentration, 4-Di-2ASP staining enabled visualization of surface nerve terminals as well as individual surface muscle fibers. All of the endplates were imaged and impaled within 100 μm. Two-electrode voltage clamp were used to measure endplate current (EPC) and miniature EPC (MEPC)

amplitude. Muscle fibers were crushed away from the endplate band and voltage clamped to −45 mV to avoid movement after nerve stimulation.

To determine whether the reduction in endplate currents (EPCs) was corrected with scAAV9-SMN, EPCs were recorded from the tibialis anterior (TA) muscle [Wang et al., J Neurosci 24, 10687-10692 (2004)]. P9-10 animals were evaluated to ensure the presence of the reported abnormalities within our mice. Control mice had an EPC amplitude of 19.1±0.8 nA versus 6.4±0.8 nA in untreated SMA animals (p=0.001) confirming published results [Kong et al., J Neurosci 29, 842-851 (2009)]. Interestingly, P10 scAAV9-SMN-treated SMA animals had a significant improvement (8.8±0.8 vs. 6.4±0.8 nA, p<0.05) over age-matched untreated SMA animals. Gene therapy treatment, however, had not restored normal EPC at P10 (19.1±0.8 vs. 8.8±0.8 nA, p=0.001). At P90-99, there was no difference in EPC amplitude between controls and SMA mice that had been treated with scAAV-SMN. Thus, treatment with scAAV9-SMN fully corrected the reduction in synaptic current. Importantly, P90-99 age-matched untreated SMA animals were not available as controls due to their short lifespan.

The number of synaptic vesicles released following nerve stimulation (quantal content) and the amplitude of the muscle response to the transmitter released from a single vesicle (quantal amplitude) determine the amplitude of EPCs. Untreated SMA mice have a reduction in EPC due primarily to reduced quantal content [Kong et al., J Neurosci 29, 842-851 (2009)]. In our P9-10 cohort, untreated SMA animals had a reduced quantal content when compared with wild-type controls (5.7±0.6 vs. 12.8±0.6, p<0.05), but scAAV9-SMN treated animals were again improved over the untreated animals (9.5±0.6 vs. 5.7±0.6, p<0.05), but not to the level of wild-type animals (9.5±0.6 vs. 12.8±0.6, p<0.05). At P90-99, when quantal content was measured in treated SMA mice, a mild reduction was present (control=61.3±3.5, SMA-treated=50.3±2.6, p<0.05), but was compensated for by a statistically significant increase in quantal amplitude (control=1.39±0.06, SMA treated=1.74±0.08, p<0.05). Quantal amplitudes in young animals had no significant differences (control=1.6±0.1, untreated SMA=1.3±0.1, treated SMA=1.1±0.1 nA, p=0.28).

The reduction in vesicle release in untreated SMA mice was due to a decrease in probability of vesicle release, demonstrated by increased facilitation of EPCs during repetitive stimulation [Kong et al., J Neurosci 29: 842-851 (2009)]. Both control and treated SMA EPCs were reduced by close to 20% by the 10th pulse of a 50 Hz train of stimuli (22±3% reduction in control vs 19±1% reduction in treated SMA, p=0.36). This demonstrates that the reduction in probability of release was corrected by replacement of SMN. During electrophysiologic recording, no evidence of denervation was noted. Furthermore, all adult NMJs analyzed showed normal morphology and full maturity. P9-10 transverse abdominis immunohistochemistry showed the typical neurofilament accumulation in untreated SMA NMJs[Kong et al., J Neurosci 29: 842-851 (2009)], whereas treated SMA NMJs showed a marked reduction in neurofilament accumulation.

A recent study using an HDAC inhibitor to extend survival of SMA mice reported necrosis of the extremities and internal tissues [Narver et al., Ann Neurol 64: 465-470 (2008)]. In the studies described herein, mice developed necrotic pinna between P45-70. Pathological examination of the pinna noted vascular necrosis, but necrosis was not found elsewhere.

To explore the therapeutic window in SMA mice, systemic scAAV9-GFP injections were performed at varying postnatal time points to evaluate the pattern of transduction of motor neurons and astrocytes. scAAV9-GFP systemic injections in mice on P2, P5 or P10 showed distinct differences in the spinal cord. There was a shift from neuronal transduction in P2-treated animals toward predominantly glial transduction in older, P10 animals, consistent with previous studies and knowledge of the developing blood-brain barrier in mice [Foust et al., Nat. Biotechnol. 27: 59-65 (2009); Saunders et al., Nat. Biotechnol. 27: 804-805, author reply 805 (2009)].

To determine the therapeutic effect of SMN delivery at these various time points, small cohorts of SMA-affected mice were injected with scAAV9-SMN on P2, P5 and P10 and evaluated for changes in survival and body weight. P2-injected animals were rescued and indistinguishable from animals injected with scAAV9-SMN on P1. However, P5-injected animals showed a more modest increase in survival of approximately 15 days, whereas P10-injected animals were indistinguishable from GFP-injected SMA pups. These findings support previous studies demonstrating the importance of increasing SMN levels in neurons of SMA mice [Gavrilina et al., Hum. Mol. Genet. 17: 1063-1075 (2008)]. Furthermore, these results suggest a period during development in which intravenous injection of scAAV9 can target neurons in sufficient numbers for benefit in SMA.

The above results demonstrate robust, postnatal rescue of SMA mice with correction of motor function, neuromuscular electrophysiology, and increased survival following a one-time gene delivery of SMN. Intravenous scAAV9 treats neurons, muscle and vascular endothelium. Vascular delivery of scAAV9 SMN in the mouse was safe, and well tolerated.

Example 7

Figure 11:
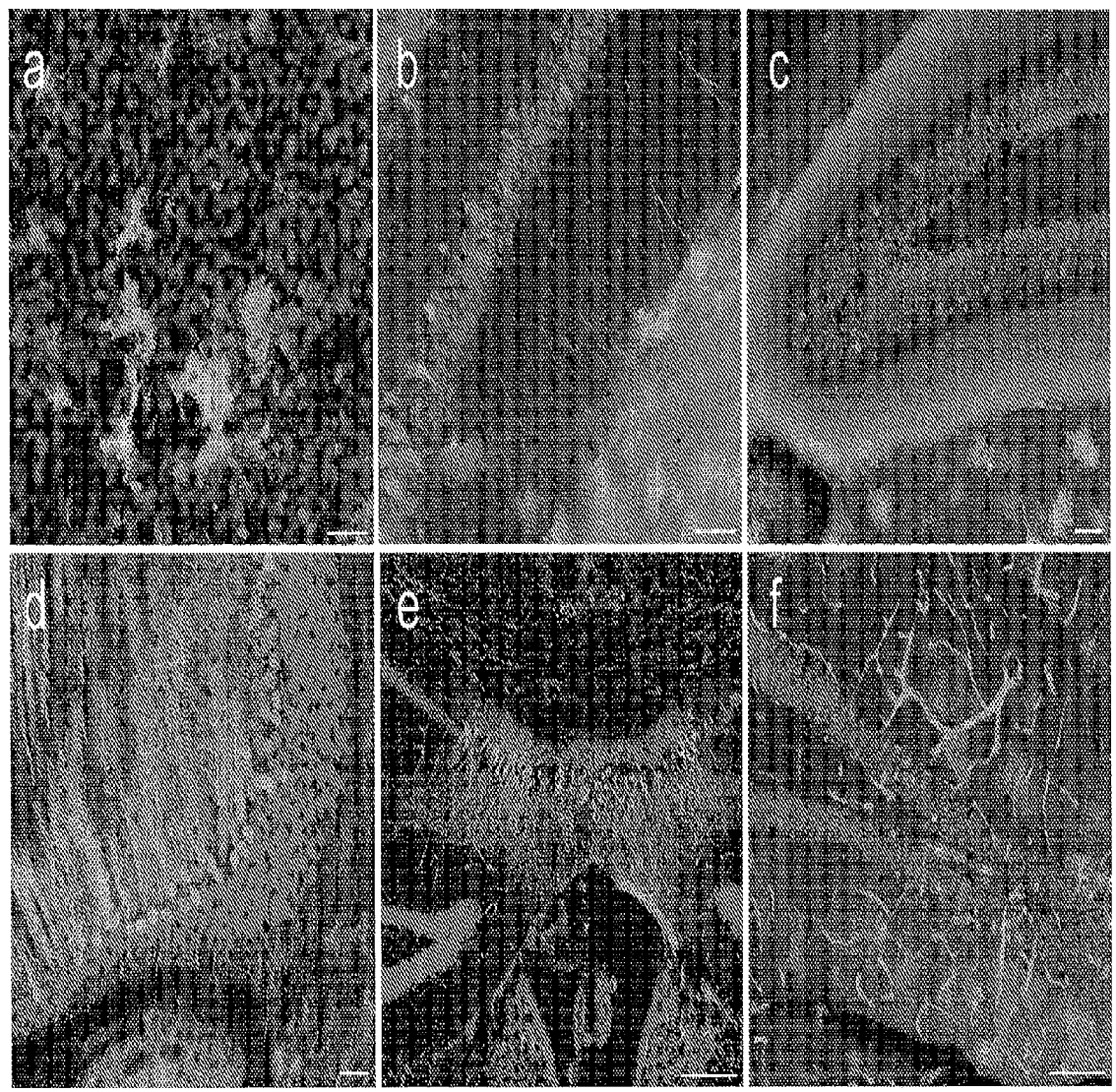
FIG. 11 depicts high-magnification of merged GFP and dapi images of brain regions following neonate (a-d) or adult (e-f) intravenous injection of scAAV9-CB-GFP. Astrocytes and neurons were easily detected in the striatum (a), hippocampus (b) and dentate gyrus (c) following postnatal day-1 intravenous injection of $4 \times 10^{11}$ particles of scAAV9-CB-GFP. Extensive GFP-expression within cerebellar Purkinje cells (d) was also observed. Pyramidal cells of the hippocampus (e) and granular cells of the dentate gyrus (f) were the only neuronal transduction within the brain following adult tail vein injection. In addition to astrocyte and neuronal transduction, widespread vascular transduction (f) was also seen throughout all adult brain sections examined. Scale bars, 200 μm (e); 100 μm (f), 50 μm (a-d).
Figure 12:
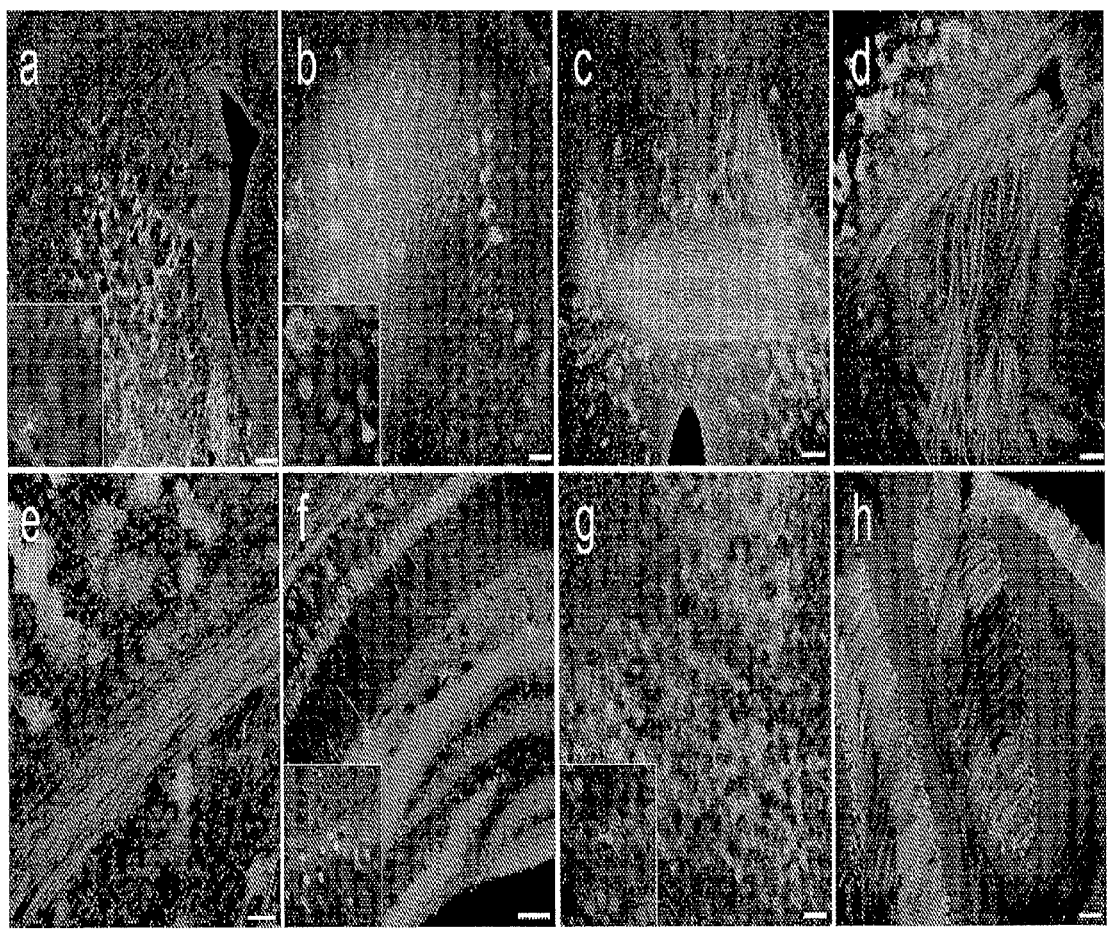
FIG. 12 depicts widespread GFP-expression 21-days following intravenous injection of $4 \times 10^{11}$ particles of scAAV9-CB-GFP to postnatal day-1 mice. GFP localized in neurons and astrocytes throughout multiple structures of the brain as depicted in: (a) striatum (b) cingulate gyms (c) fornix and anterior commissure (d) internal capsule (e) corpus callosum (f) hippocampus and dentate gyrus (g) midbrain and (h) cerebellum. All panels show GFP and DAPI merged images. Schematic representations depicting the approximate locations of each image throughout the brain are shown in (FIG. 13). Higher magnification images of select structures are available in (FIG. 11, 14). Scale bars, 200 μm (a); 50 μm (e); 100 μm (b-d,f-h).
Figure 13:
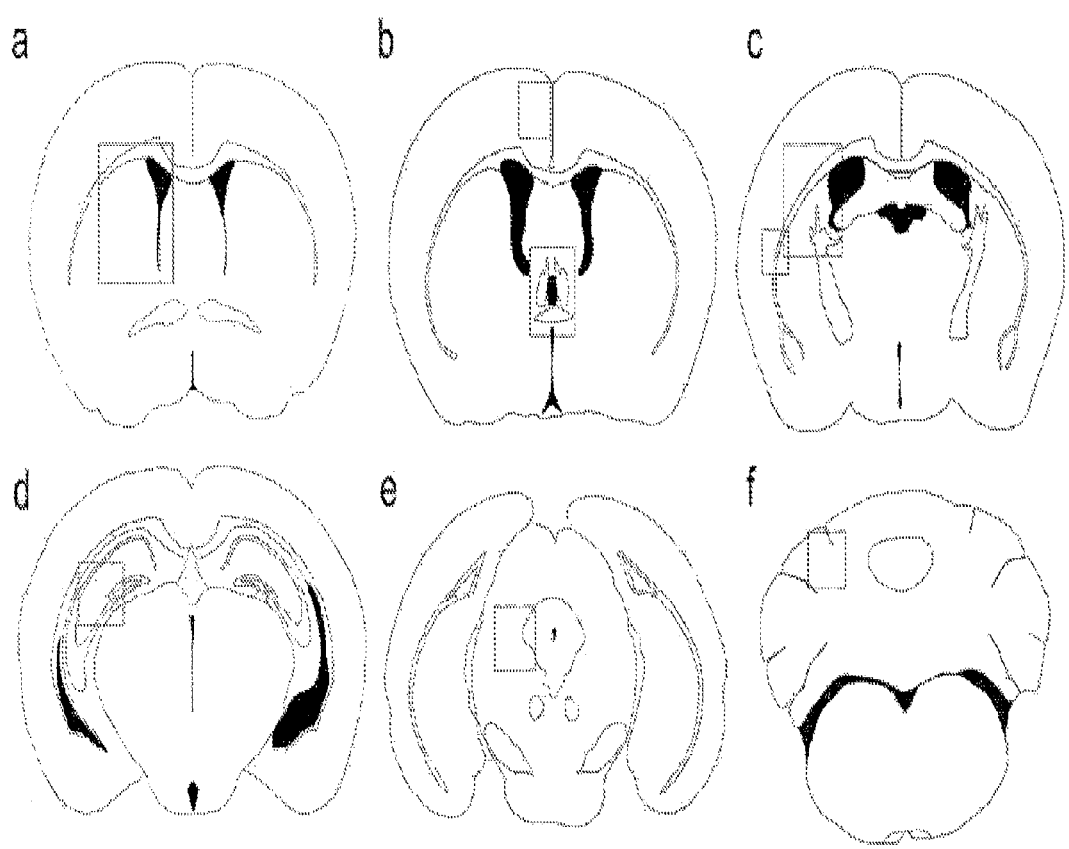
FIG. 13 depicts diagrams of coronal sections throughout the mouse brain. corresponding to the approximate locations shown in FIG. 12(a-h) for postnatal day-1 injected neonatal mouse brains. The box in (a) corresponds to the location of (FIG. 12a). The smaller box in (b) corresponds to (FIG. 12b) and the larger box to (FIG. 12c). The larger box in (c) corresponds to (FIG. 12d) while the smaller box in (c) represents (FIG. 12e). Finally, (d-f) correspond to (FIG. 12 f-h) respectively.

The brains of mice were examined following postnatal day-one intravenous injection of scAAV9-CBGFP and extensive GFP-expression was found in all regions analyzed, including the striatum, cortex, anterior commisure, internal capsule, corpus callosum, hippocampus and dentate gyrus, midbrain and cerebellum (FIG. 12a-h, respectively, FIG. 11). GFP-positive cells included both neurons and astrocytes throughout the brain. To further characterize the transduced neurons, brains were co-labeled for GFP and GAD67, a GABAergic marker. FIG. 13 depicts diagrams of coronal sections throughout the mouse brain corresponding to the approximate locations shown in FIG. 12a-h for postnatal day-1 injected neonatal mouse brains. The box in (13a) corresponds to the location of (FIG. 12a). The smaller box in (13b) corresponds to (FIG. 12b) and the larger box to (FIG. 12c). The larger box in (13c) corresponds to (FIG. 12d) while the smaller box in (13c) represents (FIG. 12e). Finally, (13d-f) correspond to (FIG. 12f-h) respectively.

Figure 14:
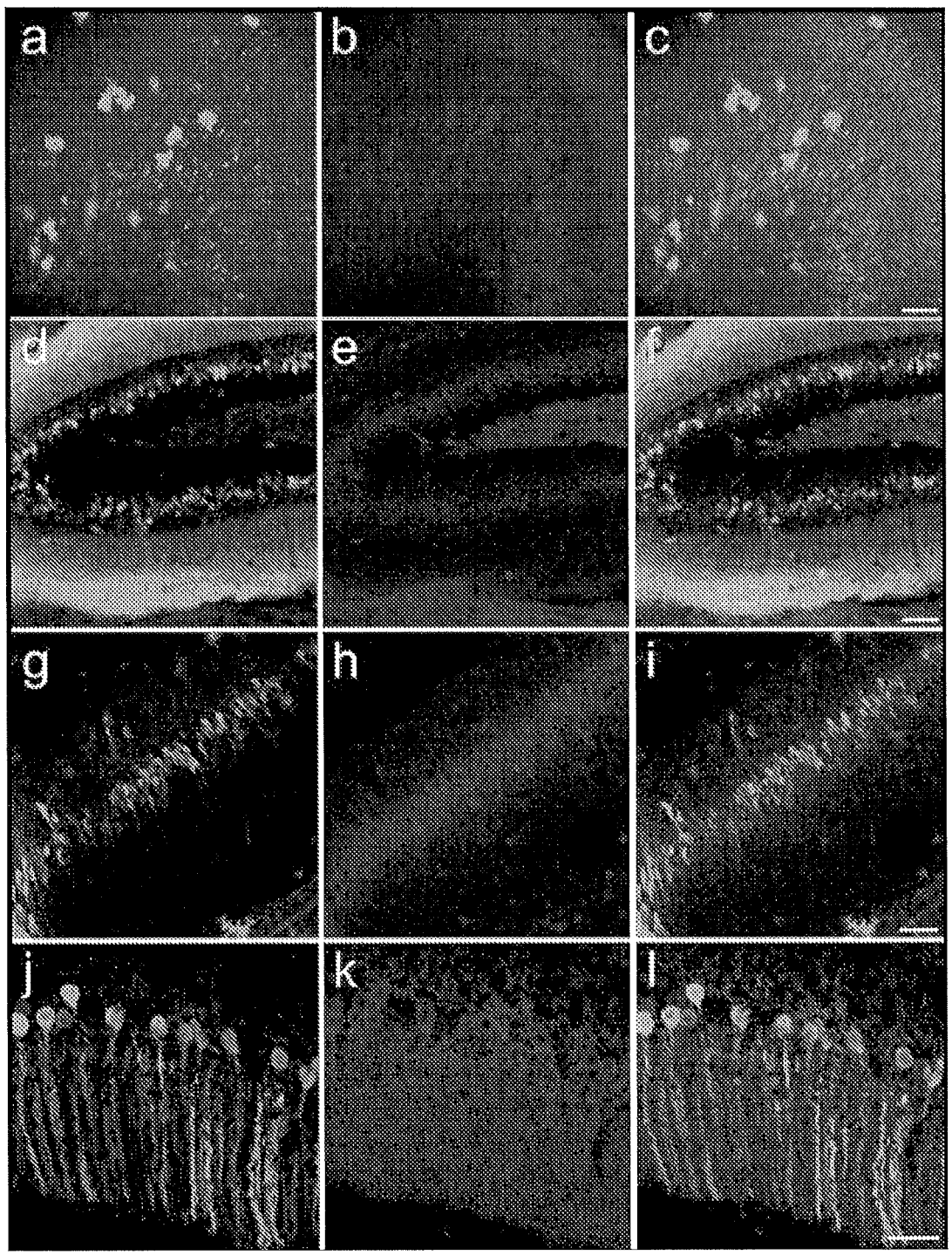
FIG. 14 depicts co-localization of GFP positive cells with GAD67. Immunohistochemical detection of GFP (a,d,g,j) and GAD67 (b,e,h,k) expression within select regions of mouse brain 21-days following postnatal day-1 injection of $4 \times 10^{11}$ particles of scAAV9-CB-GFP. Merged images (c,f,i,l) show limited co-localization of GFP and GAD67 signals in the cingulate gyrus (a-c), the dentate gyrus (d-f) and the hippocampus (g-i), but numerous GFP/GAD67 Purkinje cells within the cerebellum (l). Scale bars, 100 μm (c), 50 μm (a-b,d-l).

The cortex, hippocampus and dentate had very little colocalization between GFP and GAD67 labeled cells (FIG. 14a-i), while Purkinje cells in the cerebellum were extensively co-labeled (FIG. 14j-l). Finally, unbiased-estimated stereological quantification of transduction showed that 18.8+/−1.9% within the retrosplenial/cingulate cortex, 14.8+/−4.8% within the dentate gyrus and 71.8+/−3.65% within the Purkinje layer of total neurons were transduced following a one-time administration of virus (Table 1).

Example 8

Figure 15:
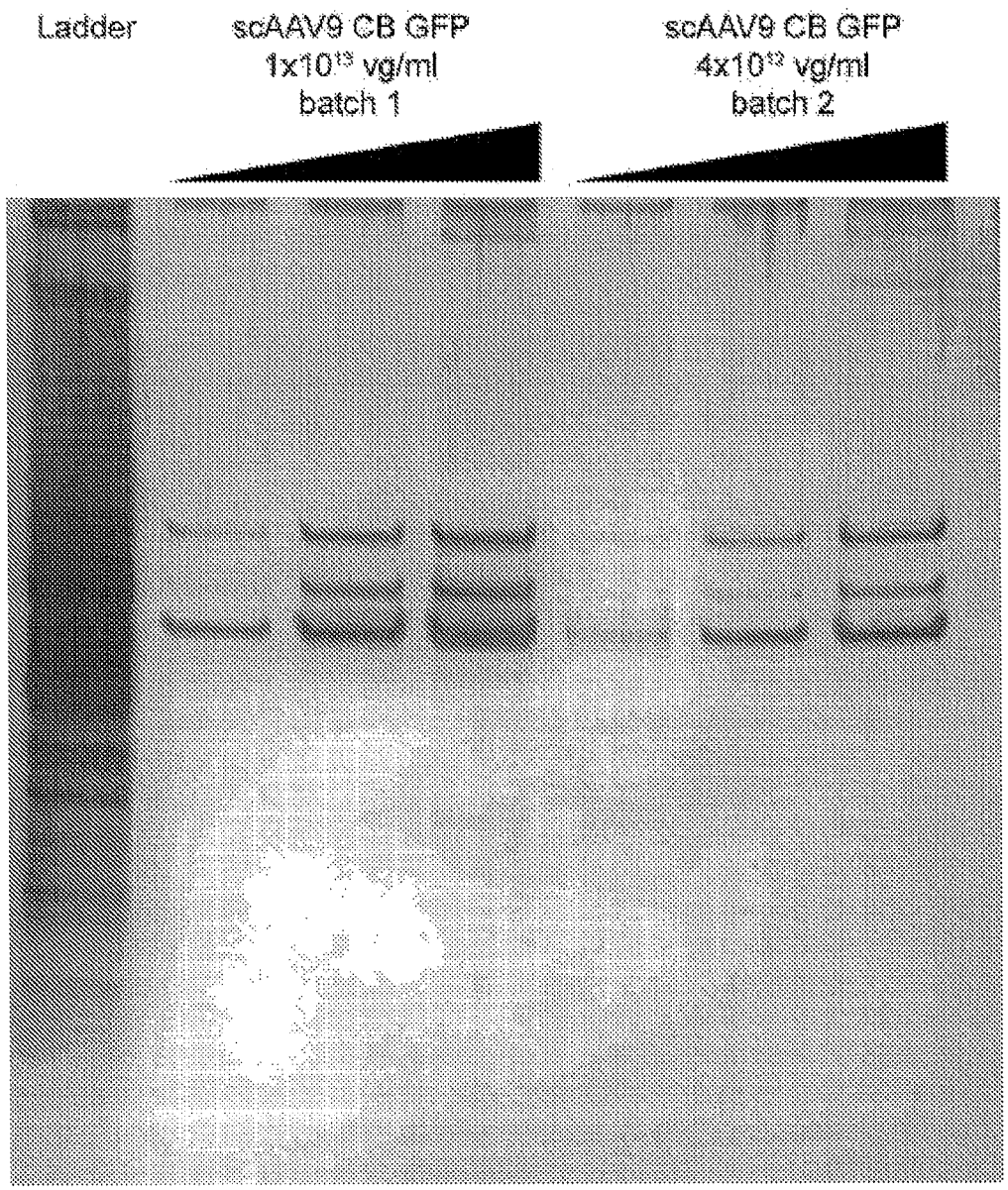
FIG. 15 depicts gel electrophoresis and silver staining of various AAV9-CBGFP vector preparations demonstrates high purity of research grade virus utilized in studies. Shown are 2 vector batches at varying concentrations demonstrating the predominant 3 viral proteins (VP); VP1, 2, 3 as the significant components of the preparation. 1 μl, 5 μl, and 10 μl were loaded of each respective batch of virus.
Figure 16:
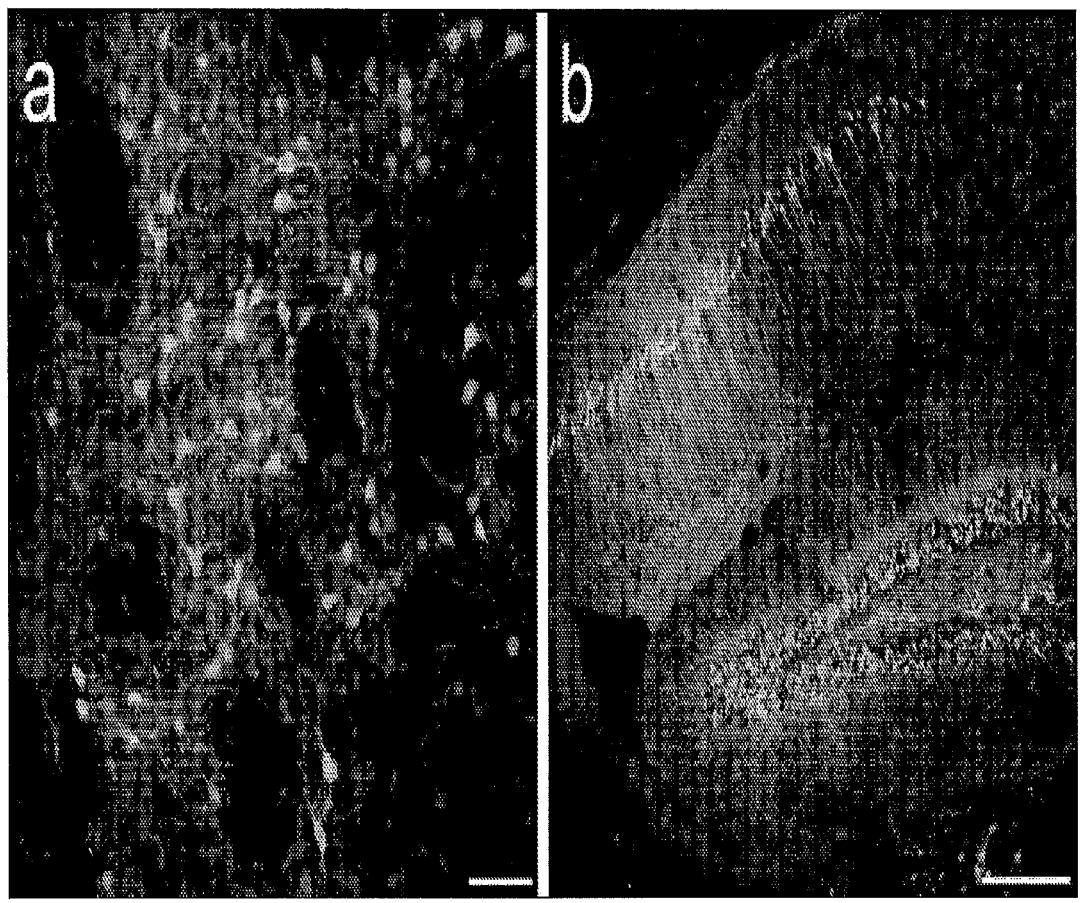
FIG. 16 depicts direct injection of scAAV9-CB-GFP into the brain and demonstrates predominant neuronal transduction. Injection of virus into the striatum (a) and hippocampus (b) resulted in the familiar neuronal transduction pattern as expected. Co-labeling for GFP and GFAP demonstrate a lack of astrocyte transduction in the injected structures with significant neuronal cell transduction. Scale bars, 50 μm (a), 200 μm (b).

Efficient astrocyte transduction by an AAV8-, but not an AAV9-vector, following direct brain injection has been previously reported. Astrocyte transduction, however, was suggested to be related to viral purification [Klein et al., Mol Ther 16: 89-96 (2008)]. To investigate whether AAV9 astrocyte transduction was related to vector purity or delivery route, multiple AAV9 preparations were evaluated for vector purity by silver-stain and $8 \times 10^{10}$ particles of the same scAAV9-CB-GFP vector preparations from the intravenous experiments were injected into the striatum and dentate gyrus of adult mice. Silver-staining showed that vector preparations were relatively pure and of research grade quality (FIG. 15). Two-weeks post-intracranial injection, we observed significant neuronal transduction within the injected regions using these vector preparations. However, no evidence for colocalization was found between GFP and GFAP labeling throughout the injected brains (n=3) (FIG. 16), as previously reported [Cearley et al., *Mol Ther* 16: 1710-1718 (2008)], suggesting the astrocyte transduction in this work may be injection route- and serotype-dependent and not due to vector purity.

The scarcity of LMN and DRG transduction seen in the adult paradigm suggests there is a developmental period in which access by circulating virus to these cell populations becomes restricted. Assuming a dependence on retrograde transport for DRG and LMN transduction following intravenous injection, Schwann cell or synapse maturation may be an important determinant of successful AAV9 LMN and DRG transduction. Direct intramuscular injection of AAV9 into adults did not result in readily detectable expression in motor neurons by retrograde transport. These results suggest that AAV9 escapes brain vasculature in a similar manner as skeletal and cardiac muscle vasculature. Once free of the vasculature, these data suggest that AAV9 infects the astrocytic-perivascular-endfeet that surround capillary endothelial cells [Abbott et al., *Nat Rev Neurosci* 7: 41-53 (2006)].

In summary, these results demonstrate the unique capacity of AAV9 to efficiently target cells within the CNS, and in particular widespread neuronal and motor neuron transduction in the neonate, and extensive astrocyte transduction in the adult following intravenous delivery. A simple intravenous injection of AAV9 as described herein may be clinically relevant for both SMA and ALS. In the context of SMA, data suggest that increased expression of survival motor neuron (SMN) gene in LMNs may hold therapeutic benefit [Azzouz et al., *The Journal of Clinical Investigation* 114: 1726-1731 (2004); Baughan et al., *Mol Ther* 14: 54-62 (2006)]. The importance of the results presented here is that a single injection may be able to effectively restore SMN expression levels in LMNs. Additionally, given the robust neuronal populations transduced throughout the CNS in neonatal animals, this approach may also allow for rapid, relatively inexpensive generation of chimeric animals for gene overexpression, or gene knock-down [Siegel et al., *PLoS Biology* 2: e419 (2004)]. Additionally, constructing AAV9 based vectors with neuronal or astrocyte specific promoters may allow further specificity, given that AAV9 targets multiple non-neuronal tissues following intravenous delivery [Inagaki et al., *Mol Ther* 14: 45-53 (2006); Pacak et al., *Circulation Research* 99: e3-9 (2006)]. The results also demonstrate efficient targeting of astrocytes in adult-treated animals, and this finding is relevant for treating ALS, where the non-cell autonomous nature of disease progression has recently been discovered, and astrocytes have been specifically linked to disease progression [Yamanaka et al., *Nature Neuroscience* 11: 251-253 (2008)]. The ability to target astrocytes for producing trophic factors, or to circumvent aberrant glial activity may be beneficial for treating ALS24. In sum, these data highlight a relatively non-invasive method to efficiently deliver genes to the CNS and are useful in basic and clinical neurology studies.

Example 9

The ability of scAAV9 to traverse the blood-brain barrier in nonhuman primates [Kota et al., *Sci. Transl. Med* 1: 6-15 (2009)] was also investigated. A male cynomolgus macaque was intravenously injected on P1 with $1 \times 10^{14}$ particles ($2.2 \times 10^{11}$ particles/g of body weight) of scAAV9-GFP and euthanized it 25 days after injection. Examination of the spinal cord revealed robust GFP expression within the dorsal root ganglia and motor neurons along the entire neuraxis, as seen in P1-injected mice. This finding demonstrated that early systemic delivery of scAAV9 efficiently targets motor neurons in a nonhuman primate.

Example 10

Self complementary (sc) rAAV9 bearing MECP2 cDNA under control of a fragment of its own promoter (scAAV9/MECP2), was shown to be capable of significantly stabilizing or reversing disease phenotypes when administered systemically into female RTT mouse models.

Figure 17:
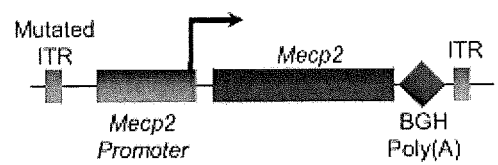
FIG. 17 is a schematic of scAAV9/MECP2 vector.

To counteract possible over-expression and better mimic the expression pattern of virally-mediated MECP2, a rAAV9 containing MECP2 (E1) cDNA under control of an ~730 bp fragment of its own promoter was constructed [Rastegar et al., *PloS One*, 4: e6810 (2009)] (scAAV9 MECP2; FIG. 17).

Mouse MECP2-α polynucldeotide was cloned in a plasmid downstream of a 730 bp fragment of MECP2 promoter. Recombinant AAV9 was produced by transient transfection procedures using a double-stranded AAV2-ITR-based MECP2 minimal promoter-MECP2 (E1) vector, with a plasmid encoding Rep2Cap9 sequence as previously described along with an adenoviral helper plasmid pHelper (Stratagene) in 293 cells [Gao et al., *J. Virol.* 78: 6381-6388 (2004) and Fu et al., Mol Ther., 8(6): 911-917 (2003)]. Virus was purified by cesium chloride density gradient purification steps as previously described, dialyzed against PBS and formulated with 0.001% Pluronic-F68 to prevent virus aggregation and stored at 4° C. [Ayuso et al., Gene Ther., 17(4):503-510 (2010)]. All vector preparations were titered by quantitative PCR using Taq-Man technology. Purity of vectors was assessed by 4-12% SDS-acrylamide gel electrophoresis and silver staining (Invitrogen). The resulting rAAV9 was named "scAAV9/MECP2." The sequence of its genome is shown in FIG. 22 and has in sequence: a mutated AAV2 ITR lacking the terminal resolution site, an approximately 730 bp murine MECP2 promoter fragment, SV40 intron sequences, murine MECP2α cDNA, a bovine growth hormone polyadenylation signal sequence and an AAV2 ITR.

Mice were group housed with littermates in standard housing on a 12:12 h light:dark cycle. MECP2$^{Stop}$ (Stock number: 006849) [Guy et al., *Science*, 315: 1143-1147 (2007)] and MECP2$^{Bird.knockout}$ (Stock number: 003890; MECP2$^{Bnull}$) [Guy et al., *Nature Genetics*, 27: 322-326 (2001)] mice were obtained from Jackson Laboratories and were on a C57BL/6 background. The wild type male mice were crossed to female MECP2$^{+/Stop}$ and MECP2$^{+/Bnull}$ mice to yield male and female MECP2$^{Stop}$ and MECP2$^{Bnull}$ genotypes. The floxed Stop sequence was identified from tail biopsies using the following primers: common 5'-AACAGTGCCAGCT-GCTCTTC-3' (SEQ ID NO: 8), WT 5'-CTGTATCCT-TGGGTCAAGCTG-3' (SEQ ID NO: 9), and mutant 5'-GC-CAGAGGCCACTTGTGTAG-3' (SEQ ID NO: 10). For Bird null following primers were used 5'-CCACCCTC-CAGTTTGGTTTA-3' (SEQ ID NO: 11) and 5'-GACCCCT-TGGGACTGAAGTT-3' (SEQ ID NO: 12) [Lioy et al., *Nature*, 475: 497-500 (2011)].

Figure 20:
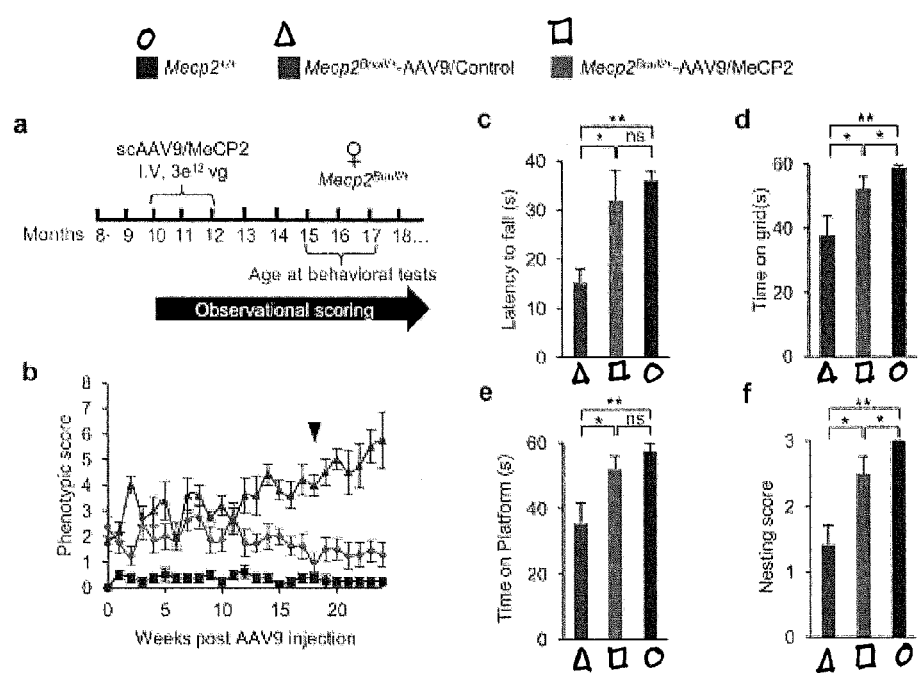
FIG. 20 shows systemic delivery of scAAV9/MECP2 virus into $Mecp2^{Bnull/+}$ mice prevents progression, or reverses aberrant behaviors. (a) Experimental paradigm. Mice were analyzed five months post injection. (b) Average observational scores of $Mecp2^{Bnull/+}$ mice injected with scAAV9/MeCP2 (n=8), scAAV9/Control (n=5). Non-injected ($Mecp2^{+/+}$) mice (n=8). Arrow indicates time of behavioral analysis. (c) Rotorod activity on third day of test. (d) Inverted grid test. (e) Platform test. scAAV9/MeCP2 (n=8), scAAV9/Control (n=5). $Mecp2^{+/+}$ (n=8). (f) Nesting ability. scAAV9/

Mice were placed in a restraint that positioned the mouse tail in a lighted, heated groove. The tail was swabbed with alcohol then injected intravenously with a 300 µl viral solution containing $3 \times 10^{12}$ DNase-resistant particles of scAAV9 in PBS (FIG. 20, panel A). After the injection, mice were returned to their cages. All animal procedures were approved by Oregon Health and Science University Institutional Animal Care and Use Committee.

For phenotype scoring, mice were removed from their home cage and placed onto a metal laminar flow hood for observation.

For mobility: 0=wild type; 1=reduced movement when compared to wild type, with extended freezing periods or extended delay to movement when first placed on the surface; 2=complete loss of movement when placed on the surface.

For gait: 0=wild type; 1=hind limbs spread wider than wild type when ambulating and/or a lowered pelvis when ambulating; 2=lack of full strides by hind limbs resulting in a dragging of hindquarters.

For hind limb clasping: 0=WT; hind limbs splay outward when suspended by the tail; 1=one hind limb is pulled into the body or forelimbs are stiff and splayed outward without motion; 2=one hind limb is pulled into the body and forelimbs are stiff and splayed outward without motion and might form a widened bowl shape, or both hind limbs are pulled into the body with or without abnormal forelimb posture.

For tremor: 0=no tremor; 1=intermittent mild tremor; 2=continuous tremor or intermittent violent tremor.

For general condition: 0=shiny coat, clear and opened eyes, normal body stance; 1=dull or squinty eyes, dull or ungroomed coat, somewhat hunched stance; 2=piloerection, hunched stance.

For behavioral testing, all tests were performed at the same time of day (12.00 to 18.00 hrs) and in the same dedicated observation room. Mice were never subjected to multiple tasks on the same day.

Open field activity—Mice were placed singly into the center of an open field arena (14×14 inches) equipped to record live images from the top. Activity was recorded for 20 minutes using StereoScan Software (Clever Systems) on a Dell computer fitted with a window operating system. Software calculated the total distance travelled and average velocity of the movements from recorded movies. The mice could not see the experimenter during recordings.

Rotorod—Mice were placed on an elevated rotating rod (diameter: 7 cm, elevated: 45 cm, Economex, Columbus Instruments, Columbus, Ohio, USA), initially rotating at 5.0 rpm. The rod accelerated 5.0 rpm/s. The latency to fall (s) was recorded manually by using individual mouse specific stopwatches. Each mouse receives three trials per day, with no delay between trials, on three consecutive days.

Platform test—Performed as described in Grady et al., *J. Neuroscience*, 26: 2841-2851 (2006) with some modifications. Each mouse was timed for how long it remained on an elevated, circular platform (3.0 cm in diameter) with rounded edges. A maximum score of 60 s was assigned if the mouse remained on the platform for the entire test trial without falling. Two trials were administered for each test with 4 h intervening between trials, and means were calculated across the trials for each mouse.

Inverted screen test—Performed as described in Grady et al., 2006 with some modifications. Each mouse was placed in the middle of wire grid (parallel metal wires 0.5 cm apart) that was inverted to 180°. A mouse was timed for how long it remained upside down on the screen, with a maximum score of 60 s being given if the animal did not fall. Two trials were administered for each test with 4 h intervening between trials, and means were calculated across the trials for each mouse.

Nesting ability—Mice were placed in individual cages and provided with a nest building material (5 cm×5 cm×0.5 cm). The material was placed in top left corner of cage and nesting ability was scored over night based on the interaction of individual mouse with nesting material. The score of 0, 1, 2 and 3 were assigned. The score 0 was assigned to mouse that not at all interacted with material, score 3 was assigned to mouse that completely used the material to build a nest.

Novel Object recognition test—Test is conducted in open field arena used to evaluate motor activity. The two objects (a sphere and a box) were selected based on similar volume and unbiased interaction of wild type mice. During habituation, the mice were allowed to explore an empty arena for 5 minutes. Twenty-four hours after habituation, the mice were exposed to the familiar arena with two identical objects (sphere) placed at an equal distance for 5 minutes. The next day, same exercise was repeated. On third day of the test, the mice are allowed to explore the open field in the presence of the familiar and a novel object (Box) for 5 minutes to test cognition. The time spent exploring each object on second and final day of test was recorded to estimate the extent of novel object recognition by calculating discrimination index (DI)=(Tn−Tf)/(Tn+Tf). Tn; time with novel object and Tf; time with familiar object. The DI value can vary between +1 and −1, where a positive score indicates more time spent with the novel object, a negative score indicates more time spent with the familiar object, and a zero score indicates a null preference.

After phenotypic scoring and behavioral testing, mice were anaesthetized by intraperitoneal injection of Avertin (2-2-2 Tribromoethanol) and sacrificed by transcardial perfusion of 4% parafomaldehyde in phosphate-buffered saline. Brains were equilibrated in 30% sucrose overnight at 4° C. Sagittal sections (40 μm) were cut at −20° C. using a cryostat (Leica) and stored at −20° C. Sections were immunolabeled overnight at 4° C. using the following primary antibodies: rabbit-MECP2 (1:500, Covance), mouse-GFAP (1:500, Abcam), chicken-GFAP (1:200, Abeam), mouse-NeuN (1:200, Millipore). Appropriate Alexa/Dylight Fluor secondary antibodies (1:500, Molecular Probes) were used for 1 h at room temperature. DAPI was present in the ProLong Gold Antifade (Invitrogen) mounting reagent. Nissl staining (at either 594 nm or 640 nm) was performed as instructed by the manufacturer (NeuroTrace, Invitrogen). All images were collected on a Zeiss confocal laser scanning LSM 510 microscope.

MECP2 expressing cells were identified as described in Lioy et al. (2011) with some modifications: nuclei of astrocytes (GFAP+ at 555 nm or 640 nm; NeuN− at 555 nm or 640 nm) and neurons (NeuN+ at 555 nm or 640 nm) were first identified by DAPI staining. Cells with clearly identified nuclei were then assessed for MECP2 expression by analyzing 505 nm signal (excitation: 488 nm) in the nucleus.

The following measurements were analyzed using one-way ANOVA followed, when appropriate (P<0.05), by Newman-Keuls post-hoc test: anatomical and cell-type expression patterns of transduced MECP2, whole body and brain weights, respiratory parameters, open field activity and time on rotarod. The following measurements were analyzed using Kruskal-Wallis test followed, when appropriate (P<0.05), by Dunn's multiple comparisons test: phenotype severity scores, nesting scores, time on an inverted grid, time on a platform, and novel object recognition. Survival curves were compared using the Log-Rank method. All statistics were performed using PRISM 5.0 software.

The scAAV9/MECP2 construct is expressed in both neurons and glia in vitro, and in MECP2Bnull/y mice, virally-expressed MECP2 was detected immunochemically in heterochromatic puncta of both cell types, indicating wild type DNA binding function. Notably, MECP2-positive neurons in the CA3 region of scAAV9/MECP2-injected males had significantly larger somal sizes than MECP2-negative neurons.

Figure 18:
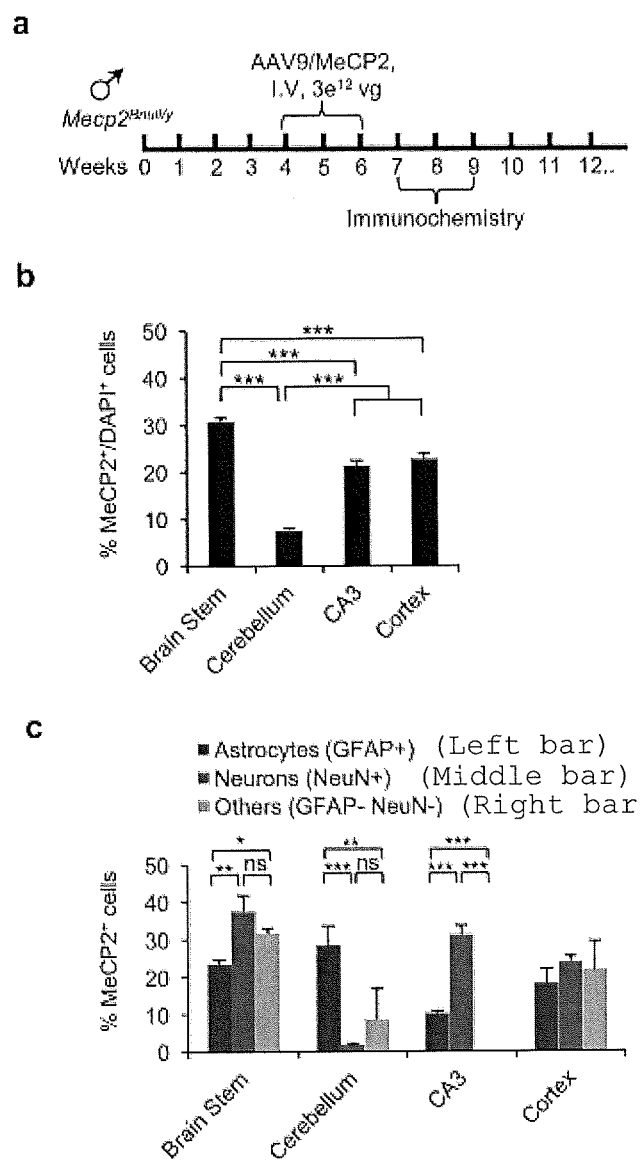
FIG. 18 shows that systemic injection of $MECP2B^{null/y}$ mice with scAAV9/MECP2 virus results in MECP2 expression in different cell types in brain. (a) Experimental paradigm. (b) MECP2 expression is expressed preferentially in brainstem of injected mice (n=3). (c) Expression of MECP2 in neurons and non neuronal cells varies with brain region (n=3). In panels b and c *$P<0.05$, $P<0.01$ and *$P<0.001$ by one way ANOVA (Newman-Keuls multiple comparison test). Data are means±s.e.m.
Figure 19:
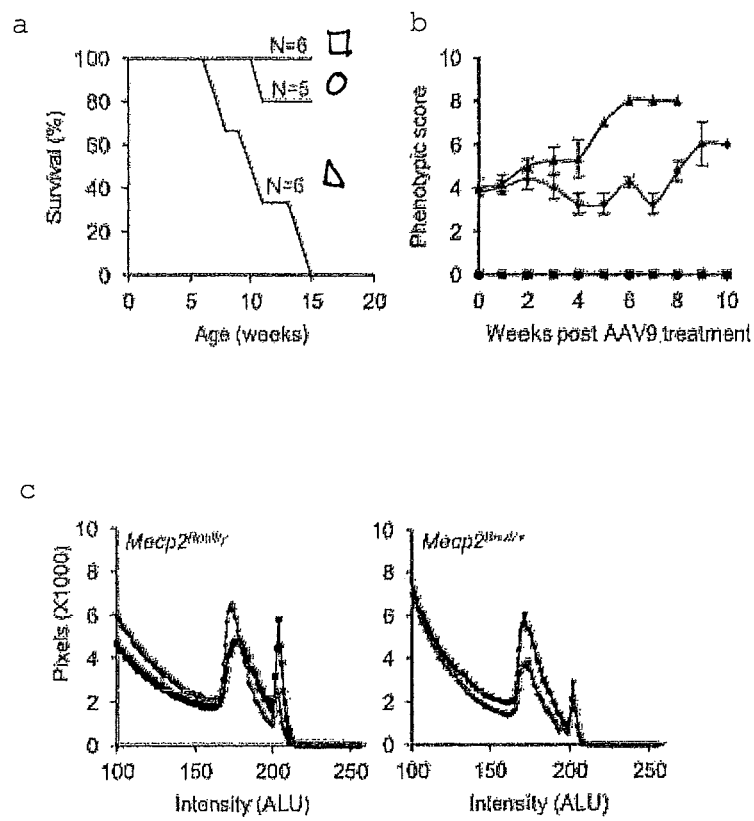
FIG. 19 shows MECP2 expressed from virus binds to DNA, restores normal neuronal somal size and improves survival. (f) Kaplan-Meier survival curve. (g) Observational scores. MECP2Bnull/y-scAAV9/MECP2 (n=5), MECP2Bnull/y-AAV9/Control (n=6), MECP2+/y (n=6). Data are means±s.e.m. (h) Field pixel intensities of MECP2-Cy3 immunofluorescence measured from brainstem sections of non-injected and scAAV9/MECP2-injected males (left) and females (right). n=10 fields each condition. ALU, Arbitrary Linear Unit.

The MECP2 expressed from scAAV9/MECP2 was detected throughout the brain. However, with the exception of cerebellum, MECP2 expression was not over represented in astrocytes, (FIG. 18). This could reflect, in part, the specific cell specific regulatory elements in the cloned promoter fragment because MECP2 is expressed generally at lower levels in astocytes than neurons [Ballas et al., Nature Neuroscience, 12: 311-317 (2009) and Skene et al., Molecular Cell, 37: 457-468 (2010)]. Consistent with all of these metrics, the injected male mice had prolonged lifespans and improved observational scores compared to control injected mice (FIG. 19, panels a and b).

A potential concern with virally-mediated gene transfer of MECP2 is over-expression, because MECP2 duplication gives rise to a neurological disease [del Gaudio et al., Genetics in Medicine, 8: 784-792 (2006) and Friez et al., Pediatrics, 118: e1687-1695 (2006)]. To assess this issue, in an unbiased manner, the average MECP2 expression level was determined in transduced brains by recording field pixel intensities of MECP2-Cy3 fluorescence in hindbrain sections selected randomly. The results indicated that scAAV9/MECP2 injection resulted in physiological levels of MECP2 protein (FIG. 19, panel c). Interestingly, WT brains showed two peaks of MECP2 fluorescence that were precisely recapitulated in the MECP2 transduced brains, although the cellular nature of the fluorescence is not identified by this method of analysis.

Having established that scAAV9/MECP2 programmed MECP2 expression to approximately physiological levels in multiple cell types in brain, rescue parameters were examined in 10 to 12 month-old symptomatic MECP2Bnull/+ mice that were systemically injected with scAAV9/MECP2 or control virus (FIG. 21). Like the males, there was no evidence for over-expression of MECP2 and viral therapy did not compromise survival (FIG. 19, panel c; FIG. 21). The observational scores increased initially from two to three. Strikingly, by 12-weeks, scAAV9/MECP2 injected females stabilized at an improved score of one until the end of scoring at 24-weeks, while females injected with control virus progressed to a score of nearly six (FIG. 20, panel b). The scAAV9/MECP2 injected MECP2Bnull/+ mice also performed significantly better than scAAV9/control females in rotorod, inverted grid and platform tests, and nesting ability (FIG. 20, panels c-f). None of the injected females exhibited seizures, unlike the females injected with control virus (2/5).

Previous gene therapy work has shown modest, but encouraging, improvement of symptoms in male mouse models of RTT [Gadalla et al., Mol. Ther., 21: 18-30 (2013)]. However, the disease initiates and progresses differently in females and males, due to the mosaic nature of MECP2 loss of function in females. Therefore, therapeutics designed especially for affected females are required. The results presented herein are important because they suggest, for the first time, that symptoms in human RTT female patients may be reversible by ectopic expression of MECP2 in a rAAV9 virus that infects peripheral tissue and multiple cell types within the CNS. Interestingly, the experiments also indicate that not every cell needs to be repaired with MECP2 in order to stabilize or reverse phenotypes in female mice, consistent with the finding that an ~5% increase in MECP2 levels over WT levels is sufficient to mediate longer lifespans [Robinson et al., Brain, 135: 2699-2710 (2012) and Lioy et al. (2011).

While the present invention has been described in terms of various embodiments and examples, it is understood that variations and improvements will occur to those skilled in the art. Therefore, only such limitations as appear in the claims should be placed on the invention.

All documents referred to in this application, including priority documents, are hereby incorporated by reference in their entirety with particular attention to the content for which they are referred.

The invention claimed is:

1. A method of delivering a methyl-CpG-binding protein 2 (MECP2) polynucleotide to the central nervous system of a female Rett syndrome patient in need thereof comprising administering a recombinant adeno-associated virus 9 (rAAV9) to the female patient by direct intravenous injection, wherein the rAAV9 comprises a MECP2 polynucleotide in a self-complementary genome, wherein the MECP2 polynucleotide is expressed in neuronal and glial cells in the central nervous system, and wherein seizures are reduced in the female patient.

2. A method of treating Rett syndrome female patient comprising administering a rAAV9 to the female patient by direct intravenous injection, wherein the rAAV9 comprises a MECP2 polynucleotide in a self-complementary genome and wherein the MECP2 polynucleotide is expressed in neuronal and glial cells in the central nervous system, and wherein seizures are reduced in the female patient.

3. A rAAV9 with a self-complementary genome encoding MECP2.

* * * * *

UNITED STATES PATENT AND TRADEMARK OFFICE
CERTIFICATE OF CORRECTION

PATENT NO. : 9,415,121 B2
APPLICATION NO. : 13/830515
DATED : August 16, 2016
INVENTOR(S) : Brian K. Kaspar et al.

Page 1 of 1

It is certified that error appears in the above-identified patent and that said Letters Patent is hereby corrected as shown below:

In the Specification

At Column 1, Line 22, replace "R21EY018491 awarded by the National Institutes of Health (NIH)/National Eye Institute (NEI), under R21NS064328, awarded by the NIH/National Institute of Neurological Disorders and Stroke (NINDS) and under RC2 NS69476-01 awarded by the National Institutes of Health (NIH)" with --EY018491, NS069476 and NS064328 awarded by the National Institutes of Health--

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 14

<210> SEQ ID NO 1
<211> LENGTH: 1621
<212> TYPE: DNA
<213> ORGANISM: Homo sapiens

<400> SEQUENCE: 1
ccacaaatgt gggagggcga taaccactcg tagaaagcgt gagaagttac tacaagcggt      60
cctcccggcc accgtactgt tccgctccca gaagccccgg gcggcggaag tcgtcactct     120
taagaaggga cggggcccca cgctgcgcac ccgcgggttt gctatggcga tgagcagcgg     180
cggcagtggt ggcggcgtcc cggagcagga ggattccgtg ctgttccggc gcggcacagg     240
ccagagcgat gattctgaca tttgggatga tacagcactg ataaaagcat atgataaagc     300
tgtggcttca tttaagcatg ctctaaagaa tggtgacatt tgtgaaactt cgggtaaacc     360
aaaaaccaca cctaaaagaa aacctgctaa gaagaataaa agccaaaaga agaatactgc     420
agcttcctta caacagtgga aagttgggga caaatgttct gccatttggt cagaagacgg     480
ttgcatttac ccagctacca ttgcttcaat tgattttaag agagaaacct gtgttgtggt     540
ttacactgga tatggaaata gagaggagca aaatctgtcc gatctacttt ccccaatctg     600
tgaagtagct aataatatag aacagaatgc tcaagagaat gaaaatgaaa gccaagtttc     660
aacagatgaa agtgagaact ccaggtctcc tggaaataaa tcagataaca tcaagcccaa     720
```

```
atctgctcca tggaactctt ttctccctcc accacccccc atgccagggc caagactggg      780
accaggaaag ccaggtctaa aattcaatgg cccaccaccg ccaccgccac caccaccacc      840
ccacttacta tcatgctggc tgcctccatt tccttctgga ccaccaataa ttcccccacc      900
acctcccata tgtccagatt ctcttgatga tgctgatgct ttgggaagta tgttaatttc      960
atggtacatg agtggctatc atactggcta ttatatgggt ttcagacaaa atcaaaaga     1020 aggaaggtgc tcacattcct taaattaagg agaaatgctg gcatagagca gcactaaatg     1080
acaccactaa agaaacgatc agacagatct ggaatgtgaa gcgttataga agataactgg     1140
cctcatttct tcaaaatatc aagtgttggg aagaaaaaa ggaagtggaa tgggtaactc     1200
ttcttgatta aaagttatgt aataaccaaa tgcaatgtga atatttttac tggactcttt     1260
tgaaaaacca tctgtaaaag actggggtgg gggtgggagg ccagcacggt ggtgaggcag     1320
ttgagaaaat ttgaatgtgg attagatttt gaatgatatt ggataattat tggtaatttt     1380
atggcctgtg agaagggtgt tgtagtttat aaaagactgt cttaatttgc atacttaagc     1440
atttaggaat gaagtgttag agtgtcttaa aatgtttcaa atggtttaac aaaatgtatg     1500
tgaggcgtat gtggcaaaat gttacagaat ctaactggtg gacatggctg ttcattgtac     1560 tgttttttc tatcttctat atgtttaaaa gtatataata aaaatattta atttttttt      1620 a                                                                      1621

<210> SEQ ID NO 2
<211> LENGTH: 24
<212> TYPE: DNA
<213> ORGANISM: Artificial Sequence
<220> FEATURE:
<223> OTHER INFORMATION: Synthetic nucleotide

<400> SEQUENCE: 2
tccagctccg ggatattggg attg                                              24

<210> SEQ ID NO 3
<211> LENGTH: 23
<212> TYPE: DNA
<213> ORGANISM: Artificial Sequence
<220> FEATURE:
<223> OTHER INFORMATION: Synthetic nucleotide

<400> SEQUENCE: 3
aggtcccacc acctaagaaa gcc                                               23

<210> SEQ ID NO 4
<211> LENGTH: 22
<212> TYPE: DNA
<213> ORGANISM: Artificial Sequence
<220> FEATURE:
<223> OTHER INFORMATION: Synthetic nucleotide

<400> SEQUENCE: 4
gtgtctgggc tgtaggcatt gc                                                22

<210> SEQ ID NO 5
<211> LENGTH: 22
<212> TYPE: DNA
<213> ORGANISM: Artificial Sequence
<220> FEATURE:
<223> OTHER INFORMATION: Synthetic nucleotide

<400> SEQUENCE: 5
```

```
gctgtgcctt ttggcttatc tg                                              22

<210> SEQ ID NO 6
<211> LENGTH: 25
<212> TYPE: DNA
<213> ORGANISM: Artificial Sequence
<220> FEATURE:
<223> OTHER INFORMATION: Synthetic nucleotide

<400> SEQUENCE: 6
gcctgcgatg tcggtttctg tgagg                                           25

<210> SEQ ID NO 7
<211> LENGTH: 21
<212> TYPE: DNA
<213> ORGANISM: Artificial Sequence
<220> FEATURE:
<223> OTHER INFORMATION: Synthetic nucleotide

<400> SEQUENCE: 7
ccagcgcgga tcggtcagac g                                               21

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
aacagtgcca gctgctcttc                                                 20

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
ctgtatcctt gggtcaagct g                                               21

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gccagaggcc acttgtgtag                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
ccaccctcca gtttggttta                                                 20

<210> SEQ ID NO 12
<211> LENGTH: 20
<212> TYPE: DNA
<213> ORGANISM: Artificial Sequence
```

```
<220> FEATURE:
<223> OTHER INFORMATION: Synthetic primer

<400> SEQUENCE: 12 gacccttgg gactgaagtt                                                    20

<210> SEQ ID NO 13
<211> LENGTH: 6391
<212> TYPE: DNA
<213> ORGANISM: Homo sapiens

<400> SEQUENCE: 13
gcccaatacg caaaccgcct ctccccgcgc gttggccgat tcattaatgc agctgattct      60
aacgaggaaa gcacgttata cgtgctcgtc aaagcaacca tagtacgcgc cctgtagcgg     120
cgcattaagc gcggcgggtg tggtggttac gcgcagcgtg accgctacac ttgccagcgc     180
cctagcgccc gctcctttcg ctttcttccc ttcctttctc gccacgttcg ccggctttcc     240
ccgtcaagct ctaaatcggg gctcccttt agggttccga tttagtgctt tacggcacct      300 cgacccaaa aaacttgatt agggtgatgg ttcacgtagt gggccatcgc cctgatagac      360 ggttttcgc cctttgacgt tggagtccac gttctttaat agtggactct tgttccaaac      420
tggaacaaca ctcaaccctta tctcggtcta ttcttttgat ttataaggga ttttgccgat    480
ttcggcctat tggttaaaaa atgagctgat ttaacaaaaa tttaacgcga attttaacaa    540
aatattaacg cttacaattt aaatatttgc ttatacaatc ttcctgtttt tggggctttt    600
ctgattatca accggggtac atatgattga catgctagtt ttacgattac cgttcatcgc    660
cctgcgcgct cgctcgctca ctgaggccgc ccgggcaaag cccgggcgtc gggcgacctt    720
tggtcgcccg gcctcagtga gcgagcgagc gcgcagagag ggagtggaat tcacgcgtgg    780
atctgaattc aattcacgcg tggtaccgag ctcggatcca ctagtaacgg ccgccagtgt    840
gctggaattc gcccttaatt ttccggacgg gttttaccac agccctctct ccgagaggag    900
ggagcgcgcg cgcaaccgat gccgggaccc cgcacggcag acgtcgcgcc ccgccctccc    960
gaccagcctg tgtgctgctg cacctgcgcg cccgcgcccc acccttgct ctttgtcgag     1020 attacccttc attggttgtg gagcccaggc tggggcggag ccttagcggt gacgccctca    1080
attggcagga gttcctgtct gtttaggcag ggaaaagagg cggacccccat tcagctgcgg    1140 attggtggag ttctactgtc acttggaaaa agaggcggc tagggcacag aggggctggt    1200
tttgtgggca gcatttgaat gttgaggatt aactgggccc ttgtggactc tggcgcttaa    1260
ggaagtctag gctcttggcg cctattagag cctccctgct gagtagttca ccattgtgat    1320
aagcatttga cttcaccagc atttctttat tatcattttc tgtagaagta gcaaagttgc    1380
ctgttgagga gcctggcgtt gttccaagcc aagggacttg ttttaaaggg tctactgatt    1440
gtattattac actaaattag cagatgtcgc actcttaagg ctgacagtaa aatcaacata    1500
tcaaaccttg gtctttgcag acgtttataa tgggcagatg gtgtgtgcca agcccataag    1560
agatcggtct gtcattgttg aatcagatgg tttgataact ggtaagttta gtcttttgt    1620 cttttattc aggtccccgga tccggtggtg gtgcaaatca aagaactgct cctcagtgga    1680
tgttgccttt acttctaggc ctgtacgaa gtgttacttc tgctctaaaa gctgcggaat    1740
tgtacccgcg gccgatccac cggttttaag ggccgaggcg gccagatctt cgaagatat    1800 ggccgccgct gccgccaccg ccgccgccgc gccgcgccg agcggaggag gaggaggagg    1860
cgaggaggag agactggagg aaaagtcaga agaccaggat ctccagggcc tcagagacaa    1920
```

-continued

```
gccactgaag tttaagaagg cgaagaaaga caagaaggag gacaaagaag gcaagcatga    1980
gccactacaa ccttcagccc accattctgc agagccagca gaggcaggca aagcagaaac    2040
atcagaaagc tcaggctctg ccccagcagt gccagaagcc tcggcttccc ccaaacagcg    2100
gcgctccatt atccgtgacc ggggacctat gtatgatgac cccaccttgc ctgaaggttg    2160
gacacgaaag cttaaacaaa ggaagtctgg ccgatctgct ggaaagtatg atgtatattt    2220
gatcaatccc cagggaaaag cttttcgctc taaagtagaa ttgattgcat actttgaaaa    2280
ggtgggagac acctccttgg accctaatga ttttgacttc acggtaactg ggagagggag    2340
cccctccagg agagagcaga aaccacctaa gaagcccaaa tctcccaaag ctccaggaac    2400
tggcaggggt cggggacgcc ccaaagggag cggcactggg agaccaaagg cagcagcatc    2460
agaaggtgtt caggtgaaaa gggtcctgga agagccct gggaaacttg ttgtcaagat    2520
gccttcccaa gcatcgcctg ggggtaaggg tgagggaggt ggggctacca catctgccca    2580
ggtcatggtg atcaaacgcc ctggcagaaa gcgaaaagct gaagctgacc cccaggccat    2640
tcctaagaaa cggggtagaa agcctgggag tgtggtggca gctgctgcag ctgaggccaa    2700
aaagaaagcc gtgaaggagt cttccatacg gtctgtgcat gagactgtgc tccccatcaa    2760
gaagcgcaag acccgggaga cggtcagcat cgaggtcaag gaagtggtga agcccctgct    2820
ggtgtccacc cttggtgaga aaagcgggaa gggactgaag acctgcaaga gccctgggcg    2880
taaaagcaag gagagcagcc caaggggcg cagcagcagt gcctcctccc cacctaagaa    2940
ggagcaccat catcaccacc atcactcaga gtccacaaag gccccatgc cactgctccc    3000 atccccaccc ccacctgagc ctgagagctc tgaggacccc atcagccccc ctgagcctca    3060
ggacttgagc agcagcatct gcaaagaaga gaagatgccc cgaggaggct cactggaaag    3120
cgatggctgc cccaaggagc cagctaagac tcagcctatg gtcgccacca ctaccacagt    3180
tgcagaaaag tacaaacacc gaggggaggg agagcgcaaa gacattgttt catcttccat    3240
gccaaggcca aacagagagg agcctgtgga cagccggacg cccgtgaccg agagagttag    3300
ctgaatcggc gccgctagcg cggccgcgtt taaaccctgc aggtctagaa agcttatcga    3360
taccgtcgac tagagctcgc tgatcagcct cgactgtgcc ttctagttgc cagccatctg    3420
ttgtttgccc ctcccccgtg ccttccttga ccctggaagg tgccactccc actgtccttt    3480
cctaataaaa tgaggaaatt gcatcgcatt gtctgagtag gtgtcattct attctggggg    3540
gtggggtggg gcaggacagc aagggggagg attgggaaga caatagcagg catgctgggg    3600
agagatcgat ctgaggaacc cctagtgatg gagttggcca ctccctctct gcgcgctcgc    3660
tcgctcactg aggccgggcg accaaaggtc gcccgacgcc cgggctttgc ccgggcggcc    3720
tcagtgagcg agcgagcgcg cagagaggga gtggcccccc cccccccccc cccggcgatt    3780
ctcttgtttg ctccagactc tcaggcaatg acctgatagc ctttgtagag acctctcaaa    3840
aatagctacc ctctccggca tgaatttatc agctagaacg gttgaatatc atattgatgg    3900
tgatttgact gtctccggcc tttctcaccc gtttgaatct ttacctacac attactcagg    3960
cattgcattt aaaatatatg agggttctaa aaatttttat ccttgcgttg aaataaaggc    4020
ttctcccgca aaagtattac agggtcataa tgttttggt acaaccgatt tagctttatg    4080
ctctgaggct ttattgctta attttgctaa ttctttgcct tgcctgtatg atttattgga    4140
tgttggaatc gcctgatgcg gtattttctc cttacgcatc tgtgcggtat ttcacaccgc    4200
atatggtgca ctctcagtac aatctgctct gatgccgcat agttaagcca gccccgacac    4260
ccgccaacac ccgctgacgc gccctgacgg gcttgtctgc tcccggcatc cgcttacaga    4320
```

```
caagctgtga ccgtctccgg gagctgcatg tgtcagaggt tttcaccgtc atcaccgaaa    4380
cgcgcgagac gaaagggcct cgtgatacgc ctattttat aggttaatgt catgataata    4440
atggtttctt agacgtcagg tggcactttt cggggaaatg tgcgcggaac ccctatttgt    4500 ttattttct aaatacattc aaatatgtat ccgctcatga acaataacc ctgataaatg    4560 cttcaataat attgaaaaag gaagagtatg agtattcaac atttccgtgt cgcccttatt    4620 ccctttttg cggcattttg ccttcctgtt tttgctcacc cagaaacgct ggtgaaagta    4680
aaagatgctg aagatcagtt gggtgcacga gtgggttaca tcgaactgga tctcaacagc    4740
ggtaagatcc ttgagagttt tcgccccgaa gaacgttttc caatgatgag cacttttaaa    4800
gttctgctat gtggcgcggt attatcccgt attgacgccg ggcaagagca actcggtcgc    4860
cgcatacact attctcagaa tgacttggtt gagtactcac cagtcacaga aaagcatctt    4920
acggatggca tgacagtaag agaattatgc agtgctgcca taaccatgag tgataacact    4980
gcggccaact tacttctgac aacgatcgga ggaccgaagg agctaaccgc ttttttgcac    5040
aacatggggg atcatgtaac tcgccttgat cgttgggaac cggagctgaa tgaagccata    5100
ccaaacgacg agcgtgacac cacgatgcct gtagcaatgg caacaacgtt gcgcaaacta    5160
ttaactggcg aactacttac tctagcttcc cggcaacaat taatagactg gatggaggcg    5220
gataaagttg caggaccact tctgcgctcg gcccttccgg ctggctggtt tattgctgat    5280
aaatctggag ccggtgagcg tgggtctcgc ggtatcattg cagcactggg gccagatggt    5340
aagccctccc gtatcgtagt tatctacacg acggggagtc aggcaactat ggatgaacga    5400
aatagacaga tcgctgagat aggtgcctca ctgattaagc attggtaact gtcagaccaa    5460
gtttactcat atatacttta gattgattta aaacttcatt tttaatttaa aaggatctag    5520
gtgaagatcc ttttttgataa tctcatgacc aaaatccctt aacgtgagtt ttcgttccac    5580
tgagcgtcag accccgtaga aaagatcaaa ggatcttctt gagatccttt ttttctgcgc    5640
gtaatctgct gcttgcaaac aaaaaaacca ccgctaccag cggtggtttg tttgccggat    5700
caagagctac caactctttt tccgaaggta actggcttca gcagagcgca gataccaaat    5760
actgtccttc tagtgtagcc gtagttaggc caccacttca agaactctgt agcaccgcct    5820
acatacctcg ctctgctaat cctgttacca gtggctgctg ccagtggcga taagtcgtgt    5880
cttaccgggt tggactcaag acgatagtta ccggataagg cgcagcggtc gggctgaacg    5940
gggggttcgt gcacacagcc cagcttggag cgaacgacct acaccgaact gagatacccta    6000 cagcgtgagc tatgagaaag cgccacgctt cccgaaggga gaaaggcgga caggtatccg    6060
gtaagcggca gggtcggaac aggagagcgc acgagggagc ttccaggggg aaacgcctgg    6120
tatctttata gtcctgtcgg gtttcgccac ctctgacttg agcgtcgatt tttgtgatgc    6180
tcgtcagggg gcggagcct atggaaaaac gccagcaacg cggccttttt acggttcctg    6240
gccttttgct ggccttttgc tcacatgttc tttcctgcgt tatcccctga ttctgtggat    6300
aaccgtatta ccgcctttga gtgagctgat accgctcgcc gcagccgaac gaccgagcgc    6360
agcgagtcag tgagcgagga agcggaagag c                                 6391
```

<210> SEQ ID NO 14
<211> LENGTH: 6317
<212> TYPE: DNA
<213> ORGANISM: Homo sapiens

<400> SEQUENCE: 14

-continued

```
gcccaatacg caaaccgcct ctccccgcgc gttggccgat tcattaatgc agctgattct    60
aacgaggaaa gcacgttata cgtgctcgtc aaagcaacca tagtacgcgc cctgtagcgg   120
cgcattaagc gcggcgggtg tggtggttac gcgcagcgtg accgctacac ttgccagcgc   180
cctagcgccc gctcctttcg ctttcttccc ttcctttctc gccacgttcg ccggctttcc   240
ccgtcaagct ctaaatcggg gctcccttt aggttccga tttagtgctt tacggcacct    300
cgaccccaaa aaacttgatt agggtgatgg ttcacgtagt gggccatcgc cctgatagac   360 ggttttcgc cctttgacgt tggagtccac gttctttaat agtggactct tgttccaaac    420
tggaacaaca ctcaaccta tctcggtcta ttcttttgat ttataaggga ttttgccgat    480
ttcggcctat tggttaaaaa atgagctgat ttaacaaaaa tttaacgcga atttaacaa    540 aatattaacg cttacaattt aaatatttgc ttatacaatc ttcctgtttt tggggctttt   600
ctgattatca accggggtac atatgattga catgctagtt ttacgattac cgttcatcgc   660
cctgcgcgct cgctcgctca ctgaggccgc ccgggcaaag cccgggcgtc gggcgacctt   720
tggtcgcccg gcctcagtga gcgagcgagc gcgcagagag gagtggaat tcacgcgtgg    780 atctgaattc aattcacgcg tggtaccgag ctcggatcca ctagtaacgg ccgccagtgt   840 gctgaattc gcccttaatt ttccggacgg gttttaccac agccctctct ccgagaggag   900
ggagcgcgcg cgcaaccgat gccgggaccc cgcacggcag acgtcgcgcc ccgccctccc   960
gaccagcctg tgtgctgctg cacctgcgcg cccgcgcccc accccttgct ctttgtcgag  1020
attacccttc attggttgtg gagcccaggc tggggcggag ccttagcggt gacgccctca  1080
attggcagga gttcctgtct gtttaggcag ggaaaagagg cggaccccat tcagctgcgg  1140
attggtggag ttctactgtc acttggaaaa aagaggcggc tagggcacag aggggctggt  1200
tttgtgggca gcatttgaat gttgaggatt aactgggccc ttgtggactc tggcgcttaa  1260
ggaagtctag gctcttggcg cctattagag cctccctgct gagtagttca ccattgtgat  1320
aagcatttga cttcaccagc atttctttat tatcattttc tgtagaagta gcaaagttgc  1380
ctgttgagga gcctggcgtt gttccaagcc aagggacttg ttttaaaggg tctactgatt  1440
gtattattac actaaattag cagatgtcgc actcttaagg ctgacagtaa atcaacata   1500 tcaaaccttg gtctttgcag acgtttataa tgggcagatg gtgtgtgcca agcccataag  1560
agatcggtct gtcattgttg aatcagatgg tttgataact ggtaagttta gtcttttgt   1620 cttttatttc aggtcccgga tccggtggtg gtgcaaatca aagaactgct cctcagtgga  1680
tgttgccttt acttctaggc ctgtacgaa gtgttacttc tgctctaaaa gctgcggaat   1740
tgtacccgcg gccgatccac cggtatggcc gccgccgccg ccgccgcgcc gagcggagga  1800
ggaggaggag gcgaggagga gagactggaa gaaaagtcag aagaccagga cctccagggc  1860
ctcaaggaca aacccctcaa gtttaaaaag gtgaagaaag ataagaaaga agagaaagag  1920
ggcaagcatg agcccgtgca gccatcagcc caccactctg ctgagcccgc agaggcaggc  1980
aaagcagaga catcagaagg gtcaggctcc gccccggctg tgccggaagc ttctgcctcc  2040
cccaaacagc ggcgctccat catccgtgac cggggaccca tgtatgatga ccccacccctg 2100 cctgaaggct ggacacggaa gcttaagcaa aggaaatctg gccgctctgc tgggaagtat  2160
gatgtgtatt tgatcaatcc ccagggaaaa gcctttcgct ctaaagtgga gttgattgcg  2220
tacttcgaaa aggtaggcga cacatccctg gaccctaatg attttgactt cacggtaact  2280
gggagaggga gccctcccg gcgagagcag aaaccccta agaagcccaa atctcccaaa    2340
gctccaggaa ctgcagagg ccggggacgc cccaaaggga gcggcaccac gagacccaag  2400
```

-continued

```
gcggccacgt cagagggtgt gcaggtgaaa agggtcctgg agaaaagtcc tgggaagctc    2460
cttgtcaaga tgccttttca aacttcgcca gggggcaagg ctgagggggg tggggccacc    2520
acatccaccc aggtcatggt gatcaaacgc cccggcagga agcgaaaagc tgaggccgac    2580
cctcaggcca ttcccaagaa acggggccga agccggggga gtgtggtggc agccgctgcc    2640
gccgaggcca aaagaaagc cgtgaaggag tcttctatcc gatctgtgca ggagaccgta    2700
ctccccatca agaagcgcaa gacccgggag acggtcagca tcgaggtcaa ggaagtggtg    2760
aagcccctgc tggtgtccac cctcggtgag aagagcggga aaggactgaa gacctgtaag    2820
agccctgggc ggaaaagcaa ggagagcagc cccaaggggc gcagcagcag cgcctcctca    2880
ccccccaaga aggagcacca ccaccatcac caccactcag agtccccaaa ggcccccgtg    2940
ccactgctcc caccctgcc cccacctcca cctgagcccg agagctccga ggaccccacc    3000
agcccccctg agcccagga cttgagcagc agcgtctgca aagaggagaa gatgcccaga    3060
ggaggctcac tggagagcga cggctgcccc aaggagccag ctaagactca gcccgcggtt    3120
gccaccgccg ccacggccgc agaaaagtac aaacaccgag gggagggaga gcgcaaagac    3180
attgtttcat cctccatgcc aaggccaaac agagaggagc ctgtggacag ccggacgccc    3240
gtgaccgaga gagttagctg acctgcaggt ctagaaagct tatcgatacc gtcgactaga    3300
gctcgctgat cagcctcgac tgtgccttct agttgccagc catctgttgt ttgcccctcc    3360
cccgtgcctt ccttgaccct ggaaggtgcc actcccactg tcctttccta ataaaatgag    3420
gaaattgcat cgcattgtct gagtaggtgt cattctattc tggggggtgg ggtggggcag    3480
gacagcaagg gggaggattg ggaagacaat agcaggcatg ctggggagag atcgatctga    3540
ggaaccccta gtgatggagt tggccactcc ctctctgcgc gctcgctcgc tcactgaggc    3600
cgggcgacca aggtcgccc gacgcccggg ctttgcccgg gcggcctcag tgagcgagcg    3660
agcgcgcaga gagggagtgg ccccccccc ccccccccg gcgattctct tgtttgctcc    3720
agactctcag gcaatgacct gatagccttt gtagagacct ctcaaaaata gctaccctct    3780
ccggcatgaa tttatcagct agaacggttg aatatcatat tgatggtgat ttgactgtct    3840
ccggcctttc tcacccgttt gaatctttac ctacacatta tcaggcatt gcatttaaaa    3900 tatatgaggg ttctaaaaat ttttatcctt gcgttgaaat aaaggcttct cccgcaaaag    3960
tattacaggg tcataatgtt tttggtacaa ccgatttagc tttatgctct gaggctttat    4020
tgcttaattt tgctaattct ttgccttgcc tgtatgattt attggatgtt ggaatcgcct    4080
gatgcggtat tttctcctta cgcatctgtg cggtatttca caccgcatat ggtgcactct    4140
cagtacaatc tgctctgatg ccgcatagtt aagccagccc cgacacccgc caacacccgc    4200
tgacgcgccc tgacgggctt gtctgctccc ggcatccgct tacagacaag ctgtgaccgt    4260
ctccgggagc tgcatgtgtc agaggttttc accgtcatca ccgaaacgcg cgagacgaaa    4320
gggcctcgtg atacgcctat ttttataggt taatgtcatg ataataatgg tttcttagac    4380
gtcaggtggc acttttcggg gaaatgtgcg cggaacccct atttgtttat ttttctaaat    4440
acattcaaat atgtatccgc tcatgagaca ataaccctga taaatgcttc aataatattg    4500
aaaaaggaag agtatgagta ttcaacattt ccgtgtcgcc cttattccct ttttgcggc    4560 attttgcctt cctgtttttg ctcacccaga aacgctggtg aaagtaaaag atgctgaaga    4620
tcagttgggt gcacgagtgg gttacatcga actggatctc aacagcggta agatccttga    4680
gagttttcgc cccgaagaac gttttccaat gatgagcact tttaaagttc tgctatgtgg    4740
```

```
                                                -continued
cgcggtatta tcccgtattg acgccgggca agagcaactc ggtcgccgca tacactattc    4800
tcagaatgac ttggttgagt actcaccagt cacagaaaag catcttacgg atggcatgac    4860
agtaagagaa ttatgcagtg ctgccataac catgagtgat aacactgcgg ccaacttact    4920
tctgacaacg atcggaggac cgaaggagct aaccgctttt ttgcacaaca tgggggatca    4980
tgtaactcgc cttgatcgtt gggaaccgga gctgaatgaa gccataccaa acgacgagcg    5040
tgacaccacg atgcctgtag caatggcaac aacgttgcgc aaactattaa ctggcgaact    5100
acttactcta gcttcccggc aacaattaat agactggatg gaggcggata aagttgcagg    5160
accacttctg cgctcggccc ttccggctgg ctggtttatt gctgataaat ctggagccgg    5220
tgagcgtggg tctcgcggta tcattgcagc actgggccca gatggtaagc cctcccgtat    5280
cgtagttatc tacacgacgg ggagtcaggc aactatggat gaacgaaata gacagatcgc    5340
tgagataggt gcctcactga ttaagcattg gtaactgtca gaccaagttt actcatatat    5400
actttagatt gatttaaaac ttcatttta atttaaaagg atctaggtga agatcctttt    5460
tgataatctc atgaccaaaa tcccttaacg tgagttttcg ttccactgag cgtcagaccc    5520
cgtagaaaag atcaaaggat cttcttgaga tcctttttt ctgcgcgtaa tctgctgctt    5580
gcaaacaaaa aaaccaccgc taccagcggt ggtttgtttg ccggatcaag agctaccaac    5640 tcttttccg aaggtaactg gcttcagcag agcgcagata ccaaatactg tccttctagt    5700
gtagccgtag ttaggccacc acttcaagaa ctctgtagca ccgcctacat acctcgctct    5760
gctaatcctg ttaccagtgg ctgctgccag tggcgataag tcgtgtctta ccgggttgga    5820
ctcaagacga tagttaccgg ataaggcgca gcggtcgggc tgaacggggg gttcgtgcac    5880
acagcccagc ttggagcgaa cgacctacac cgaactgaga tacctacagc gtgagctatg    5940
agaaagcgcc acgcttcccg aagggagaaa ggcggacagg tatccggtaa gcggcagggt    6000
cggaacagga gagcgcacga gggagcttcc agggggaaac gcctggtatc tttatagtcc    6060
tgtcgggttt cgccacctct gacttgagcg tcatttttg tgatgctcgt caggggggcg    6120
gagcctatgg aaaaacgcca gcaacgcggc ctttttacgg ttcctggcct tttgctggcc    6180
ttttgctcac atgttctttc ctgcgttatc ccctgattct gtggataacc gtattaccgc    6240
ctttgagtga gctgataccg ctcgccgcag ccgaacgacc gagcgcagcg agtcagtgag    6300
cgaggaagcg gaagagc                                                  6317
```